US011767303B2

(12) United States Patent
Li et al.

(10) Patent No.: US 11,767,303 B2
(45) Date of Patent: Sep. 26, 2023

(54) COMPOUNDS AND METHODS FOR INHIBITING VIRAL REPLICATION AND METHODS OF TREATING AND PREVENTING FLAVIVIRAL INFECTIONS

(71) Applicants: Health Research, Inc., Menands, NY (US); Arizona Board of Regents on Behalf of the University of Arizona, Tucson, AZ (US); Board of Regents, The University of Texas System, Austin, TX (US)

(72) Inventors: Hongmin Li, Tucson, AZ (US); Zhong Li, Tucson, AZ (US); Jia Zhou, League City, TX (US); Jimin Xu, Galveston, TX (US); Qing-Yu Zhang, Tucson, AZ (US)

(73) Assignees: HEALTH RESEARCH, INC., Menands, NY (US); BOARD OF REGENTS, THE UNIVERSITY OF TEXAS SYSTEM, Austin, TX (US); ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 17/384,051

(22) Filed: Jul. 23, 2021

(65) Prior Publication Data

US 2022/0024884 A1 Jan. 27, 2022

Related U.S. Application Data

(60) Provisional application No. 63/056,011, filed on Jul. 24, 2020.

(51) Int. Cl.

| | |
|---|---|
| ***A61K 31/5375*** | (2006.01) |
| ***C07D 265/30*** | (2006.01) |
| ***C07C 233/75*** | (2006.01) |
| ***C07D 211/46*** | (2006.01) |
| ***A61P 31/14*** | (2006.01) |
| ***C07D 409/12*** | (2006.01) |
| ***C07D 213/75*** | (2006.01) |
| ***C07D 333/54*** | (2006.01) |

(52) U.S. Cl.

CPC ............ *C07D 265/30* (2013.01); *A61P 31/14* (2018.01); *C07C 233/75* (2013.01); *C07D 211/46* (2013.01); *C07D 213/75* (2013.01); *C07D 333/54* (2013.01); *C07D 409/12* (2013.01)

(58) Field of Classification Search

None

See application file for complete search history.

(56) References Cited

U.S. PATENT DOCUMENTS

| | | | |
|---|---|---|---|
| 2009/0304803 A1 | 12/2009 | Hasan | |
| 2011/0000480 A1 | 1/2011 | Turner et al. | |
| 2019/0016743 A1 | 1/2019 | Yen et al. | |
| 2019/0160028 A1 | 5/2019 | Li et al. | |
| 2020/0046659 A1 | 2/2020 | Melnyk | |

FOREIGN PATENT DOCUMENTS

| | | |
|---|---|---|
| WO | 2008021088 A2 | 2/2008 |
| WO | 2016193136 A1 | 12/2016 |

OTHER PUBLICATIONS

Wang et al., "Suppression of the Growth and Invasion of Human Head and Neck Squamous Cell Carcinomas via Regulating STAT3 Signaling and the miR-21/β-catenin Axis with HJC0152," Molecular Cancer Therapeutics 16(4):578-590 (2017).

Xu et al., "Discovery of Niclosamide and its O-alkylamino-tethered Derivatives as Potent Antibacterial Agents Against Carbapenemase-producing and/or Colistin Resistant Enterobacteriaceae Isolates," Bioorganic & Medicinal Chemistry Letters 29:1399-1402 (2019).

Chen et al., "Fragment-based Drug Design and Identification of HJC0123, A Novel Orally Bioavailable STAT3 Inhibitor For Cancer Therapy," European Journal of Medicinal Chemistry 62:498-507 (2013).

Chen et al., "Discovery of Potent Anticancer Agent HJC0416, An Orally Bioavailable Small Molecule Inhibitor of Signal Transducer and Activator of Transcription 3 (STAT3)," European Journal of Medicinal Chemistry 82:195-203 (2014).

Fan et al., "Dual Activity of Niclosamide to Suppress Replication of Integrated HIV-1 and *Mycobacterium tuberculosis* (Beijing)," Tuberculosis 116:S28-S33 (2019).

Chen et al., "Discovery of O-Alkylamino-Tethered Niclosamide Derivatives as Potent and Orally Bioavailable Anticancer Agents," ACS Med. Chem. Lett. 4:180-185 (2013).

Sack et al., "Novel Effect of Antihelminthic Niclosamide on S100A4-Mediated Metastatic Progression in Colon Cancer," J. Natl. Cancer Inst. 103:1018-1036 (2011).

Xu et al., "Broad Spectrum Antiviral Agent Niclosamide and Its Therapeutic Potential," ACS Infect. Dis. 6:909-915 (2020).

Yang, D., "Structural Studies of Terpenoid Biosynthesis and Bacterial Cell Division," Dissertation Submitted to the Office of Graduate Studies of Texas A&M University (Aug. 2006) (191 pages).

(Continued)

*Primary Examiner* — Samantha L Shterengarts

(74) *Attorney, Agent, or Firm* — HESLIN ROTHENBERG FARLEY & MESITI P.C.

(57) ABSTRACT

The present disclosure relates to a compound of formula (I) or a pharmaceutically acceptable salt thereof. The present disclosure further relates to methods of inhibiting viral replication including contacting one or more cells that have been infected with a virus with an effective amount of a compound of formula (I) or a pharmaceutically acceptable salt thereof, wherein the virus comprises a flavivirus. Also disclosed is a method of treating and/or preventing a flavivirus infection and/or a condition resulting from a flavivirus infection including administering an effective amount of a compound of formula (I) or a pharmaceutically acceptable salt thereof under conditions effective to treat and/or prevent a flavivirus infection and/or a condition resulting from a flavivirus infection.

28 Claims, 9 Drawing Sheets

Specification includes a Sequence Listing.

(56) References Cited

OTHER PUBLICATIONS

Li et al., "JMX0207, a Niclosamide Derivative with Improved Pharmacokinetics, Suppresses Zika Virus Infection Both In Vitro and In Vivo," ACS Infection Diseases, 2020, 6:2616-2628.

Xu et al., "Identification of small-molecule inhibitors of Zika virus infection and induced neural cell death via a drug repurposing screen," Nature Medicine, 2016, 22(10):1101-1107.

Cheung et al., "Antiviral activity of lanatoside C against dengue virus infection," Antiviral Research, 2014, 111:93-99.

Jurgeit et al., "Niclosamide Is a Proton Carrier and Targets Acidic Endosomes with Broad Antiviral Effects," PLOS Pathogens, 2012, 8(10):e1002976.

Wang et al., "Antiviral activities of niclosamide and nitazoxanide against chikungunya virus entry and transmission," Antiviral Resarch, 2016, 135:81-90.

Li et al., "Existing drugs as broad-spectrum and potent inhibitors for Zika virus by targeting NS2B-NS3 interaction," Cell Research, 2017, 27(8):1046-1064.

Chen et al., "Computational Discovery of Niclosamide Ethanolamine, a Repurposed Drug Candidate That Reduces Growth of Hepatocellular Carcinoma Cells In Vitro and in Mice by Inhibiting Cell Division Cycle 37 Signaling," Gastroenterology, 2017, 152(8):2022-2036.

Benzamide, N-(2-chloro-4-nitrophenyl)-2-hydroxy-3-nitro, PubChem, National Library of Medicine, https://pubchem.ncbi.nlm.nih.gov/compound/186164, retrieved Aug. 3, 2022.

```
             1         10         20         30         40         50         60         70         80         90
DENV2         AGVLWDVPS PPPMGKAE-L EDGAYRIKQK GIL-GYSQIG AGVYKEGTFH TMWHVTRGAV LMHKGKRIEP SWADVKKDLI SYGGGWKLEG EWKEG
DENV1         SGVLWDTPS PPEVERAV-L DDGIYRILQR GLL-GRSQVG VGVFQEGVFH TMWHVTRGAV LMYQGKRLEP SWASVKKDLI SYGGGWRFQG SWNAG
DENV3         SGVLWDVPS PPETQKAE-L EEGVYRIKQQ GIF-GKTQVG VGVQKEGVFH TMWHVTRGAV LTHNGKRLEP NWASVKKDLI SYGGGWRLSA QWQKG
DENV4         SGALWDVPS PAATKKAA-L SEGVYRIMQR GLF-GKTQVG VGIHMEGVFH TMWHVTRGSV ICHETGRLEP SWADVRNDMI SYGGGWRLGD KWDKE
WNV           GGVLWDTPS PKEYKKGD-T TTGVYRIMTR GLL-GSYQAG AGVMVEGVFH TLWHTTKGAA LMSGEGRLDP YWGSVKEDRL CYGGPWKLQH KWNGQ
JEV           GGVFWDTPS PKPCSKGD-T TTGVYRIMAR GIL-GTYQAG VGVMYENVFH TLWHTTRGAA IMSGEGKLTP YWGSVKEDRI AYGGPWRFDR KWNGT
SLEV          GGALWDVPS PKVYPKGE-T KPGIYRIMTR GIL-GTFQAG VGVMHEGVFH TMWHATEGAV LRNGEGRLDP YAGDVRNDLI SYGGPWKLSA TWDGT
ZIKV          SGALWDVPA PKEVKKGE-T TDGVYRVMTR RLL-GSTQVG VGVMQEGVFH TMWHVTKGAA LRSGEGRLDP YWGDVKQDLV SYCGPWKLDA AWDGL
YFV          SGDVLWDIPT PKIIEECEHL EDGIYGIFQS TFL-GASQRG VGVAQGGVFH TMWHVTRGAF LVRNGKKLIP SWASVKEDLV AYGGSWKLEG RWDGE
TBEV         SDLVFSGQGG RERGDRPFEV KDGVYRIFSP GLFWGQNQVG VGYGSKGVLH TMWHVTRGAA LSIDDAVAGP YWADVREDVV CYGGAWSLEE KWKG-
POWV         TDLVFSGQLP DQGEKRSFDI KEGVYRIYAP GLFWGYRQIG VGYGTKGVLH TMWHVTRGAA LSVEGATSGP YWADVREDVV CYGGAWGLDK KWGG-
Consensus    ..gvlwd.ps p....k.... ..G!YrI..r gll.G..Q.G vGv..eGVfH T$WHvTrGA. l.....rl.P yWadVk.Dl! aYGG.W.l.. .W.g.

                    100        110        120        130        140        150        160        170        180
DENV2        EEVQVLALEP GKNPRAVQTK PGLFKTNAG- TIGAVSLDFS PGTSGSPIID KKGKVVGLYG NGVVTRSGAY VSAIAQTEKS IED-NPEIE
DENV1        EEVQVIAVEP GKNPKNVQTA PGTFKTPEG- EVGAIALDFK PGTSGSPIVN REGKIVGLYG NGVVTTSGTY VSAIAQAKAS QEGPLPEIE
DENV3        EEVQVIAVEP GKNPKNFQTT PGTFQTTTG- EIGAIALDFK PGTSGSPIIN REGKVVGLYG NGVVTKNGGY VSGIAQTNAE PDGPTPELE
DENV4        EDVQVLAIEP GKNPKHVQTK PGLFKTLTG- EIGAVTLDFK PGTSGSPIIN RKGKVIGLYG NGVVTKSGDY VSAITQAERI GE-PDYEVD
WNV          DEVQMIVVEP GKNVKNVQTK PGVFKTPEG- EIGAVTLDFP TGTSGSPIVD KNGDVIGLYG NGVIMPNGSY ISAIVQGERM DEPIPAGFE
JEV          DDVQVIVVEP GKAAVNIQTK PGVFRTPFG- EVGAVSLDYP RGTSGSPILD SNGDIIGLYG NGVELGDGSY VSAIVQGDRQ EEPVPEAYT
SLEV         EEVQMIAVAP GKPAINVQTT PGVFKTPLG- TIGAVTLDFP KGTSGSPIIN KKGEIIGLYG NGVLIGQGEY VSGIIQGERT EEPIPDAYN
ZIKV         SEVQLLAVPP GERARNIQTL PGIFKTKDG- DIGAVALDYP AGTSGSPILD KCGRVIGLYG NGVVIKNGSY VSAITQGKRE EETPVECFE
YFV          EEVQLIAAVP GKNVVNVQTK PSLFKVRNGG EIGAVALDYP SGTSGSPIVN RNGEVIGLYG NGILVGDNSF VSAISQTEVK EEGKEELQE
TBEV         ETVQVHAFPP GRAHEVHQCQ PGELILDTGR KLGAIPIDLV KGTSGSPILN AQGVVVGLYG NGLKT-NETY VSSIAQGEAE KSRPNLPQA
POWV         EVVQVHAFPP DSGHKIHQCQ PGKLNLEGGR VLGAIPIDLP RGTSGSPIIN AQGDVLGLYG NGLKS-NDVY ISSIAQGNVE KSRPEMPLA
Consensus    #eVQvia..P gkn..nvQt. Pg.fkt..G. eiGA!.lD.p .GTSGSPI.# ..G.!iGLYG NGv....g.% !Sai.Qge.. .e.p....e.
```

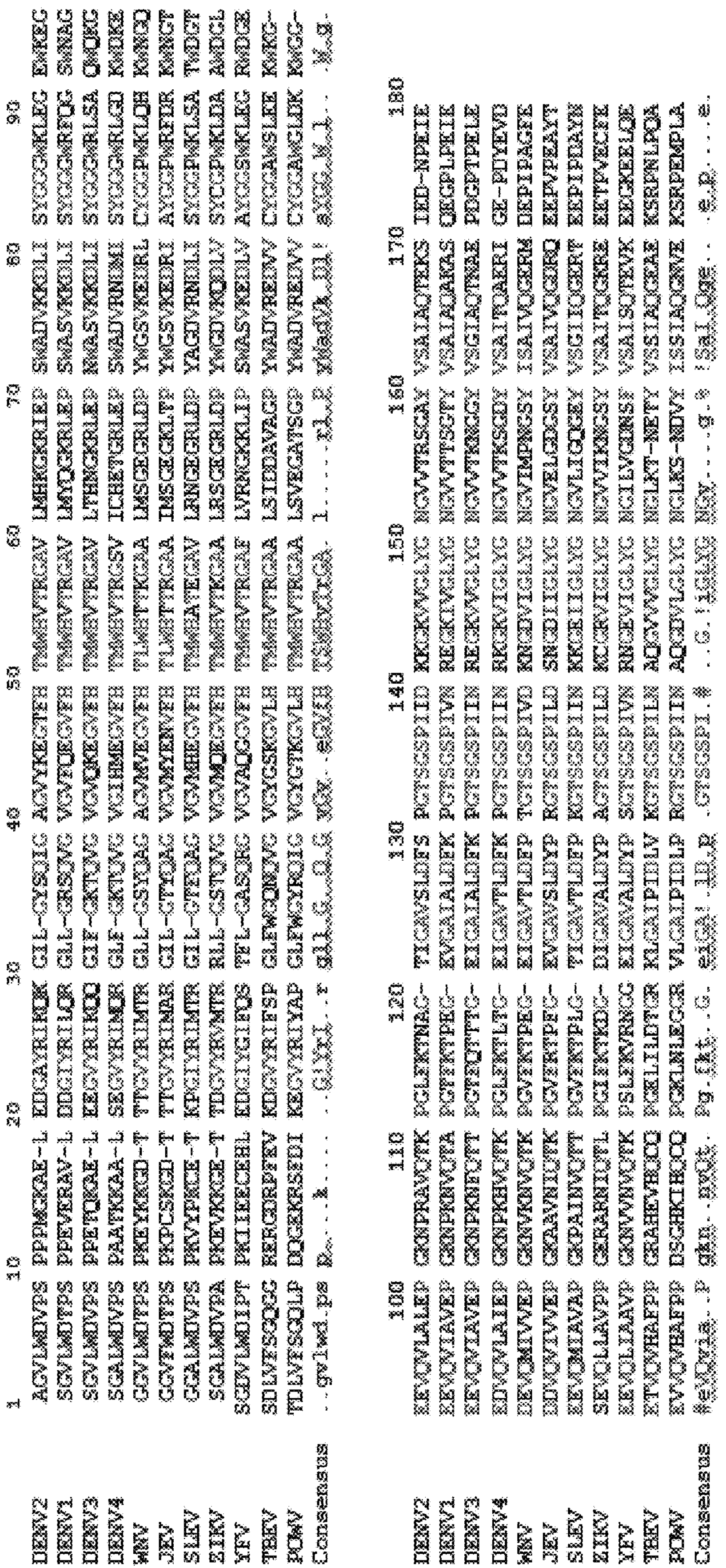

FIG. 8

Niclosamide

JMX0285

JMX0207

JMX0308

HJC0149

JMX0317

HJC0129

HJC0140

HJC0431

HJC0381

HJC0382

SEQUENCE LISTING

```
<160> NUMBER OF SEQ ID NOS: 14

<210> SEQ ID NO 1
<211> LENGTH: 179
<212> TYPE: PRT
<213> ORGANISM: Dengue virus type 2

<400> SEQUENCE: 1

Ala Gly Val Leu Trp Asp Val Pro Ser Pro Pro Pro Met Gly Lys Ala
1               5                   10                  15

Glu Leu Glu Asp Gly Ala Tyr Arg Ile Lys Gln Lys Gly Ile Leu Gly
            20                  25                  30

Tyr Ser Gln Ile Gly Ala Gly Val Tyr Lys Glu Gly Thr Phe His Thr
        35                  40                  45

Met Trp His Val Thr Arg Gly Ala Val Leu Met His Lys Gly Lys Arg
    50                  55                  60

Ile Glu Pro Ser Trp Ala Asp Val Lys Lys Asp Leu Ile Ser Tyr Gly
65                  70                  75                  80

Gly Gly Trp Lys Leu Glu Gly Glu Trp Lys Glu Gly Glu Glu Val Gln
                85                  90                  95

Val Leu Ala Leu Glu Pro Gly Lys Asn Pro Arg Ala Val Gln Thr Lys
            100                 105                 110

Pro Gly Leu Phe Lys Thr Asn Ala Gly Thr Ile Gly Ala Val Ser Leu
        115                 120                 125

Asp Phe Ser Pro Gly Thr Ser Gly Ser Pro Ile Ile Asp Lys Lys Gly
    130                 135                 140

Lys Val Val Gly Leu Tyr Gly Asn Gly Val Val Thr Arg Ser Gly Ala
145                 150                 155                 160

Tyr Val Ser Ala Ile Ala Gln Thr Glu Lys Ser Ile Glu Asp Asn Pro
                165                 170                 175

Glu Ile Glu


<210> SEQ ID NO 2
<211> LENGTH: 180
<212> TYPE: PRT
<213> ORGANISM: Dengue virus type 1

<400> SEQUENCE: 2

Ser Gly Val Leu Trp Asp Thr Pro Ser Pro Pro Glu Val Glu Arg Ala
1               5                   10                  15

Val Leu Asp Asp Gly Ile Tyr Arg Ile Leu Gln Arg Gly Leu Leu Gly
            20                  25                  30

Arg Ser Gln Val Gly Val Gly Val Phe Gln Glu Gly Val Phe His Thr
        35                  40                  45

Met Trp His Val Thr Arg Gly Ala Val Leu Met Tyr Gln Gly Lys Arg
    50                  55                  60

Leu Glu Pro Ser Trp Ala Ser Val Lys Lys Asp Leu Ile Ser Tyr Gly
65                  70                  75                  80

Gly Gly Trp Arg Phe Gln Gly Ser Trp Asn Ala Gly Glu Glu Val Gln
                85                  90                  95
```

```
Val Ile Ala Val Glu Pro Gly Lys Asn Pro Lys Asn Val Gln Thr Ala
            100                 105                 110

Pro Gly Thr Phe Lys Thr Pro Glu Gly Glu Val Gly Ala Ile Ala Leu
        115                 120                 125

Asp Phe Lys Pro Gly Thr Ser Gly Ser Pro Ile Val Asn Arg Glu Gly
    130                 135                 140

Lys Ile Val Gly Leu Tyr Gly Asn Gly Val Val Thr Thr Ser Gly Thr
145                 150                 155                 160

Tyr Val Ser Ala Ile Ala Gln Ala Lys Ala Ser Gln Glu Gly Pro Leu
                165                 170                 175

Pro Glu Ile Glu
            180


<210> SEQ ID NO 3
<211> LENGTH: 180
<212> TYPE: PRT
<213> ORGANISM: Dengue virus type 3

<400> SEQUENCE: 3

Ser Gly Val Leu Trp Asp Val Pro Ser Pro Pro Glu Thr Gln Lys Ala
1               5                   10                  15

Glu Leu Glu Glu Gly Val Tyr Arg Ile Lys Gln Gln Gly Ile Phe Gly
            20                  25                  30

Lys Thr Gln Val Gly Val Gly Val Gln Lys Glu Gly Val Phe His Thr
        35                  40                  45

Met Trp His Val Thr Arg Gly Ala Val Leu Thr His Asn Gly Lys Arg
    50                  55                  60

Leu Glu Pro Asn Trp Ala Ser Val Lys Lys Asp Leu Ile Ser Tyr Gly
65                  70                  75                  80

Gly Gly Trp Arg Leu Ser Ala Gln Trp Gln Lys Gly Glu Glu Val Gln
                85                  90                  95

Val Ile Ala Val Glu Pro Gly Lys Asn Pro Lys Asn Phe Gln Thr Thr
            100                 105                 110

Pro Gly Thr Phe Gln Thr Thr Thr Gly Glu Ile Gly Ala Ile Ala Leu
        115                 120                 125

Asp Phe Lys Pro Gly Thr Ser Gly Ser Pro Ile Ile Asn Arg Glu Gly
    130                 135                 140

Lys Val Val Gly Leu Tyr Gly Asn Gly Val Val Thr Lys Asn Gly Gly
145                 150                 155                 160

Tyr Val Ser Gly Ile Ala Gln Thr Asn Ala Glu Pro Asp Gly Pro Thr
                165                 170                 175

Pro Glu Leu Glu
            180


<210> SEQ ID NO 4
<211> LENGTH: 179
<212> TYPE: PRT
<213> ORGANISM: Dengue virus type 4

<400> SEQUENCE: 4

Ser Gly Ala Leu Trp Asp Val Pro Ser Pro Ala Ala Thr Lys Lys Ala
1               5                   10                  15

Ala Leu Ser Glu Gly Val Tyr Arg Ile Met Gln Arg Gly Leu Phe Gly
            20                  25                  30

Lys Thr Gln Val Gly Val Gly Ile His Met Glu Gly Val Phe His Thr
        35                  40                  45
```

Met Trp His Val Thr Arg Gly Ser Val Ile Cys His Glu Thr Gly Arg
50 55 60

Leu Glu Pro Ser Trp Ala Asp Val Arg Asn Asp Met Ile Ser Tyr Gly
65 70 75 80

Gly Gly Trp Arg Leu Gly Asp Lys Trp Asp Lys Glu Glu Asp Val Gln
85 90 95

Val Leu Ala Ile Glu Pro Gly Lys Asn Pro Lys His Val Gln Thr Lys
100 105 110

Pro Gly Leu Phe Lys Thr Leu Thr Gly Glu Ile Gly Ala Val Thr Leu
115 120 125

Asp Phe Lys Pro Gly Thr Ser Gly Ser Pro Ile Ile Asn Arg Lys Gly
130 135 140

Lys Val Ile Gly Leu Tyr Gly Asn Gly Val Val Thr Lys Ser Gly Asp
145 150 155 160

Tyr Val Ser Ala Ile Thr Gln Ala Glu Arg Ile Gly Glu Pro Asp Tyr
165 170 175

Glu Val Asp

<210> SEQ ID NO 5
<211> LENGTH: 180
<212> TYPE: PRT
<213> ORGANISM: West Nile virus

<400> SEQUENCE: 5

Gly Gly Val Leu Trp Asp Thr Pro Ser Pro Lys Glu Tyr Lys Lys Gly
1 5 10 15

Asp Thr Thr Thr Gly Val Tyr Arg Ile Met Thr Arg Gly Leu Leu Gly
20 25 30

Ser Tyr Gln Ala Gly Ala Gly Val Met Val Glu Gly Val Phe His Thr
35 40 45

Leu Trp His Thr Thr Lys Gly Ala Ala Leu Met Ser Gly Glu Gly Arg
50 55 60

Leu Asp Pro Tyr Trp Gly Ser Val Lys Glu Asp Arg Leu Cys Tyr Gly
65 70 75 80

Gly Pro Trp Lys Leu Gln His Lys Trp Asn Gly Gln Asp Glu Val Gln
85 90 95

Met Ile Val Val Glu Pro Gly Lys Asn Val Lys Asn Val Gln Thr Lys
100 105 110

Pro Gly Val Phe Lys Thr Pro Glu Gly Glu Ile Gly Ala Val Thr Leu
115 120 125

Asp Phe Pro Thr Gly Thr Ser Gly Ser Pro Ile Val Asp Lys Asn Gly
130 135 140

Asp Val Ile Gly Leu Tyr Gly Asn Gly Val Ile Met Pro Asn Gly Ser
145 150 155 160

Tyr Ile Ser Ala Ile Val Gln Gly Glu Arg Met Asp Glu Pro Ile Pro
165 170 175

Ala Gly Phe Glu
180

<210> SEQ ID NO 6
<211> LENGTH: 180
<212> TYPE: PRT
<213> ORGANISM: Japanese encephalitis virus

<400> SEQUENCE: 6

```
Gly Gly Val Phe Trp Asp Thr Pro Ser Pro Lys Pro Cys Ser Lys Gly
1               5                   10                  15

Asp Thr Thr Thr Gly Val Tyr Arg Ile Met Ala Arg Gly Ile Leu Gly
            20                  25                  30

Thr Tyr Gln Ala Gly Val Gly Val Met Tyr Glu Asn Val Phe His Thr
        35                  40                  45

Leu Trp His Thr Thr Arg Gly Ala Ala Ile Met Ser Gly Glu Gly Lys
    50                  55                  60

Leu Thr Pro Tyr Trp Gly Ser Val Lys Glu Asp Arg Ile Ala Tyr Gly
65                  70                  75                  80

Gly Pro Trp Arg Phe Asp Arg Lys Trp Asn Gly Thr Asp Asp Val Gln
                85                  90                  95

Val Ile Val Val Glu Pro Gly Lys Ala Ala Val Asn Ile Gln Thr Lys
            100                 105                 110

Pro Gly Val Phe Arg Thr Pro Phe Gly Glu Val Gly Ala Val Ser Leu
        115                 120                 125

Asp Tyr Pro Arg Gly Thr Ser Gly Ser Pro Ile Leu Asp Ser Asn Gly
    130                 135                 140

Asp Ile Ile Gly Leu Tyr Gly Asn Gly Val Glu Leu Gly Asp Gly Ser
145                 150                 155                 160

Tyr Val Ser Ala Ile Val Gln Gly Asp Arg Gln Glu Glu Pro Val Pro
                165                 170                 175

Glu Ala Tyr Thr
            180


<210> SEQ ID NO 7
<211> LENGTH: 180
<212> TYPE: PRT
<213> ORGANISM: St. Louis encephalitis virus

<400> SEQUENCE: 7

Gly Gly Ala Leu Trp Asp Val Pro Ser Pro Lys Val Tyr Pro Lys Cys
1               5                   10                  15

Glu Thr Lys Pro Gly Ile Tyr Arg Ile Met Thr Arg Gly Ile Leu Gly
            20                  25                  30

Thr Phe Gln Ala Gly Val Gly Val Met His Glu Gly Val Phe His Thr
        35                  40                  45

Met Trp His Ala Thr Glu Gly Ala Val Leu Arg Asn Gly Glu Gly Arg
    50                  55                  60

Leu Asp Pro Tyr Ala Gly Asp Val Arg Asn Asp Leu Ile Ser Tyr Gly
65                  70                  75                  80

Gly Pro Trp Lys Leu Ser Ala Thr Trp Asp Gly Thr Glu Glu Val Gln
                85                  90                  95

Met Ile Ala Val Ala Pro Gly Lys Pro Ala Ile Asn Val Gln Thr Thr
            100                 105                 110

Pro Gly Val Phe Lys Thr Pro Leu Gly Thr Ile Gly Ala Val Thr Leu
        115                 120                 125

Asp Phe Pro Lys Gly Thr Ser Gly Ser Pro Ile Ile Asn Lys Lys Gly
    130                 135                 140

Glu Ile Ile Gly Leu Tyr Gly Asn Gly Val Leu Ile Gly Gln Gly Glu
145                 150                 155                 160

Tyr Val Ser Gly Ile Ile Gln Gly Glu Arg Thr Glu Glu Pro Ile Pro
                165                 170                 175

Asp Ala Tyr Asn
            180
```

-continued

<210> SEQ ID NO 8
<211> LENGTH: 180
<212> TYPE: PRT
<213> ORGANISM: Zika virus

<400> SEQUENCE: 8

Ser Gly Ala Leu Trp Asp Val Pro Ala Pro Lys Glu Val Lys Lys Gly
1               5                   10                  15

Glu Thr Thr Asp Gly Val Tyr Arg Val Met Thr Arg Arg Leu Leu Gly
            20                  25                  30

Ser Thr Gln Val Gly Val Gly Val Met Gln Glu Gly Val Phe His Thr
        35                  40                  45

Met Trp His Val Thr Lys Gly Ala Ala Leu Arg Ser Gly Glu Gly Arg
    50                  55                  60

Leu Asp Pro Tyr Trp Gly Asp Val Lys Gln Asp Leu Val Ser Tyr Cys
65                  70                  75                  80

Gly Pro Trp Lys Leu Asp Ala Ala Trp Asp Gly Leu Ser Glu Val Gln
                85                  90                  95

Leu Leu Ala Val Pro Pro Gly Glu Arg Ala Arg Asn Ile Gln Thr Leu
            100                 105                 110

Pro Gly Ile Phe Lys Thr Lys Asp Gly Asp Ile Gly Ala Val Ala Leu
        115                 120                 125

Asp Tyr Pro Ala Gly Thr Ser Gly Ser Pro Ile Leu Asp Lys Cys Gly
    130                 135                 140

Arg Val Ile Gly Leu Tyr Gly Asn Gly Val Val Ile Lys Asn Gly Ser
145                 150                 155                 160

Tyr Val Ser Ala Ile Thr Gln Gly Lys Arg Glu Glu Glu Thr Pro Val
                165                 170                 175

Glu Cys Phe Glu
            180

<210> SEQ ID NO 9
<211> LENGTH: 183
<212> TYPE: PRT
<213> ORGANISM: Yellow fever virus

<400> SEQUENCE: 9

Ser Gly Asp Val Leu Trp Asp Ile Pro Thr Pro Lys Ile Ile Glu Glu
1               5                   10                  15

Cys Glu His Leu Glu Asp Gly Ile Tyr Gly Ile Phe Gln Ser Thr Phe
            20                  25                  30

Leu Gly Ala Ser Gln Arg Gly Val Gly Val Ala Gln Gly Gly Val Phe
        35                  40                  45

His Thr Met Trp His Val Thr Arg Gly Ala Phe Leu Val Arg Asn Gly
    50                  55                  60

Lys Lys Leu Ile Pro Ser Trp Ala Ser Val Lys Glu Asp Leu Val Ala
65                  70                  75                  80

Tyr Gly Gly Ser Trp Lys Leu Glu Gly Arg Trp Asp Gly Glu Glu Glu
                85                  90                  95

Val Gln Leu Ile Ala Ala Val Pro Gly Lys Asn Val Val Asn Val Gln
            100                 105                 110

Thr Lys Pro Ser Leu Phe Lys Val Arg Asn Gly Gly Glu Ile Gly Ala
        115                 120                 125

Val Ala Leu Asp Tyr Pro Ser Gly Thr Ser Gly Ser Pro Ile Val Asn
    130                 135                 140

-continued

```
Arg Asn Gly Glu Val Ile Gly Leu Tyr Gly Asn Gly Ile Leu Val Gly
145                 150                 155                 160

Asp Asn Ser Phe Val Ser Ala Ile Ser Gln Thr Glu Val Lys Glu Glu
                165                 170                 175

Gly Lys Glu Glu Leu Gln Glu
            180


<210> SEQ ID NO 10
<211> LENGTH: 182
<212> TYPE: PRT
<213> ORGANISM: Tick-borne encephalitis virus

<400> SEQUENCE: 10

Ser Asp Leu Val Phe Ser Gly Gln Gly Gly Arg Glu Arg Gly Asp Arg
1               5                   10                  15

Pro Phe Glu Val Lys Asp Gly Val Tyr Arg Ile Phe Ser Pro Gly Leu
            20                  25                  30

Phe Trp Gly Gln Asn Gln Val Gly Val Gly Tyr Gly Ser Lys Gly Val
        35                  40                  45

Leu His Thr Met Trp His Val Thr Arg Gly Ala Ala Leu Ser Ile Asp
    50                  55                  60

Asp Ala Val Ala Gly Pro Tyr Trp Ala Asp Val Arg Glu Asp Val Val
65                  70                  75                  80

Cys Tyr Gly Gly Ala Trp Ser Leu Glu Glu Lys Trp Lys Gly Glu Thr
                85                  90                  95

Val Gln Val His Ala Phe Pro Pro Gly Arg Ala His Glu Val His Gln
            100                 105                 110

Cys Gln Pro Gly Glu Leu Ile Leu Asp Thr Gly Arg Lys Leu Gly Ala
        115                 120                 125

Ile Pro Ile Asp Leu Val Lys Gly Thr Ser Gly Ser Pro Ile Leu Asn
    130                 135                 140

Ala Gln Gly Val Val Val Gly Leu Tyr Gly Asn Gly Leu Lys Thr Asn
145                 150                 155                 160

Glu Thr Tyr Val Ser Ser Ile Ala Gln Gly Glu Ala Glu Lys Ser Arg
                165                 170                 175

Pro Asn Leu Pro Gln Ala
            180


<210> SEQ ID NO 11
<211> LENGTH: 182
<212> TYPE: PRT
<213> ORGANISM: Powassan virus

<400> SEQUENCE: 11

Thr Asp Leu Val Phe Ser Gly Gln Leu Pro Asp Gln Gly Glu Lys Arg
1               5                   10                  15

Ser Phe Asp Ile Lys Glu Gly Val Tyr Arg Ile Tyr Ala Pro Gly Leu
            20                  25                  30

Phe Trp Gly Tyr Arg Gln Ile Gly Val Gly Tyr Gly Thr Lys Gly Val
        35                  40                  45

Leu His Thr Met Trp His Val Thr Arg Gly Ala Ala Leu Ser Val Glu
    50                  55                  60

Gly Ala Thr Ser Gly Pro Tyr Trp Ala Asp Val Arg Glu Asp Val Val
65                  70                  75                  80

Cys Tyr Gly Gly Ala Trp Gly Leu Asp Lys Lys Trp Gly Gly Glu Val
                85                  90                  95
```

Val Gln Val His Ala Phe Pro Pro Asp Ser Gly His Lys Ile His Gln
100 105 110

Cys Gln Pro Gly Lys Leu Asn Leu Glu Gly Gly Arg Val Leu Gly Ala
115 120 125

Ile Pro Ile Asp Leu Pro Arg Gly Thr Ser Gly Ser Pro Ile Ile Asn
130 135 140

Ala Gln Gly Asp Val Leu Gly Leu Tyr Gly Asn Gly Leu Lys Ser Asn
145 150 155 160

Asp Val Tyr Ile Ser Ser Ile Ala Gln Gly Asn Val Glu Lys Ser Arg
165 170 175

Pro Glu Met Pro Leu Ala
180

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
ccgctgccca acacaag 17

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ccactaaygt tcttttgcag acat 24

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
agcctacctt gacaagcagt cagacactca a 31

COMPOUNDS AND METHODS FOR INHIBITING VIRAL REPLICATION AND METHODS OF TREATING AND PREVENTING FLAVIVIRAL INFECTIONS

This application claims benefit of U.S. Provisional Patent Application Ser. No. 63/056,011, filed Jul. 24, 2020, which is hereby incorporated by reference in its entirety.

This invention was made with government support under AI131669, AI133219, AI140491, and AI134568 awarded by the National Institutes of Health. The government has certain rights in the invention.

FIELD

The present disclosure relates to compounds and methods for inhibiting viral activity and viral replication, as well as methods of treating and preventing flaviviral infections.

BACKGROUND

The genus Flavivirus is composed of more than 70 viruses. Many flaviviruses, including the four serotypes of the Dengue virus (DENV1-4), the West Nile virus, and the Zika virus (ZTKV or ZK) cause serious human diseases. Recently, significant ZIKV outbreaks have occurred worldwide. Calvet et al., "Detection and Sequencing of Zika Virus From Amniotic Fluid of Fetuses With Microcephaly in Brazil: A Case Study," *Lancet Infect. Dis.* 16:653-660 (2016); Thomas et al., "Local Transmission of Zika Virus—Puerto Rico, Nov. 23, 2015-Jan. 28, 2016," *MMWR Morb. Mortal Wkly. Rep.* 65:54-158 (2016); Martines et al., "Notes From the Field: Evidence of Zika Virus Infection in Brain and Placental Tissues from Two Congenitally Infected Newborns and Two Fetal Losses—Brazil, 2015," *MMWR Morb. Mortal Wkly. Rep.* 65:159-160 (2016); Rodriguez-Morales, A. J., "Zika and Microcephaly in Latin America: An Emerging Threat for Pregnant Travelers?," *Travel Med. Infect. Dis.* 14:5-6 (2016); and Li et al., "Zika Virus Disrupts Neural Progenitor Development and Leads to Microcephaly in Mice," *Cell Stem Cell* (2016). ZIKV is transmitted to humans primarily through bites from infected *Aedes* species mosquitoes, but may also be transferred prenatally or through sexual activities or blood transfusions. Patino-Barbosa et al., "Zika: Another Sexually Transmitted Infection?," *Sex. Transm. Infect.* 91:359 (2015); Musso et al., "Potential Sexual Transmission of Zika Virus," *Emerg. Infect. Dis.* 21:359-361 (2015); Musso et al., "Potential for Zika Virus Transmission Through Blood Transfusion Demonstrated During an Outbreak in French Polynesia, November 2013 to February 2014," *Euro. Surveill.* 19 (2014); and Foy et al., "Probable Non-Vector-Borne Transmission of Zika Virus, Colorado, USA," *Emerg. Infect. Dis.* 17:880-882 (2011). ZIKV infection is associated with devastating diseases, including Guillain-Barré syndrome, a rare neurological syndrome, and congenital Zika syndrome, which is manifested by microcephaly, brain abnormalities, and other central nervous system malformations. Calvet et al., "Detection and Sequencing of Zika Virus From Amniotic Fluid of Fetuses With Microcephaly in Brazil: A Case Study," *Lancet Infect. Dis.* 16:653-660 (2016); Thomas et al., "Local Transmission of Zika Virus—Puerto Rico, Nov. 23, 2015-Jan. 28, 2016," *MMWR Morb. Mortal Wkly. Rep.* 65:54-158 (2016); Martines et al., "Notes From the Field: Evidence of Zika Virus Infection in Brain and Placental Tissues from Two Congenitally Infected Newborns and Two Fetal Losses—Brazil, 2015," *MMWR Morb. Mortal Wkly. Rep.* 65:159-160 (2016); Rodriguez-Morales, A. J., "Zika and Microcephaly in Latin America: An Emerging Threat for Pregnant Travelers?," *Travel Med. Infect. Dis.* 14:5-6 (2016); and Li et al., "Zika Virus Disrupts Neural Progenitor Development and Leads to Microcephaly in Mice," *Cell Stem Cell* (2016). In addition, ZIKV persists in neuronal and/or reproductive tissues of animals for up to 60 days after viral infection, leading to severe damage. Duggal et al., "Frequent Zika Virus Sexual Transmission and Prolonged Viral RNA Shedding in an Immunodeficient Mouse Model," *Cell Rep.* 18:1751-1760 (2017); Hirsch et al., "Zika Virus Infection of Rhesus Macaques Leads to Viral Persistence in Multiple Tissues," *PLoS Pathog.* 13:e1006219 (2017); Govero et al., "Zika Virus Infection Damages the Testes in Mice," *Nature* 540:438-442 (2016). Currently there is neither a safe and effective vaccine nor a specific therapy for ZIKV. Although a DENV vaccine is recently approved, it is effective in children between 9 and 16-year-old, and posts increased risk for naïve children due to antibody-dependent enhancement. Aguiar et al., "The Impact of the Newly Licensed Dengue Vaccine in Endemic Countries," *PLoS Negl. Trop. Dis.* 10:e0005179 (2016). Therefore, there is an unmet medical need to develop direct antivirals against flaviviruses.

The flavivirus genome encodes a single open reading frame, from which a polyprotein precursor is expressed. Brecher et al., "The Flavivirus Protease as a Target for Drug Discovery," *Virol. Sin.* 28:326-336 (2013); Lindenbach et al., "Flaviviridae: The virus and Their Replication," (Lippincott William & Wilkins (2001); and Liu et al., "Flavivirus RNA Cap Methyltransferase: Structure, Function, and Inhibition," *Front. Biol.* 5:286-303 (2010). The polyprotein precursor is post-translationally processed into 10 mature proteins, including three structural and seven non-structural proteins, by viral and host proteases in a sequential manner. Brecher et al., "The Flavivirus Protease as a Target for Drug Discovery," *Virol. Sin.* 28:326-336 (2013) and Lindenbach et al., "Flaviviridae: The virus and Their Replication," (Lippincott William & Wilkins (2001). The viral protease is a heterocomplex composed of viral NS3 protein and its viral co-factor NS2B. Brecher et al., "The Flavivirus Protease as a Target for Drug Discovery," *Virol. Sin.* 28:326-336 (2013). The viral protease has been considered a highly promising drug target. Brecher et al., "The Flavivirus Protease as a Target for Drug Discovery," *Virol. Sin.* 28:326-336 (2013); Kang et al., "Zika Virus Protease: An Antiviral Drug Target," *Trends Microbiol.* 25:797-808 (2017); Nitsche, C., "Proteases From Dengue, West Nile and Zika Viruses as Drug Targets," *Biophys. Rev.* 11:157-165 (2019); and Noble et al., "Strategies for Development of Dengue Virus Inhibitors," *Antiviral research* 85:450-462 (2010). Various strategies have been used to develop protease inhibitors. The majority of efforts have been focused on the viral protease active site (Aguiar et al., "The Impact of the Newly Licensed Dengue Vaccine in Endemic Countries," *PLoS Negl. Trop. Dis.* 10:e0005179 (2016); Liu et al., "Flavivirus RNA Cap Methyltransferase: Structure, Function, and Inhibition," *Front. Biol.* 5:286-303 (2010); Kang et al., "Zika Virus Protease: An Antiviral Drug Target," *Trends Microbiol.* 25:797-808 (2017); and Nitsche, C., "Proteases From Dengue, West Nile and Zika Viruses as Drug Targets," Biophys. Rev. 11:157-165 (2019)), but with limited success in finding inhibitors with in vivo efficacy. Yuan et al., "Structure-based Discovery of Clinically Approved Drugs as Zika Virus NS2B-NS3 Protease Inhibitors That Potently Inhibit Zika Virus Infection In Vitro and In Vivo," *Antiviral Res.* 145:33-43 (2017). Recently, alternative strategies to target the NS2B-NS3 interaction (Li et al., "Existing Drugs as Broad-Spectrum and Potent Inhibitors for Zika Virus by Targeting NS2B-NS3 Interaction," *Cell Res.* 27:1046-1064 (2017) and Li et al., "Erythrosin B is a Potent and Broad-Spectrum Orthosteric Inhibitor of the Flavivirus NS2B-NS3 Protease," *Antiviral Res.* 150:217-225 (2018)) and allosteric sites (Brecher et al., "A Conformational Switch High-Throughput Screening Assay and Allosteric Inhibition of the Flavivirus NS2B-NS3 Protease," *PLoS Pathog.* 13:e1006411 (2017); Yao et al., "Discovery, X-ray Crystallography and Antiviral Activity of Allosteric Inhibitors of Flavivirus NS2B-NS3 Protease," *J. Am. Chem. Soc.* 141:6832-6836 (2019); and Shiryaev et al., "Characterization of the Zika Virus Two-component NS2B-NS3 Protease and Structure-Assisted Identification of Allosteric Small-Molecule Antagonists," *Antiviral Res.* 143:218-229 (2017) have led to identification of potent protease inhibitors with in vivo efficacy against Zika virus.

Previously, a split luciferase complementation (SLC)-based high throughput screening strategy was developed to identify inhibitors targeting the NS2B-NS3 interface of DENV2 (DN2). Li et al., "Existing Drugs as Broad-Spectrum and Potent Inhibitors for Zika Virus by Targeting NS2B-NS3 Interaction," *Cell Res.* 27:1046-1064 (2017). Niclosamide was found to be a broad-spectrum inhibitor for flaviviruses by targeting the interface between viral protease NS3 and its co-factor NS2B, leading to accumulation of non-functional viral polyprotein precursor. Id. In addition, niclosamide was found to interfere with virus entry (Mazzon et al., "Identification of Broad-Spectrum Antiviral Compounds by Targeting Viral Entry," *Viruses* 11 (2019)) and endosomal acidification. Kao et al., "The Antiparasitic Drug Niclosamide Inhibits Dengue Virus Infection by Interfering With Endosomal Acidification Independent of mTOR," *PLoS Negl. Trop. Dis.* 12:e0006715 (2018). Moreover, niclosamide was found as a broad-spectrum antiviral against multiple viruses including SARS Cov-2, the causing agent of current COVID-19 pandemic. Xu et al., "Broad Spectrum Antiviral Agent Niclosamide and Its Therapeutic Potential," *ACS Infect Dis* (2020). Unfortunately, niclosamide did not show appreciable in vivo antiviral efficacy towards ZIKV, possibly due to its poor pharmacokinetic properties. Mazzon et al., "Identification of Broad-Spectrum Antiviral Compounds by Targeting Viral Entry," *Viruses* 11 (2019) and Fan et al., "Contributions of Hepatic and Intestinal Metabolism to the Disposition of Niclosamide, a Repurposed Drug with Poor Bioavailability," *Drug Metab. Dispos.* 47:756-763 (2019).

The present disclosure is directed to overcoming these and other deficiencies in the art.

SUMMARY

A first aspect relates to a compound of the formula (I) or a pharmaceutically acceptable salt thereof (I)

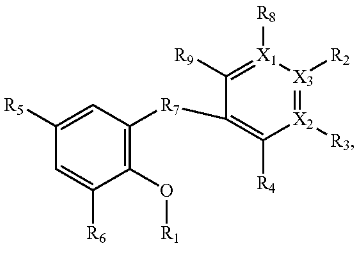

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_7$ is amide, wherein the amide can be optionally substituted with aryl, heterocyclyl, hydrogen, or oxygen;

$R_8$ is hydrogen, halogen, or trihalomethane;

$R_9$ is halogen or hydrogen;

$X_1$, $X_2$, and $X_3$ are independently selected from CH and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_7$ is —C═ONH—, $R_8$ is hydrogen, and $R_9$ is hydrogen.

A second aspect relates to a method of inhibiting viral replication. The method includes contacting one or more cells that have been infected with a virus with an effective amount of a compound of formula (I) or a pharmaceutically acceptable salt thereof (I)

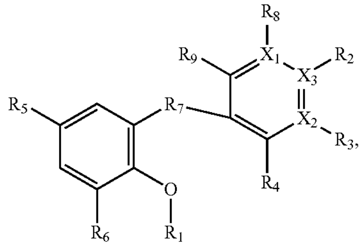

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_7$ is amide, wherein the amide can be optionally substituted with aryl, heterocyclyl, hydrogen, or oxygen;

$R_8$ is hydrogen, halogen, or trihalomethane;

$R_9$ is halogen or hydrogen;

$X_1$, $X_2$, and $X_3$ are independently selected from CH and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_7$ is —C═ONH—, $R_8$ is hydrogen, and $R_9$ is hydrogen; and wherein the virus comprises a flavivirus.

A third aspect relates to a method of treating and/or preventing a flavivirus infection and/or a condition resulting from a flavivirus infection. The method includes administering an effective amount of a compound of formula (I) or a pharmaceutically acceptable salt thereof (I)

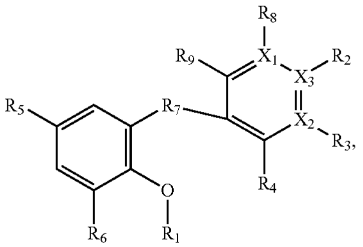

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_7$ is amide, wherein the amide can be optionally substituted with aryl, heterocyclyl, hydrogen, or oxygen;

$R_8$ is hydrogen, halogen, or trihalomethane;

$R_9$ is halogen or hydrogen;

$X_1$, $X_2$, and $X_3$ are independently selected from CH and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_7$ is —C═ONH—, $R_8$ is hydrogen, and $R_9$ is hydrogen, under conditions effective to treat and/or prevent a flavivirus infection and/or a condition resulting from a flavivirus infection.

A fourth aspect relates to a method of inhibiting viral replication. The method includes contacting one or more cells that have been infected with a virus with an effective amount of a compound of formulae (Ia)-(Ip):

(Ia)

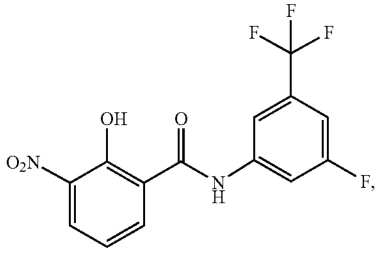

-continued (Ib)

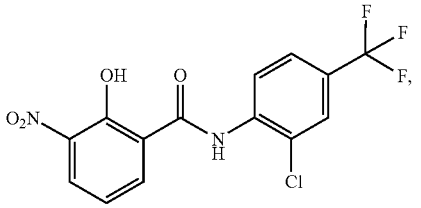

(Ic)

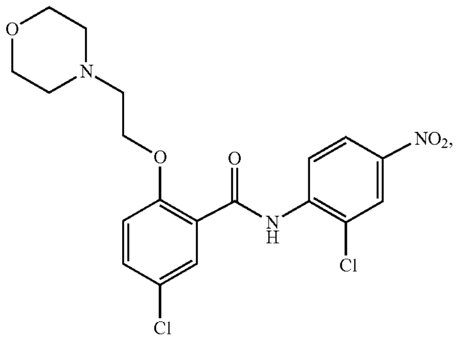

(Id)

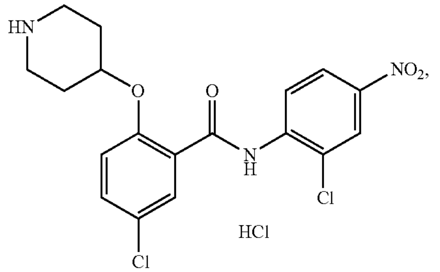

(Ie)

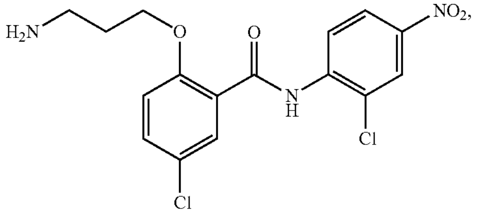

(If)

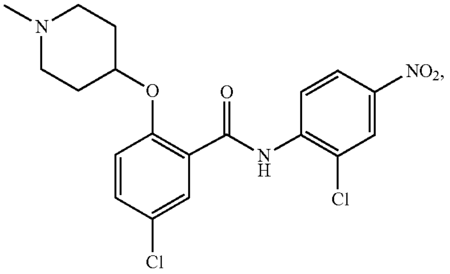

(Ig)

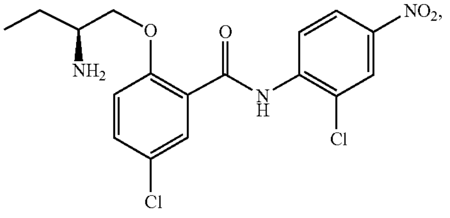

-continued (Ih)

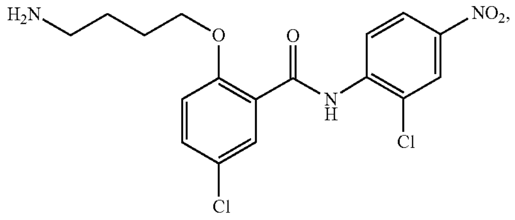

(Ii)

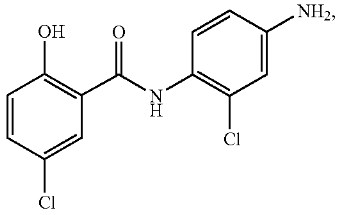

(Ij)

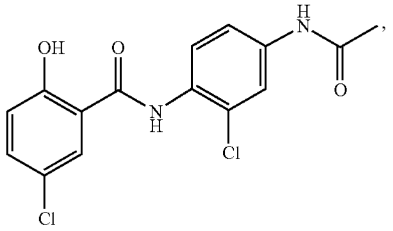

(Ik)

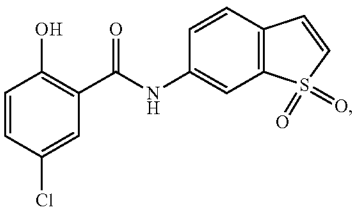

(Il)

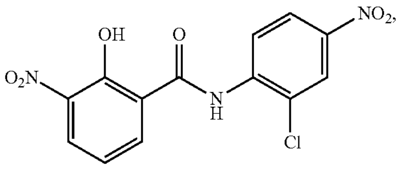

(Im)

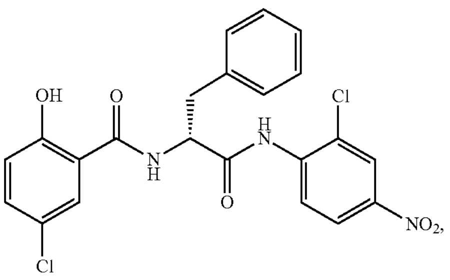

(In)

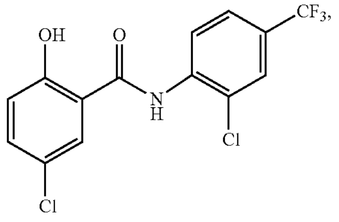

-continued (Io)

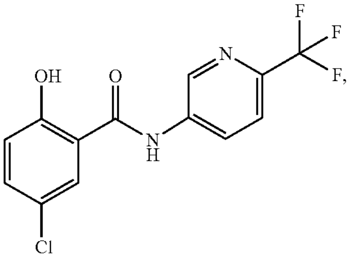

or (Ip)

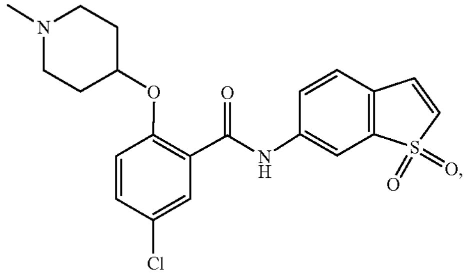

or a pharmaceutically acceptable salt thereof, wherein the virus comprises a flavivirus.

Flaviviruses causes significant human disease. Recent outbreaks of the Zika virus highlight the need to develop effective therapies for this class of viruses. Previously, niclosamide was identified as a broad-spectrum inhibitor for flaviviruses by targeting the interface between viral protease NS3 and its cofactor NS2B. In the present disclosure, a small library of niclosamide derivatives was screened and a new analogue with improved pharmacokinetic properties was identified. Compound JMX0207 showed improved efficacy in inhibition of the molecular interaction between NS3 and NS2B, better inhibition of viral protease function, and enhanced antiviral efficacy in cell-based antiviral assay. The derivative also significantly reduced Zika virus infection on 3D mini-brain organoids derived from pluripotent neural stem cells. Intriguingly, the compound significantly reduced viremia in a ZIKV animal model. In summary, a niclosamide derivative, JMX0207, was identified which shows improved pharmacokinetics and efficacy against Zika virus both in vitro and in vivo.

BRIEF DESCRIPTION OF THE DRAWINGS

FIG. 1A shows dose-dependent inhibition of SLC upon binding of NLuc-NS2B$_{49-66}$ to GST-CLuc-NS3 by JMX0207. N=3. FIG. 1B shows dose-response inhibitions of the DENV2 His-NS2B/His-MBP-NS3 protease activity by JMX0207. N=3. In both FIG. 1A and FIG. 1, DMSO control was set as 100%. The values represent means±standard deviation (S.D.) in all panels.

FIG. 2A shows dose-dependent inhibition of DENV2 infectivity by JMX0207. N=3. FIG. 2B shows cell viability assay. A549 cells were incubated with various concentrations of JMX0207 and then assayed for viability at 48 hrs post-incubation. N=3. Error bars in both panels represent the standard deviations at each concentration.

FIG. 3A shows dose-dependent inhibition of ZIKV infectivity. N=3. FIG. 3B shows qRT-PCR analysis of inhibition of viral RNA from ZIKV-infected A549 cells by JMX0207. N=3. Error bars in panels FIGS. 3A and 3B represent the standard deviations at each concentration. FIG. 3C shows immunofluorescence assay of inhibition of viral protein production by JMX0207, using pan-flavivirus anti-E 4G2 antibody (green) (ATCC).

FIG. 4A shows immunofluorescence assay (IFA) of inhibition of viral protein expression in human neural progenitor cells by JMX0207, using pan-flavivirus anti-E 4G2 antibody (green) (ATCC). Nuclei (blue) was stained in all IFA assays by the Hoechst stain solution. FIG. 4B shows qRT-PCR analyses of inhibition of viral RNA from ZIKV-infected human neural progenitor cell (HNPC) by JMX0207. N=3. FIG. 4C shows ZIKV organoid infected with ZIKV-Venus. The 3D organoids were infected with PBS (Mock), or ZIKV untreated (DMSO), or ZIKV treated with JMX0207, or Mock treated with JMX0207. Upper panel, bright field image of intact organoids. Lower panel, Venus fluorescence image (excitation 515 nm, emission 528 nm) of the intact 3D organoids. FIG. 4D shows forebrain regional specification of organoids. Organoids were stained positive for forebrain identity markers PAX6 (green, upper panel), FOXG1 (green, lower panel) and SOX2 (Red (Magenta after merge with DAPI (Blue)), upper panel) at 20 days. The sections were stained positive for general neuronal marker TUJI (cyan, upper and lower panels) and were negative for SOX10 (Red, lower panel). DAPI-merged data were shown. Nuclei (DAPI, Blue); scale bar 200 m. FIG. 4E shows slices of organoid infected with ZIKV PRVABC59. The 3D organoids were infected with PBS (Mock), or ZIKV untreated (DMSO), or ZIKV treated with JMX0207. Upper panel, IFA using anti-E 4G2 antibody (green); blue, DAPI. Lower panel, details of signature rosette region of the 3D organoids (Mock) or infected region (DMSO/ZIKV and JMX0207/ZIKV). Red: Pax6. FIG. 4F shows ZIKV production from the 3D organoids at 5 dpi. Culture supernatants were collected, and virus production was quantified by PFU assay. N=3. Error bars in panels FIGS. 4B and 4F represent the standard deviations at each concentration.

FIG. 5A is a pharmacokinetic study of niclosamide and JMX0207. Adult female B6 mice were given a single oral dose of either niclosamide or JMX0207 at 40 mg/kg. Plasma was obtained at various times after dosing. Both niclosamide and JMX0207 were extracted from the plasma and then analyzed by LC-MS/MS as described in the Methods. N=4. FIG. 5B is a pharmacokinetic study of JMX0207 at different doses. N=4-5. The values in panels FIGS. 5A and 5B represent means S.D. In FIG. 5C, Viremia was detected by a plaque forming unit (PFU) assay on day 3 post-infection of ZIKV with a dose of $1.7\times10^5$ PFU/mouse in four-week-old A129 mice, which were treated with vehicle or JMX0207 though oral gavage. Difference between JMX0207 (N=10) or vehicle (N=10) treatment was analyzed by using the unpaired, two-tailed t-test. *, P=0.0081. Error bars represent data range of median with 95% confidence interval.

FIG. 6A shows time of addition. JMX0207 (0.75 μM) was added at indicated time points post-infection. Viral titers were quantified using plaque forming assay 48 hrs post-infection. DMSO was added to control. N=3. *, p<0.001. FIG. 6B shows dose-dependent inhibition of DENV2 replicon by niclosamide and JMX0207. N=3. FIG. 6**C shows WB analysis of dose response inhibition of ZIKV NS3 production by JMX0207 treatment (left). Right, Band intensities of PP and NS3 normalized to the GAPDH control (N=3). Pre-seeded A549 cells in 6-well plate were treated with JMX0207 or DMSO control and infected with ZIKV with MOI of 0.1, as described previously. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. At 48 hrs post-infection, cells were washed, harvested, and protected by protease inhibitor cocktail prior to lysis by SDS-PAGE loading buffer. Upon incubation at 95° C. for 10 min, sample was subjected to Western blot analysis with anti-ZIKV NS3 (GTX133309, GeneTex, Inc.) and anti-GAPDH (CB1001, EMD Millipore) as primary antibodies. Error bars in all panels represent the standard deviations at each condition.

FIG. 7A shows predicted docking pose of JMX0207 (magenta) docking into NS3pro of DENV2 (PDB Code: 2FOM). NS3pro is in blue ribbon representation and binding site key interaction residues are highlighted in stick presentation. π cation and π stacking are shown as cyan dotted lines, H-bond in purple and salt bridge in blue. FIG. 7B shows predicted binding pose of Niclosamide (green) docked into NS3pro of DENV2. H-bond is shown as purple dotted lines. FIG. 7C shows JMX0207 and Niclosamide superimposed at the predicted binding site, in surface representation. JMX0207 is shown as magenta sticks and Niclosamide in green. FIG. 7D shows representative SPR analysis of JMX0207 binding to the MBP-NS3 protease wild-type and mutant L58A.

FIG. 8 shows a sequence alignment for DENV2 (SEQ ID NO: 1), DENV1 (SEQ ID NO: 2), DENV3 (SEQ ID NO: 3), DENV4 (SEQ ID NO: 4), WNV (SEQ ID NO: 5), JEV (SEQ ID NO: 6), SLEV (SEQ ID NO: 7), ZIKV (SEQ ID NO: 8), YFV (SEQ ID NO: 9), TBEV (SEQ ID NO: 10), POWV (SEQ ID NO: 11), and a consensus sequence.

Figures 1A, 1B:
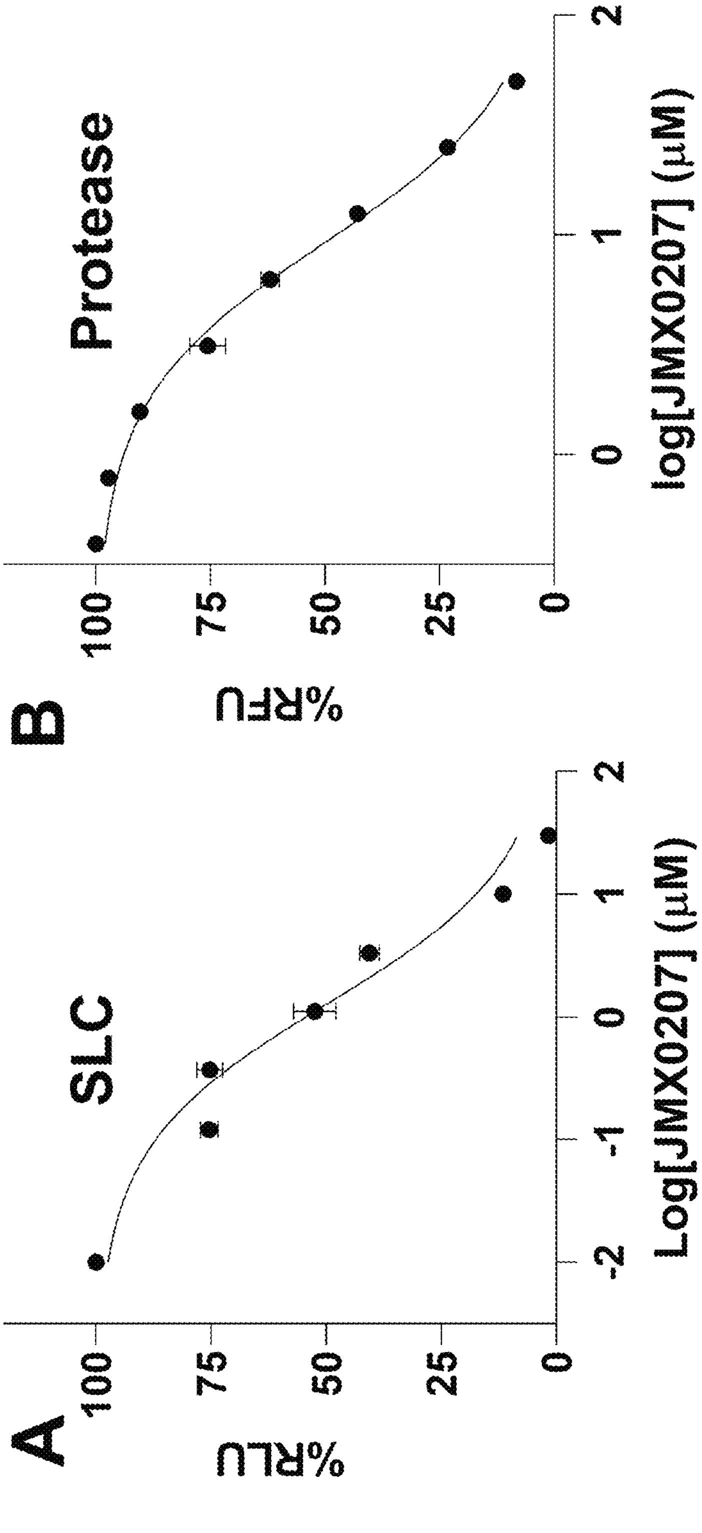
FIGS. 1A-1B show inhibition of the NS2B-NS3 interactions and protease activity.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

DETAILED DESCRIPTION

A first aspect relates to a compound of the formula (I) or a pharmaceutically acceptable salt thereof (I)

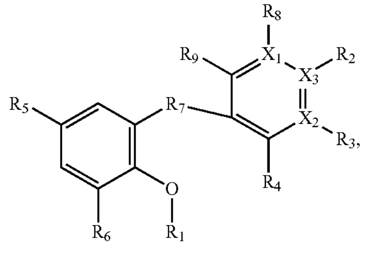

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_7$ is amide, wherein the amide can be optionally substituted with aryl, heterocyclyl, hydrogen, or oxygen;

$R_8$ is hydrogen, halogen, or trihalomethane;

$R_9$ is halogen or hydrogen;

$X_1$, $X_2$, and $X_3$ are independently selected from CH and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_7$ is —C═ONH—, $R_8$ is hydrogen, and $R_9$ is hydrogen.

In one embodiment, in the compound of formula (I), $R_3$ is fluorine or hydrogen. In another embodiment, in the compound of formula (I), $R_4$ is chlorine or hydrogen. In another embodiment, in the compound of formula (I), $R_5$ is chlorine.

In one embodiment, in the compound of formula (I), when $R_2$ is nitrogen oxide, $R_2$ is selected from the group consisting of $NO_2$, NO, $N_2O$, and $N_2O_5$. In another embodiment, in the compound of formula (I), when $R_6$ is nitrogen oxide, $R_6$ is selected from the group consisting of $NO_2$, NO, $N_2O$, and $N_2O_5$. In one embodiment, $R_8$ is trifluoromethane or hydrogen.

In one embodiment, the compound of formula (I) is the compound of formulae (Ia) or (Ib):

(Ia)

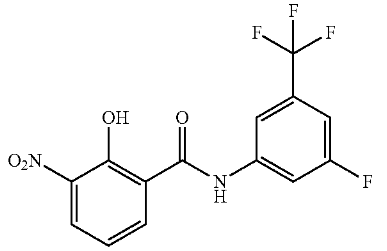

(Ib)

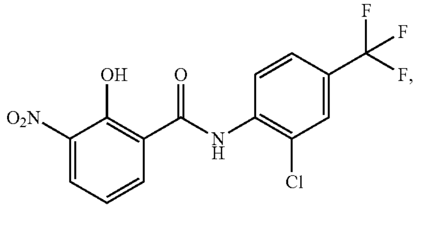

or a pharmaceutically acceptable salt thereof.

It is to be appreciated that certain aspects, modes, embodiments, variations, and features of the present disclosure are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this disclosure belongs.

As used herein, the term "about" means that the numerical value is approximate and small variations would not significantly affect the practice of the disclosed embodiments. Where a numerical limitation is used, unless indicated otherwise by the context, "about" means the numerical value can vary by ±1 or +10%, or any point therein, and remain within the scope of the disclosed embodiments.

Where a range of values is described, it should be understood that intervening values, unless the context clearly dictates otherwise, between the upper and lower limit of that range and any other stated or intervening value in other stated ranges, may be used in the embodiments described herein.

As used herein, the terms "subject", "individual", or "patient," are used interchangeably, and mean any animal, including mammals, such as mice, rats, other rodents, rabbits, dogs, cats, swine, cattle, sheep, horses, or primates, such as humans.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable sub-combination.

As used herein, any "R" group(s) represents substituents that may be attached to an indicated atom. An R group may be substituted or unsubstituted. If two R groups are described as "together with the atoms to which they are attached" forming a ring or ring system, it means that the collective unit of the atoms, intervening bonds and the two R groups are the recited ring.

$C_1$ to $C_{23}$ hydrocarbon includes alkyl, cycloalkyl, polycycloalkyl, alkenyl, alkynyl, aryl, and combinations thereof. Examples include benzyl, phenethyl, propargyl, allyl, cyclohexylmethyl, adamantyl, camphoryl, and naphthylethyl. Hydrocarbon refers to any substituent included of hydrogen and carbon as the only elemental constituents.

The term "alkyl" includes an aliphatic hydrocarbon group which may be straight or branched having about 1 to about 23 carbon atoms in the chain. For example, straight or branched carbon chain could have 1 to 10 carbon atoms or 1 to 6 carbon atoms. Branched means that one or more lower alkyl groups such as methyl, ethyl, or propyl are attached to a linear alkyl chain. Alkyl includes a hydrocarbon that is fully saturated (i.e., contains no double or triple bonds) and combinations thereof (e.g., 1 to 10 carbon atoms, such as 1 to 6 carbon atoms). Examples of alkyl groups include but are not limited to methyl, ethyl, propyl, n-propyl, isopropyl, butyl, isobutyl, n-butyl, s-butyl, t-butyl, n-pentyl, and 3-pentyl. An alkyl group may have between 1 to about 23 carbon atoms (whenever it appears herein, a numerical range such as "1 to 23" refers to each integer in the given range; e.g., "1 to 23 carbon atoms" means that the alkyl group may consist of 1 carbon atom, 2 carbon atoms, 3 carbon atoms, 4 carbon atoms, 5 carbon atoms, etc., and up to and including 23 carbon atoms, although the present disclosure also covers the occurrence of the term "alkyl" where no numerical range is designated). For example, "$C_1$-$C_6$ alkyl" indicates that there are between one and six carbon atoms in the alkyl chain (i.e., the alkyl chain is selected from the group consisting of methyl, ethyl, propyl, iso-propyl, n-butyl, iso-butyl, sec-butyl, and t-butyl).

As described herein, "alkenyl" refers to a straight or branched hydrocarbon chain containing one or more double bonds. An alkenyl group may have about 2 to about 23 carbon atoms, although the present description also covers the occurrence of the term "alkenyl" where no numerical range is designated. The alkenyl group may also be a medium size alkenyl having 2 to 9 carbon atoms. The alkenyl group could also be a lower alkenyl having between 2 and 6 carbon atoms. For example, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups may include, but are not limited to, ethenyl, propenyl, butenyl, pentenyl, and hexenyl.

As described herein, "alkynyl" includes a straight or branched hydrocarbon chain containing one or more triple bonds. An alkynyl group may have between about 2 and about 23 carbon atoms, although the present description also includes the occurrence of the term "alkynyl" where no numerical range is designated. As an example, "$C_2$-$C_6$ alkynyl" indicates between two and six carbon atoms in the alkynyl chain (i.e., the alkynyl chain may be selected from the group consisting of ethynyl, propyn-1-yl, propyn-2-yl, butyn-1-yl, butyn-3-yl, butyn-4-yl, and 2-butynyl). Typical alkynyl groups may include, but are not limited to, ethynyl, propynyl, butynyl, pentynyl, and hexynyl, and the like.

As described herein, "heteroalkyl" may include a straight or branched hydrocarbon chain containing one or more heteroatoms, that is, an element other than carbon, including but not limited to, nitrogen, oxygen, and sulfur, in the chain backbone. A heteroalkyl group may have between 1 and 20 carbon atoms, although the present disclosure also includes the occurrence of the term "heteroalkyl" where no numerical range is designated. For example, "$C_4$-$C_6$ heteroalkyl" may indicate that there are between four and six carbon atoms in the heteroalkyl chain and additionally one or more heteroatoms in the backbone of the chain.

Aromatic as described herein refers to a ring or ring system having a conjugated pi electron system and includes both carbocyclic aromatic (e.g., phenyl) and heterocyclic aromatic groups (e.g., pyridine). Aromatics may include monocyclic or fused-ring polycyclic (i.e., rings which share adjacent pairs of atoms) groups provided the entire ring system is aromatic.

"Aryl" as described herein includes an aromatic ring or ring system (e.g., two or more fused rings that share two adjacent carbon atoms) containing only carbon in the ring backbone. The present disclosure also includes the occurrence of the term "aryl" where no numerical range is designated. In one embodiment, the aryl group has between 6 and 10 carbon atoms. An aryl group may be designated as "$C_6$-$C_{10}$ aryl" for example. Representative aryl groups include, but are not limited to, phenyl, naphthyl, azulenyl, and anthracenyl.

An "aralkyl" or "arylalkyl" as described herein may include an aryl group connected, as a substituent, via an alkylene group, such as for example $C_7$-$C_{14}$ aralkyl and the like, including but not limited to benzyl, 2-phenylethyl, 3-phenylpropyl, and naphthylalkyl.

The term "heteroaryl" includes an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "heteroaryl." The heteroaryl group may have between 5-18 ring members (i.e., the number of atoms making up the ring backbone, including carbon atoms and heteroatoms), although the present disclosure also includes the occurrence of the term "heteroaryl" where no numerical range is designated. Preferred heteroaryls contain between about 5 to 10 ring atoms, or between about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include thienyl, phthalazinyl, pyridinyl, benzoxazolyl, benzothienyl, pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-15 a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

A "heteroaralkyl" or "heteroarylalkyl" refers to a heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl.

Unless otherwise specified, the term "carbocycle" is intended to include ring systems in which the ring atoms are all carbon but of any oxidation state. When the carbocyclyl is a ring system, two or more rings may be joined together in a fused, bridged, or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, and the present use of the term "carbocyclyl" also includes when no numerical range is designated. Thus ($C_3$-$C_{12}$) carbocycle, for example, refers to both non-aromatic and aromatic systems, including such systems as cyclopropane, benzene, and cyclohexene. Carbocycle, if not otherwise limited, refers to monocycles, bicycles, and polycycles.

As used herein, "cycloalkyl" means a fully saturated carbocyclyl ring or ring system. Cycloalkyl is a subset of hydrocarbon and includes cyclic hydrocarbon groups of from 3 to 8 carbon atoms. Examples of cycloalkyl groups include c-propyl, c-butyl, c-pentyl, and norbornyl (e.g., cyclopropyl, cyclobutyl, cyclopentyl, and cyclohexyl).

As used herein, the term "$C_1$-$C_{23}$" includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, and $C_{23}$, and a range defined by any of the two numbers. For example, $C_1$-$C_{23}$ alkyl includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, and $C_{23}$ alkyl, $C_1$-$C_{23}$ alkyl, $C_1$-$C_{20}$ alkyl, $C_1$-$C_{15}$ alkyl, $C_1$-$C_{10}$ alkyl, $C_1$-$C_6$ alkyl, etc. Similarly, $C_2$-$C_{23}$ alkenyl includes $C_2$, $C_3$, $C_4$, $C_5$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, and $C_{23}$ alkenyl, $C_2$-$C_{23}$ alkenyl, $C_2$-$C_{20}$ alkenyl, $C_2$-$C_{15}$ alkenyl, $C_2$-$C_{10}$ alkenyl, $C_2$-$C_6$ alkenyl, etc.; and $C_2$-$C_{23}$ alkynyl includes $C_2$, $C_3$, $C_4$, $C_5$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, and $C_{23}$ alkynyl, $C_2$-$C_{23}$ alkynyl, $C_2$-$C_{20}$ alkynyl, $C_2$-$C_{15}$ alkynyl, $C_2$-$C_{10}$ alkynyl, $C_2$-$C_6$ alkynyl, etc. $C_3$-$C_5$ cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl. As used herein, the term "$C_1$-$C_6$" includes $C_1$, $C_2$, $C_3$, $C_4$, $C_5$, and $C_6$, and a range defined by any of the two numbers $C_1$-$C_6$.

As used herein, "heterocyclyl" or "heterocycle" refers to a stable 3- to 18-membered ring (radical) which consists of carbon atoms and from one to five heteroatoms selected from the group consisting of nitrogen, oxygen, and sulfur. For purposes of this disclosure, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the occurrence of the term "heterocyclyl" where no numerical range is designated is included. Examples of such heterocycles include, without limitation, acridinyl, carbazolyl, imidazolinyl, oxepanyl, thiepanyl, dioxopiperazinyl, pyrrolidonyl, pyrrolidionyl, oxiranyl, azepinyl, azocanyl, pyranyl dioxolanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, thiamorpholinyl sulfone, and tetrahydroquinoline. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "halogen" or "halo" as used herein, may include any one of the radio-stable atoms of column 7 of the Periodic Table of the Elements, e.g., fluorine, chlorine, bromine, or iodine. In one embodiment, halogen may be a fluorine or chlorine atom.

The term "trihalomethane" (THM) includes for example chemical compounds in which three of the four hydrogen atoms of methane ($CH_4$) are replaced by halogen atoms. Trihalomethanes as described herein that have all the same halogen atoms are called haloforms. Examples of trihalomethanes as described herein include but are not limited to trifluoromethane, chlorodifluoromethane, trichloromethane, bromodichloromethane, dibromochloromethane, tribromomethane, and triiodomethane. In one embodiment, the trihalomethane is trifluoromethane.

Basic addition salts can be prepared by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term amide, as described herein, refers to non-toxic amides derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

As described herein, the term nitrogen oxide includes nitrogen- and oxide-containing compounds, for example, $NO_2$, NO, $N_2O$, and $N_2O_5$. The term "nitro" as used interchangeably herein to describe nitrogen- and oxide-containing compounds, may include, for example, a $-NO_2$ group.

The term "substituted" or "substitution" of an atom means that one or more hydrogen on the designated atom is replaced with a selection from the indicated group, provided that the designated atom's normal valency is not exceeded. As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents. Wherever a group is described as "optionally substituted" that group may be substituted with the above substituents.

"Unsubstituted" atoms bear all of the hydrogen atoms dictated by their valency. When a substituent is keto (i.e., $=O$), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture.

The term "hydroxy" as used herein includes a —OH group.

The compounds described herein may contain asymmetric centers and may thus give rise to enantiomers, diastereomers, and other stereoisomeric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The compounds described herein may possess one or more centers of chirality. Various examples of each of such compounds may differ from one another by nature of their stereochemistry at one or more chiral center. A given compound may therefore exist in a stereochemically pure state, consisting of a single stereoisomer, or include a racemic mixture of different enantiomers that possess different stereochemistry at one or more chiral centers from one another. Notwithstanding any chemical identities disclosed herein, also included within the present disclosure are compounds which may include a racemic mixture of various stereoisomers of the compounds described herein or may include isolates of a given stereoisomer of a given compound, identical to or different from any particular stereoisomer specifically identified herein.

Enantiomerically pure means greater than 80 e.e., and preferably greater than 90 e.e. For the purpose of the present disclosure, a "pure" or "substantially pure" stereoisomer is intended to mean that the stereoisomer is at least 95% of the configuration shown and 5% or less of other stereoisomers, or at least 97% of the configuration shown and 3% or less of other stereoisomers, or at least 99% of the configuration shown and 1% or less of other stereoisomers.

A second aspect relates to a method of inhibiting viral replication. The method includes contacting one or more cells that have been infected with a virus with an effective amount of a compound of formula (I) or a pharmaceutically acceptable salt thereof (I)

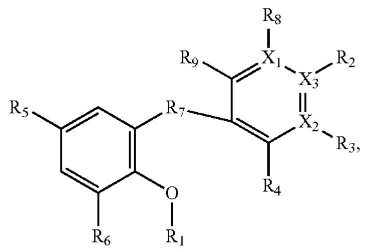

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_7$ is amide, wherein the amide can be optionally substituted with aryl, heterocyclyl, hydrogen, or oxygen;

$R_8$ is hydrogen, halogen, or trihalomethane;

$R_9$ is halogen or hydrogen;

$X_1$, $X_2$, and $X_3$ are independently selected from CH and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_7$ is —C=ONH—, $R_8$ is hydrogen, and $R_9$ is hydrogen; and wherein the virus comprises a flavivirus.

In one embodiment, in the compound of formula (I), $R_3$ is fluorine or hydrogen. In one embodiment, in the compound of formula (I), $R_4$ is chlorine or hydrogen. In one embodiment, in the compound of formula (I), $R_5$ is chlorine or hydrogen.

In one embodiment, in the compound of formula (I), when $R_2$ is nitrogen oxide, $R_2$ is selected from the group consisting of $NO_2$, NO, $N_2O$, and $N_2O_5$. In one embodiment, in the compound of formula (I), when $R_6$ is nitrogen oxide, $R_6$ is selected from the group consisting of $NO_2$, NO, $N_2O$, and $N_2O_5$.

In one embodiment, the compound of formula (I) is the compound of formulae (Ia)-(Ip):

(Ia)

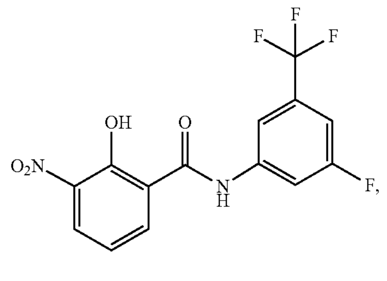

-continued
(Ib)
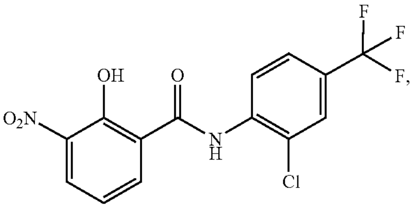
(Ic)
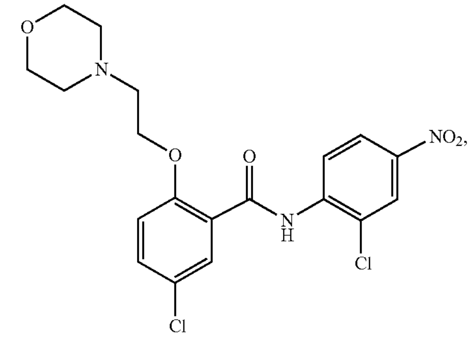
(Id)
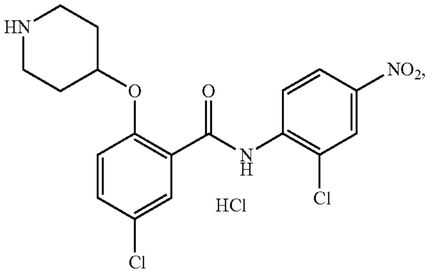
(Ie)
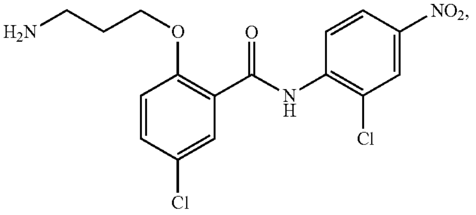
(If)
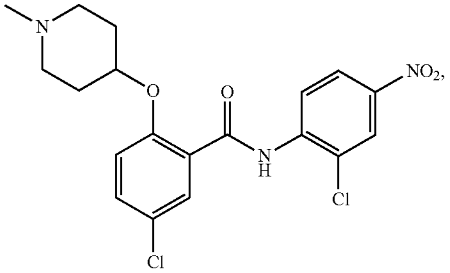
(Ig)
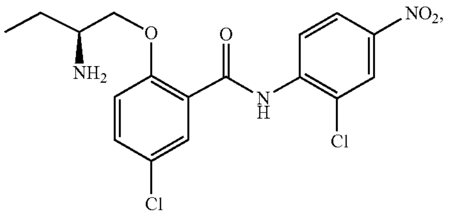
-continued
(Ih)
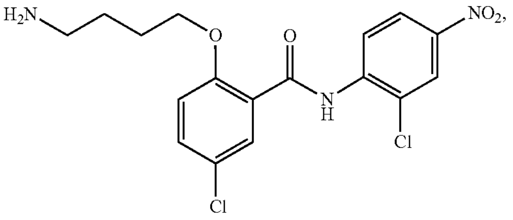
(Ii)
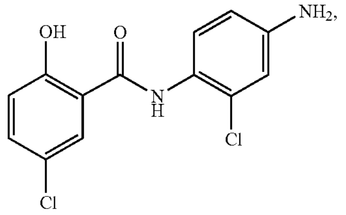
(Ij)
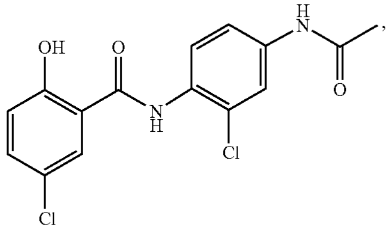
(Ik)
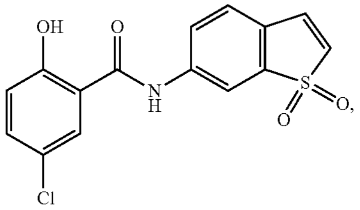
(Il)
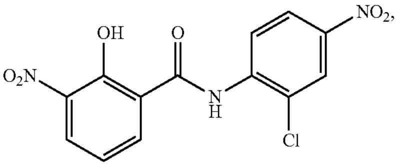
(Im)
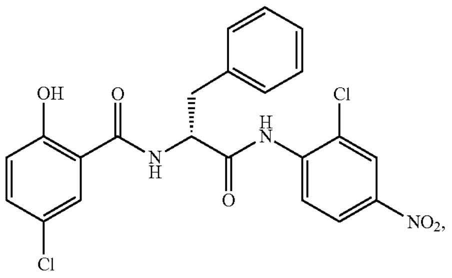
(In)
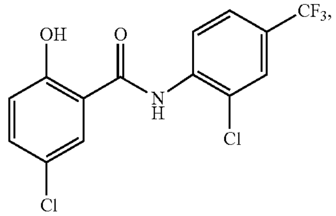

-continued (Io)

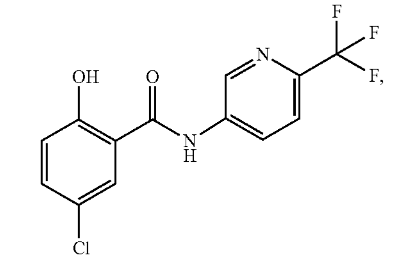

or (Ip)

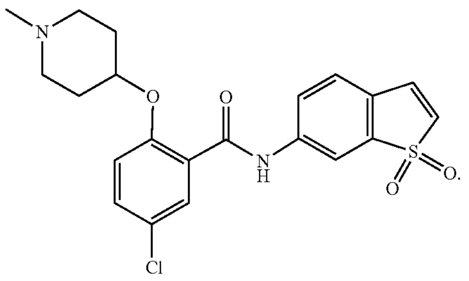

The present disclosure relates to, inter alia, methods and compositions for inhibiting replication of flaviviruses and methods of treating and/or preventing infections caused by flaviviruses, including, for example, treating subjects infected with flaviviruses, compounds for use in such methods, and methods for evaluating the effectiveness of compounds in inhibiting flaviviral replication. As used herein, the term “flavivirus” (used interchangeably herein as “flaviviral”) includes any and all species of viruses in the Flavivirus genus according to the International Committee on Taxonomy of Viruses Master Species List 2016 v1.3, dated May 25, 2017, including Zika virus, Dengue virus, Apoi virus, Aroa virus, Bagaza virus, Banzi virus, Bouboui virus, Bukalasa bat virus, Cacipacore virus, Carey Island virus, Cowbone Ridge virus, Dakar bat virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Sal Vieja virus, San Perlita virus, Saumarez Reef virus, Sepik virus, St. Louis encephalitis virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, and all recognized subtypes of the foregoing species (e.g., DENV1, DENV2, DENV3, DENV4, Alfuy virus, and Kunjin virus). In one embodiment, the flavivirus is selected from the group consisting of Zika virus, Dengue virus serotype 1, Dengue virus serotype 2, Dengue virus serotype 3, Dengue virus serotype 4, yellow fever virus, West Nile virus, and Japanese encephalitis virus. In one embodiment, the flavivirus is Zika virus.

Flavivirus genomic RNA is single-stranded and of positive (i.e., mRNA) polarity. The viral genome is approximately 11 kb in length, consisting of a 5' UTR, a single long open reading frame (ORF), and a 3' UTR. The single ORF encodes a polyprotein that is co- and post-translationally processed by viral and cellular proteases into individual functional proteins. Among the flaviviral proteins, NS3 is a multi-functional protein with activities of a serine protease, an RNA triphosphatase, a nucleoside triphosphatase, and a helicase. The viral protease is a complex with two components: the N-terminal 184 amino acids (aa) of viral NS3 protein and a hydrophobic core of about 40 aa in length within viral NS2B protein as an essential cofactor for flaviviral protease activity and replication.

The flavivirus NS2B-NS3 protease is a highly conserved and replication-critical enzyme. See Noble et al., “Ligand-Bound Structures of the Dengue Virus Protease Reveal the Active Conformation,” *Journal of Virology* 86:438-446 (2012); Prusis et al., “Proteochemometrics Analysis of Substrate Interactions With Dengue Virus NS3 Proteases,” *Bioorganic & Medicinal Chemistry* 16:9369-9377 (2008); Chambers et al., “Processing of the Yellow Fever Virus Nonstructural Polyprotein: A Catalytically Active NS3 Proteinase Domain and NS2B Are Required for Cleavages at Dibasic Sites,” *J. Virol.* 65:6042-6050 (1991); Falgout et al., “Both Nonstructural Proteins NS2B and NS3 Are Required for the Proteolytic Processing of Dengue Virus Nonstructural Proteins,” *J. Virol.* 65:2467-2475 (1991); Lescar et al., “Towards the Design of Antiviral Inhibitors Against Flaviviruses: The Case for the Multifunctional NS3 Protein From Dengue Virus as a Target,” *Antiviral Res.* 80:94-101 (2008), all of which are hereby incorporated by reference in their entirety. FIG. 8 shows the conservation of amino acid residues at positions along the NS3 proteins of various flaviviruses and their consensus sequence (SEQ ID NO:1 DENV2 NS3; SEQ ID NO:2 DENV1 NS3; SEQ ID NO:3 DENV3 NS3; SEQ ID NO:4 DENV4 NS3; SEQ ID NO:5 WNV NS3; SEQ ID NO:6 JEV NS3; SEQ ID NO:7 SLEV NS3; SEQ ID NO:8 ZIKV NS3; SEQ ID NO:9 YFV NS3; SEQ ID NO:10 TBEV NS3; SEQ ID NO:11 POWV NS3). As shown in FIG. 8, the NS3 proteins of flaviviruses show very high sequence homology, indicating high structural similarity among flaviviral NS3 proteins.

The NS2B/NS3 flaviviral protease works with host proteases to cleave the polyprotein precursor produced by the viral genome. See Noble et al., “Ligand-Bound Structures of the Dengue Virus Protease Reveal the Active Conformation,” *Journal of Virology* 86:438-446 (2012); Prusis et al., “Proteochemometrics Analysis of Substrate Interactions With Dengue Virus NS3 Proteases,” *Bioorganic & Medicinal Chemistry* 16:9369-9377 (2008); Chambers et al., “Processing of the Yellow Fever Virus Nonstructural Polyprotein: A Catalytically Active NS3 Proteinase Domain and NS2B Are Required for Cleavages at Dibasic Sites,” *J. Virol.* 65:6042-6050 (1991); Falgout et al., “Both Nonstructural Proteins NS2B and NS3 Are Required for the Proteolytic Processing of Dengue Virus Nonstructural Proteins,” *J. Virol.* 65:2467-2475 (1991); Lescar et al., “Towards the Design of Antiviral Inhibitors Against Flaviviruses: The Case for the Multifunctional NS3 Protein From Dengue Virus as a Target,” *Antiviral Res.* 80:94-101 (2008), all of which are hereby incorporated by reference in their entirety. The flavivirus protease is a trypsin-like serine protease that preferentially cleaves protein substrates at sites immediately following two basic residues (K or R at positions P2 and P1). Crystal structures of the NS2B-NS3 proteases of flaviviruses in covalently-linked forms (e.g., NS2B-G4SG4linker-NS3) have been determined in both apo and inhibitor-bound forms. Aleshin et al., “Structural Evidence for Regulation and Specificity of Flaviviral Proteases and Evolution of the Flaviviridae Fold,” *Protein Sci.* 16:795-806 (2007); Assenberg et al., “Crystal Structure of a Novel Conformational State of the Flavivirus NS3 Protein: Implications for Polyprotein Processing and Viral Replication," *J. Virol.* 83:12895-12906 (2009); Chandramouli et al., "Serotype-specific Structural Differences in the Protease-Cofactor Complexes of the Dengue Virus Family," *J. Virol.* 84:3059-306 (2010); Erbel et al., "Structural Basis for the Activation of Flaviviral NS3 Proteases From Dengue and West Nile Virus," *Nat. Struct. Mol. Biol.* 13:372-373 (2006); Hammamy et al., "Development and Characterization of New Peptidomimetic Inhibitors of the West Nile Virus NS2B-NS3 Protease," *ChemMedChem* 8:231-241 (2013); Luo et al., "Flexibility Between the Protease and Helicase Domains of the Dengue Virus NS3 Protein Conferred by the Linker Region and Its Functional Implications," *J. Biol. Chem.* 285:18817-18827 (2010); Luo et al., "Crystal Structure of the NS3 Protease-Helicase From Dengue Virus," *J. Virol.* 82:173-183 (2008); Luo et al., "Insights Into RNA Unwinding and ATP Hydrolysis by the Flavivirus NS3 Protein," *Embo J.* 27:3209-3219 (2008); Noble et al., "Ligand-bound Structures of the Dengue Virus Protease Reveal the Active Conformation," *J. Virol.* 86:438-446 (2012); Robin et al., "Structure of West Nile Virus NS3 Protease: Ligand Stabilization of the Catalytic Conformation," *J. Mol. Biol.* 385: 1568-1577 (2009), all of which are hereby incorporated by reference in their entirety. In the absence of substrate or active site inhibitor, the N-terminal but not C-terminal portion of NS2B is bound to NS3; whereas the conformation of the C-terminal portion of NS2B varies considerably, presumably in the "open" inactive conformations. Upon inhibitor or substrate binding to the NS3 active site, the C-terminal portion of NS2B "wraps around" the NS3 core, closing the NS3 active site with the so-called active "closed" conformation. The conformation of the N-terminal portion of NS2B remains the same as that of apo form. NS2B binding and conformational change are required for NS3 function; mutations that abrogate NS2B binding greatly reduce the proteolytic activity of the complex. Chappell et al., "Mutagenesis of the West Nile Virus NS2B Cofactor Domain Reveals Two Regions Essential for Protease Activity," *J. Gen. Virol.* 89:1010-1014 (2008); Niyomrattanakit et al., "Identification of Residues in the Dengue Virus Type 2 NS2B Cofactor That Are Critical for NS3 Protease Activation," *J. Virol.* 78:13708-13716 (2004), both of which are hereby incorporated by reference in their entirety.

In addition, the conformational change of NS2B upon active site inhibitor binding has been verified by a number of NMR studies using the linked construct and by molecular dynamic studies. Su et al., "NMR Analysis of the Dynamic Exchange of the NS2B Cofactor Between Open and Closed Conformations of the West Nile Virus NS2B-NS3 Protease," *PLoS Negl. Trop. Dis.* 3:e561 (2009); Su et al., "NMR Study of Complexes Between Low Molecular Mass Inhibitors and the West Nile Virus NS2B-NS3 Protease," *FEBS J.* 276: 4244-4255 (2009); Ekonomiuk & Caflisch, "Activation of the West Nile Virus NS3 Protease: Molecular Dynamics Evidence for a Conformational Selection Mechanism," *Protein Sci.* 18:1003-1011 (2009); Kang et al., "Exploring the Binding of Peptidic West Nile Virus NS2B-NS3 Protease Inhibitors by NMR," *Antiviral Res.* 97:137-144 (2013); Zhu et al., "Conformational Change Study of Dengue Virus NS2B-NS3 Protease Using 19F NMR Spectroscopy," *Biochem. Biophys. Res. Commun.* 461:677-680 (2015), all of which are hereby incorporated by reference in their entirety. Co-expression of unlinked NS2B-NS3 protease was developed, and NMR studies indicated that NS2B in the unlinked protease mainly adopted the "closed" conformation even in the absence of substrate analogs. Chen et al., "The Dengue Virus NS2B-NS3 Protease Retains the Closed Conformation in the Complex With BPTI," *FEBS Lett.* 588:2206-2211 (2014); Kim et al., "NMR Analysis of a Novel Enzymatically Active Unlinked Dengue NS2B-NS3 Protease Complex," *J. Biol. Chem.* 288:12891-12900 (2013); Li et al., "An Inhibition Model of BPTI to Unlinked Dengue Virus NS2B-NS3 Protease," *FEBS Lett.* 588:2794-2799 (2014); de la Cruz et al., "Binding of Low Molecular Weight Inhibitors Promotes Large Conformational Changes in the Dengue Virus NS2B-NS3 Protease: Fold Analysis by Pseudocontact Shifts," *J. Am. Chem. Soc.* 133:19205-19215 (2011); de la Cruz et al., "Binding Mode of the Activity-Modulating C-terminal Segment of NS2B to NS3 in the Dengue Virus NS2B-NS3 Protease," *FEBS J.* 281:1517-1533 (2014), all of which are hereby incorporated by reference in their entirety.

For flavivirus protease, two regions of NS2B (N-terminal (Nter): amino acids (aa) 53-61 and C-terminal (Cter): aa 74-86) are important for the protease function. Chappell et al., "Mutagenesis of the West Nile Virus NS2B Cofactor Domain Reveals Two Regions Essential for Protease Activity," *J. Gen. Virol.* 89:1010-1014 (2008); Niyomrattanakit et al., "Identification of Residues in the Dengue Virus Type 2 NS2B Cofactor That Are Critical for NS3 Protease Activation," *J. Virol.* 78:13708-13716 (2004); Radichev et al., "Structure-based Mutagenesis Identifies Important Novel Determinants of the NS2B Cofactor of the West Nile Virus Two-Component NS2B-NS3 Proteinase," *J. Gen. Virol.* 89:636-641 (2008); Phong et al., "Dengue Protease Activity: The Structural Integrity and Interaction of NS2B With NS3 Protease and Its Potential as a Drug Target," *Biosci Rep.* 31:399-409 (2011), all of which are hereby incorporated by reference in their entirety. It has also been demonstrated that NS2B Nter residues display similar conformations in all structures. Brecher et al., "The Flavivirus Protease as a Target for Drug Discovery," *Virol. Sin.* 28:326-336 (2013), which is hereby incorporated by reference in its entirety. In addition, the NS2B aa 49-66 only (Cter-deletion) peptide is sufficient to stabilize the NS3 conformation. Luo et al., "Crystal Structure of the NS3 Protease-Helicase From Dengue Virus," *J. Virol.* 82:173-183 (2008); Luo et al., "Flexibility Between the Protease and Helicase Domains of the Dengue Virus NS3 Protein Conferred by the Linker Region and Its Functional Implications," *J. Biol. Chem.* 285:18817-18827 (2010), which are hereby incorporated by reference in their entirety. Moreover, unlike the active site which is flat and featureless, the NS3 pockets holding the NS2B Nter residues (such as key contact residues L51, V53, V59, and W61) are deep and hydrophobic.

Attempts to develop flavivirus protease inhibitors have focused on the NS3 active site but have not been very successful. As disclosed herein, screens may be used to identify compounds that orthosterically inhibit NS3 function. As disclosed herein, an assay may be used to identify orthosteric inhibitors to impair NS2B-NS3 interactions. Using this strategy, candidate compounds may be identified that can significantly inhibit the interactions between NS2B and NS3. These compounds may inhibit protease activity and also significantly reduce titers of ZIKV, DENV1, DENV2, DENV3, DENV4, WNV, YFV, POWV, and JEV. Given the high structural similarity of the NS2B/NS3 complex amongst flaviviruses, as shown in FIG. 7, skilled artisans will appreciate that comparable results would likely be observed with other flaviviruses. Compounds disclosed may inhibit the growth of flaviviruses tested.

The NCGC Pharmaceutical collection that harbors about 2,800 drugs approved for administration to human subjects by the FDA of the United States or other countries may be screened for potential inhibitors of flaviviral replication as potential medical treatments for flaviviral infection. The assay may be used to identify candidate inhibitors.

Selected candidate compounds may be subjected to a protease inhibition assay and evaluated for inhibition of NS2B-NS3 protease activity. Coupled with low toxicity to cells at doses with high antiflaviviral activity, compounds described herein may show high therapeutic indices as potential compounds for inhibition of interaction of flaviviral NS2B with flaviviral NS3, of flaviviral NS2B/NS3 protease activity, and flaviviral replication, may also be valuable compounds to prevent and/or treat flaviviral infection and/or a condition resulting from a flaviviral infection, such as, for example, ZIKV, DENV1, DENV2, DENV3, DENV4, WNV, YFV, JEV, TBEV, POWV or SLEV.

In one embodiment, contacting one or more cells that have been infected with a flavivirus comprises administering the compound to a subject. In another embodiment, contacting one or more cells that have been infected with a flavivirus comprises administering the compound to a subject and the subject is a mammal. In yet another embodiment, contacting one or more cells that have been infected with a flavivirus comprises administering the compound to a subject and the subject is a human. In one embodiment, the cells comprise tissue that has been removed from a mammal. In another embodiment, the cells comprise tissue that has been removed from a human.

The flavivirus may be ZIKV, DENV1, DENV2, DENV3, DENV4, YFV, WNV, POWV, SLEV, TBEV, JEV, or any other flavivirus. For example, the compound may be formula (I) or a pharmaceutically acceptable salt thereof and the flavivirus may be ZIKV, the compound may be formula (I) or a pharmaceutically acceptable salt thereof and the flavivirus may be DENV1, the compound may be formula (I) or a pharmaceutically acceptable salt thereof and the flavivirus may be DENV2, the compound may be formula (I) or a pharmaceutically acceptable salt thereof and the flavivirus may be DENV3, the compound may be formula (I) or a pharmaceutically acceptable salt thereof and the flavivirus may be DENV4, the compound may be formula (I) or a pharmaceutically acceptable salt thereof and the flavivirus may be YFV, the compound may be formula (I) or a pharmaceutically acceptable salt thereof and the flavivirus may be WNV, the compound may be formula (I) or a pharmaceutically acceptable salt thereof and the flavivirus may be POWV, the compound may be formula (I) or a pharmaceutically acceptable salt thereof and the flavivirus may be SLEV, the compound may be formula (I) or a pharmaceutically acceptable salt thereof and the flavivirus may be TBEV, or the compound may be formula (I) or a pharmaceutically acceptable salt thereof and the flavivirus may be JEV. The compound may be formulae (Ia)-(Ip) or a pharmaceutically acceptable salt thereof and the flavivirus may be ZIKV, DENV1, DENV2, DENV3, DENV4, YFV, WNV, POWV, SLEV, TBEV, or JEV, or any other flavivirus. The compound may be any compound listed in Table 1 (optionally excluding niclosamide) or a pharmaceutically acceptable salt thereof and the flavivirus may be ZIKV, DENV1, DENV2, DENV3, DENV4, YFV, WNV, POWV, SLEV, TBEV, or JEV, or any other flavivirus. In one embodiment, the flavivirus is selected from the group consisting of Zika virus, Dengue virus serotype 1, Dengue virus serotype 2, Dengue virus serotype 3, Dengue virus serotype 4, yellow fever virus, West Nile virus, and Japanese encephalitis virus.

In one embodiment, the flavivirus is Zika virus. In one embodiment, the contacting one or more cells that have been infected with a flavivirus (i.e., Zika virus) comprises administering the compound to a subject. In another embodiment, the contacting one or more cells that have been infected with a flavivirus (i.e., Zika virus) comprises administering the compound to a subject and the subject is a mammal. In yet another embodiment, the contacting one or more cells that have been infected with a flavivirus (i.e., Zika virus) comprises administering the compound to a subject and the subject is a human. In one embodiment, the cells comprise tissue that has been removed from a mammal having a flavivirus (i.e., Zika virus). In another embodiment, the cells comprise tissue that has been removed from a human having a flavivirus (i.e., Zika virus).

In any embodiment described herein, any of the compounds identified may be administered before confirmation of the presence or infection of any of ZIKV, DENV1, DENV2, DENV3, DENV4, YFV, WNV, POWV, SLEV, TBEV, JEV, or any other flavivirus in a cell or cells or sample from a subject, including a human subject or other mammalian subject, with the effect of preventing infection. For example, a sample or subject may be suspected of having been exposed to a flavivirus and administration of one or more of the foregoing compounds may be applied so as to prevent replication of the virus or viruses should contact otherwise sufficient to cause viral replication or infection of the cells have been present. Notwithstanding an apparent mechanism of action of the foregoing compounds in preventing viral replication, preventing or reversing infection, spread, or illness, as disclosed herein, the present disclosure is not limited to preventing viral replication, preventing or reversing infection, spread, or illness according to any particular mechanism of action, including any apparent mechanism of action disclosed herein. Any or all of the foregoing compounds may prevent flaviviral replication, prevent or reverse infection, spread, or illness, by any mechanism of action and still be included within the present disclosure, even if not by a mechanism of action disclosed herein. Antiflaviviral effects of formula (I) may occur by any mechanism, and identification of potential mechanism(s) of action identified herein in no way excludes mechanisms of action by which these compounds may exert antiflaviviral effects, other than or including any mechanism disclosed herein, from falling within the scope of subject matter disclosed herein, without limitation as to any mechanism for such antiflaviviral effects not explicitly identified mechanistically.

A third aspect relates to a method of treating and/or preventing a flavivirus infection and/or a condition resulting from a flavivirus infection. The method includes administering an effective amount of a compound of formula (I) or a pharmaceutically acceptable salt thereof (I)

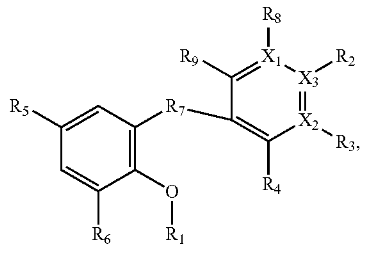

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_7$ is amide, wherein the amide can be optionally substituted with aryl, heterocyclyl, hydrogen, or oxygen;

$R_8$ is hydrogen, halogen, or trihalomethane;

$R_9$ is halogen or hydrogen;

$X_1$, $X_2$, and $X_3$ are independently selected from CH and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_7$ is —C═ONH—, $R_8$ is hydrogen, and $R_9$ is hydrogen, under conditions effective to treat and/or prevent a flavivirus infection and/or a condition resulting from a flavivirus infection.

This aspect is carried out in accordance with the previous described aspects.

In one embodiment, in the compound of formula (I), $R_3$ is fluorine or hydrogen. In one embodiment, in the compound of formula (I), $R_4$ is chlorine or hydrogen. In another embodiment, in the compound of formula (I), $R_5$ is chlorine or hydrogen.

In one embodiment, in the compound of formula (I), when $R_2$ is nitrogen oxide, $R_2$ is selected from the group consisting of $NO_2$, NO, $N_2O$, and $N_2O_5$. In another embodiment, in the compound of formula (I), when $R_6$ is nitrogen oxide, $R_6$ is selected from the group consisting of $NO_2$, NO, $N_2O$, and $N_2O_5$. In another embodiment, the compound of formula (I) is the compound of formulae (Ia)-(Ip) as described herein.

The methods disclosed herein may include administration of a pharmaceutical composition comprising a compound of formula (I) (for example, formulae (Ia)-(Ip)) as disclosed above, or a pharmaceutically acceptable salt form thereof, and a pharmaceutically acceptable carrier or diluent. While it may be possible for formula (I) and, for example, formulae (Ia)-(Ip), or pharmaceutically acceptable salts thereof to be administered as the raw chemical, it may be preferable to present them as a pharmaceutical composition. The present disclosure may provide a pharmaceutical composition comprising formula (I), for example, formulae (Ia)-(Ip), or pharmaceutically acceptable salts thereof, together with one or more pharmaceutically carriers thereof and optionally one or more other therapeutic ingredients.

In one embodiment, the composition used in the methods disclosed herein further comprises a pharmaceutically acceptable carrier. "Pharmaceutically acceptable carriers" as used herein refer to conventional pharmaceutically acceptable carriers. See *Remington's Pharmaceutical Sciences*, by E. W. Martin, Mack Publishing Co., Easton, Pa., 15th Edition (1975), which is hereby incorporated by reference in its entirety, and describes compositions suitable for pharmaceutical delivery of the compositions described herein. In particular, a pharmaceutically acceptable carrier as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits. In one embodiment, the pharmaceutically acceptable carrier is selected from the group consisting of a liquid filler, a solid filler, a diluent, an excipient, a solvent, and an encapsulating material.

Pharmaceutically acceptable carriers (e.g., additives such as diluents, immunostimulants, adjuvants, antioxidants, preservatives, and solubilizing agents) are non-toxic to the cell or subject being exposed thereto at the dosages and concentrations employed. Examples of pharmaceutically acceptable carriers include water, e.g., buffered with phosphate, citrate, and another organic acid. Representative examples of pharmaceutically acceptable excipients that may be useful in the present disclosure include antioxidants such as ascorbic acid; low molecular weight (less than about 10 residues) polypeptides; proteins, such as serum albumin, gelatin, or immunoglobulins; adjuvants (selected so as to avoid adjuvant-induced toxicity, such as a (3-glucan as described in U.S. Pat. No. 6,355,625, which is hereby incorporated by reference in its entirety, or a granulocyte colony stimulating factor (GCSF)); hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

Pharmaceutically acceptable carriers refer to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents, and dispersing agents. Prevention of the action of microorganisms can be ensured by the inclusion of various antibacterial and antifungal agents such as paraben, chlorobutanol, phenol, sorbic acid, and the like. It can also be desirable to include isotonic agents such as sugars, sodium chloride, and the like. Prolonged absorption of the injectable pharmaceutical form can be brought about by the inclusion of agents, such as aluminum monostearate and gelatin, which delay absorption. Injectable depot forms may be formed by microencapsule matrices of the compound in biodegradable polymers such as polylactide-polyglycolide, poly(orthoesters), and poly(anhydrides). Depending upon the ratio of compound to polymer and the nature of the particular polymer employed, the rate of compound release can be controlled. Depot injectable formulations are also prepared by entrapping the compound in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

The anti-flavivirus compound or anti-flavivirus compound derivative used in the methods described herein may comprise different types of carriers depending on whether it is to be administered in solid, liquid, or aerosol form, and whether it needs to be sterile for such routes of administration as injection. The compounds used in the methods described herein may be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, e.g., Remington's Pharmaceutical Sciences, 18th Ed. Mack Printing Company, 1990, which is hereby incorporated by reference in its entirety).

The phrase "pharmaceutically acceptable salt" refers to salts prepared from pharmaceutically acceptable non-toxic acids or bases including inorganic acids and bases and organic acids and bases. When the compounds used in the methods described herein are basic, salts may be prepared from pharmaceutically acceptable non-toxic acids including inorganic and organic acids. Suitable pharmaceutically acceptable acid addition salts for the compounds described herein include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic, and the like. When the compounds contain an acidic side chain, suitable pharmaceutically acceptable base addition salts for the compounds described herein include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine), and procaine. Further pharmaceutically acceptable salts include, when appropriate, non-toxic ammonium cations and carboxylate, sulfonate and phosphonate anions attached to alkyl having from 1 to 20 carbon atoms.

The anti-flavivirus compound or anti-flavivirus compound derivative used in the methods described herein may be formulated into a composition in a free base, neutral or salt form. Pharmaceutically acceptable salts, include the acid addition salts, for example, those formed with the free amino groups of a proteinaceous composition, or those formed with inorganic acids such as, for example, hydrochloric or phosphoric acids, or such organic acids as acetic, oxalic, tartaric, or mandelic acid. Salts formed with the free carboxyl groups can also be derived from inorganic bases such as for example, sodium, potassium, ammonium, calcium, or ferric hydroxides; or such organic bases as isopropylamine, trimethylamine, histidine, or procaine. Upon formulation, solutions may be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules, and the like.

As used herein, the term "physiologically functional derivative" refers to any pharmaceutically acceptable derivative of a compounds used in the methods described herein, that, upon administration to a mammal, is capable of providing (directly or indirectly) a compound of the present disclosure or an active metabolite thereof. Such derivatives, for example, esters and amides, will be clear to those skilled in the art, without undue experimentation. Reference may be made to the teaching of *Burger's Medicinal Chemistry And Drug Discovery,* $5^{th}$ Edition, Vol 1: Principles and Practice, which is hereby incorporated by reference in its entirety.

As used herein, the term "effective amount" includes an amount of a compound or pharmaceutical agent that will elicit the biological or medical response of a cell, tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of the anti-flavivirus compound of the present disclosure, as well as salts, solvates, and physiological functional derivatives thereof, may be administered as the raw chemical. Additionally, the active ingredient may be presented as a pharmaceutical composition.

Pharmaceutical compositions used in the methods of the present disclosure comprise an effective amount of one or more anti-flavivirus compound or anti-flavivirus compound derivative, or additional agent dissolved or dispersed in a pharmaceutically acceptable carrier. The phrases "pharmaceutical or pharmacologically acceptable" refer to molecular entities and compositions that do not produce an adverse, allergic, or other untoward reaction when administered to an animal, such as, for example, a human, as appropriate. The preparation of a pharmaceutical composition that contains at least one anti-flavivirus compound or anti-flavivirus compound derivative, or additional active ingredient will be known to those of skill in the art in light of the present disclosure, as exemplified by Remington's Pharmaceutical Sciences, 18th Ed. Mack Printing Company, 1990, which is hereby incorporated by reference in its entirety. Moreover, for animal (e.g., human) administration, it will be understood that preparations should meet sterility, pyrogenicity, general safety and purity standards as required by FDA Office of Biological Standards.

Further in accordance with the present disclosure, the compositions used in the methods described herein that are suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of the composition contained therein, its use in administrable composition for use in practicing the methods of the present disclosure is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

In accordance with the present disclosure, the composition administered in the methods described herein may be combined with the carrier in any convenient and practical manner, i.e., by solution, suspension, emulsification, admixture, encapsulation, absorption and the like. Such procedures are routine for those skilled in the art.

In one embodiment of the present disclosure, the composition used in the methods described herein is combined or mixed thoroughly with a semi-solid or solid carrier. The mixing can be carried out in any convenient manner such as grinding. Stabilizing agents may also be added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, and mannitol.

In further embodiments, the present disclosure may include the use of pharmaceutical lipid vehicle compositions that include the anti-flavivirus compound or anti-flavivirus compound derivative, one or more lipids, and an aqueous solvent. As used herein, the term "lipid" may include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or man-made). A lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Compounds other than those specifically described herein that are understood by one of skill in the art as lipids are also encompassed by the compositions and methods of the present disclosure.

One of ordinary skill in the art would be familiar with the range of techniques that can be employed for dispersing a composition in a lipid vehicle. For example, the anti-flavivirus compound or anti-flavivirus compound derivative used in the methods described herein, may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

For example, a compound or compounds used in the methods described herein may be administered to a subject, such as a mammal, human, or other subject, to contact a cell or cells to prevent replication of a flavivirus, including stereoisomers, racemic mixtures, pharmaceutically acceptable salts, or in complex with one or more excipients or pharmaceutically acceptable carriers or otherwise formulated for such administration in accordance with the examples detailed in the foregoing paragraphs, in accordance with the present disclosure. All combinations of the foregoing are explicitly intended to be and are included as aspects in accordance with the present disclosure.

The actual dosage amount of a composition of the present disclosure administered to a subject (e.g., an animal or human patient) in the methods described herein can be determined by physical and physiological factors such as body weight, severity of condition, the type of disease being treated, previous or concurrent therapeutic interventions, idiopathy of the patient, and route of administration. Depending upon the dosage and the route of administration, the number of administrations of a preferred dosage and/or an effective amount may vary according to the response of the subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one of ordinary skill in the art of preparing such pharmaceutical formulations, and as such, a variety of dosages and treatment regimens may be desirable.

For example, a dose may comprise from between about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, can be administered, based on the numbers described above.

In one embodiment of the present disclosure, the anti-flavivirus compound or anti-flavivirus compound derivative used in the methods described herein are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tablets, troches, capsules, elixirs, suspensions, syrups, wafers, and the like. Tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, and/or orange flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin, and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

In further embodiments, the anti-flavivirus compound or anti-flavivirus compound derivative may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy injectability exists. It must be stable under the conditions of manufacture and storage and must be preserved against the contaminating action of microorganisms, such as bacteria and fungi.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., "Remington's Pharmaceutical Sciences" $15^{th}$ Edition, pages 1035-1038 and 1570-1580, which is hereby incorporated by reference in its entirety). Some variation in dosage will necessarily occur depending on the condition of the subject being treated.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments of the present disclosure, the methods disclosed herein deliver the compound via various miscellaneous routes, for example, topical (i.e., transdermal) administration, mucosal administration (intranasal, vaginal), and/or inhalation.

Pharmaceutical compositions for topical administration may include the active compound formulated for a medicated application such as an ointment, paste, cream, or powder. Ointments include all oleaginous, adsorption, emulsion, and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream and petrolatum as well as any other suitable absorption, emulsion, or water-soluble ointment base. Topical preparations may also include emulsifiers, gelling agents, and antimicrobial preservatives as necessary to preserve the active ingredient and provide for a homogenous mixture. Transdermal administration of the present disclosure may also comprise the use of a "patch." For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described. Likewise, the delivery of compounds using intranasal microparticle resins and lysophosphatidyl-glycerol compounds are also well-known in the pharmaceutical arts. Transmucosal drug delivery in the form of a polytetrafluoroetheylene support matrix may be adopted for use in accordance with the present disclosure.

The term aerosol refers to a colloidal system of finely divided solid of liquid particles dispersed in a liquefied or pressurized gas propellant. An aerosol for inhalation may consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In addition, in various embodiments, the compositions according to the disclosure may be formulated for delivery via any route of administration. The route of administration may refer to any administration pathway known in the art, including but not limited to aerosol, nasal, oral, transmucosal, transdermal, subcutaneous, or parenteral. Parenteral refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or in the form of lyophilized powders.

Formulations include those suitable for oral, parenteral (including subcutaneous, intradermal, intramuscular, intravenous, and intraarticular), rectal, and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. In general, formulations may be prepared by uniformly and intimately bringing into association an active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of an active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

In one embodiment, the treatment comprises administering said formula (I) (for example, administering formulae (Ia)-(Ip)) to a subject orally, by inhalation, by intranasal instillation, topically, transdermally, intradermally, parenterally, subcutaneously, intravenous injection, intra-arterial injection, intramuscular injection, intrapleurally, intraperitoneally, intrathecally, or by application to a mucous membrane.

In addition, compounds according to the present disclosure may be administered alone or in combination with other agents, including other compounds of the present disclosure. Certain compounds according to the present disclosure may be effective for enhancing the biological activity of certain agents according to the present disclosure by reducing the metabolism, catabolism or inactivation of other compounds and as such, may be co-administered for this intended effect.

In one embodiment, the method further includes selecting a subject that has an infection caused by a flavivirus or is at risk of developing an infection caused by a flavivirus. In one embodiment, the flavivirus is selected from the group consisting of Zika virus, Dengue virus serotype 1, Dengue virus serotype 2, Dengue virus serotype 3, Dengue virus serotype 4, yellow fever virus, West Nile virus, and Japanese encephalitis virus, or any flavivirus as further described herein.

For purposes of this and other aspects of the disclosure, the target "subject" encompasses any vertebrate, such as an animal, preferably a mammal, more preferably a human. In the context of administering a composition of the disclosure for purposes of preventing and/or treating a flaviviral in a subject comprising in a subject, the target subject encompasses any subject that has a flaviviral infection or is at risk of developing a flaviviral infection. Particularly susceptible subjects include those exposed to a flavivirus, and may include infants, juveniles, adults, or elderly adults that have a flaviviral infection or are at risk of having a flaviviral infection. In one embodiment, the subject is an infant, a juvenile, or an adult. In one embodiment, the method is performed in a subject having a preexisting condition or, alternatively, may be performed in a subject having no preexisting condition. The method may also be performed on a subject who has been previously treated for a flaviviral infection.

In one embodiment, the method further comprises administering one or more additional treatments and/or agents which prevent or treat viral infections and/or a condition resulting from viral infections. In another embodiment, the method further comprises repeating said administering of formula (I) (e.g., formulae (Ia)-(Ip)).

As used herein, the phrase "therapeutically effective amount" means an amount of oxygen that elicits the biological or medicinal response that is being sought in a tissue, system, animal, individual, or human by a researcher, veterinarian, medical doctor, or other clinician. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size, and sex of the subject. Optimal amounts can also be determined based on monitoring of the subject's response to treatment. The term "treatment" or "treat" may include effective inhibition, suppression, or cessation of flaviviral symptoms so as to prevent or delay the onset, retard the progression, or ameliorate the symptoms of the infection caused by a flavivirus.

One goal of treatment is the amelioration, either partial or complete, either temporary or permanent, of patient symptoms. Any amelioration is considered successful treatment. This is especially true as amelioration of some magnitude may allow reduction of other medical or surgical treatment which may be more toxic or invasive to the patient.

As used herein a sample may include any sample obtained from a living system or subject, including, for example, blood, serum, and/or tissue. In one embodiment, a sample is obtained through sampling by minimally invasive or non-invasive approaches (for example, by urine collection, stool collection, blood drawing, needle aspiration, and other procedures involving minimal risk, discomfort, or effort). Alternatively, samples may be gaseous (for example, breath that has been exhaled) or liquid fluid. Liquid samples may include, for example, urine, blood, serum, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, nasal excretions, and other liquids. Samples may also include a clinical sample such as serum, plasma, other biological fluid, or tissue samples, and also includes cells in culture, cell supernatants, and cell lysates. In one embodiment, the sample is selected from the group consisting of whole blood, serum, urine, and nasal excretion. Samples may be in vivo or ex vivo.

As used herein, the term "simultaneous" therapeutic use refers to the administration of at least one additional agent beyond the compound of formula (I), for example, agents administered before, during, or after the compound of formula (I), optionally, by the same route and at the same time or at substantially the same time. As used herein, the term "separate" therapeutic use refers to an administration of at least one additional agent beyond the compound of formula (I), for example, agents administered before, during, or after administration of compound of formula (I), at the same time or at substantially the same time by different routes.

As used herein, the term "sequential" therapeutic use refers to administration of at least one additional agent beyond the compound of formula (I), for example, agents administered before, during, or after administration of the compound of formula (I), at different times, the administration route being identical or different. More particularly, sequential use refers to the whole administration of the additional agent before administration of compound of formula (I). It is thus possible to administer the additional agent over several minutes, hours, or days before applying the compound of formula (I). In one embodiment, the additional agent is administered before, during, or after the compound of formula (I).

Any of the compounds disclosed herein may be used in accordance with the present disclosure to prevent infection of a subject, such as a human subject, or other mammalian subject, with a flavivirus, such as one of the types of flaviviruses identified in the above paragraphs. For example, any amount of an anti-flavivirus therapeutic of the present disclosure, or a pharmaceutically acceptable salt of the compound, optionally in combination with a pharmaceutically acceptable excipient, carrier, or additive, sufficient to prevent flaviviral infection, may be administered to such subject. Use of any one or more of the foregoing compounds to prevent infection with any one or more flaviviruses, including those specifically identified above, is explicitly contemplated and hereby included in the present disclosure. In one embodiment, the flavivirus infection is prevented. In another embodiment, the flavivirus infection is treated.

A fourth aspect relates to a method of inhibiting viral replication. The method includes contacting one or more cells that have been infected with a virus with an effective amount of a compound of formulae (Ia)-(Ip):

(Ia)

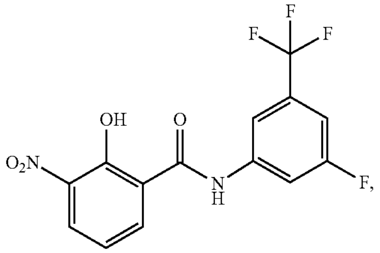

(Ib)

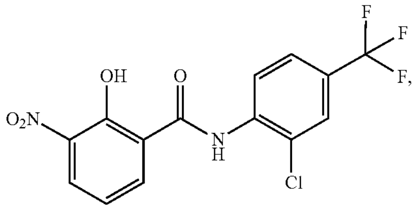

(Ic)

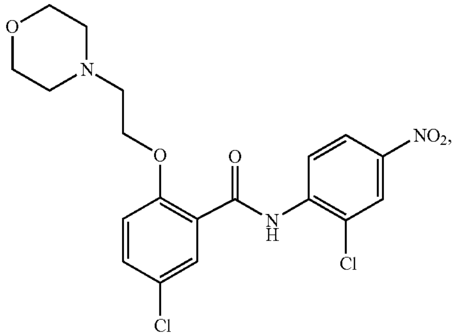

(Id)

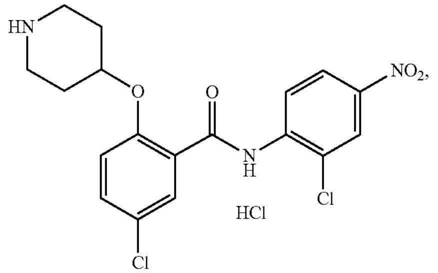

(Ie)

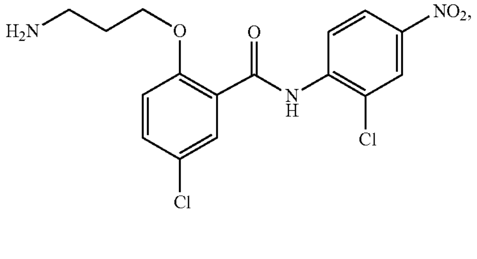

-continued (If)

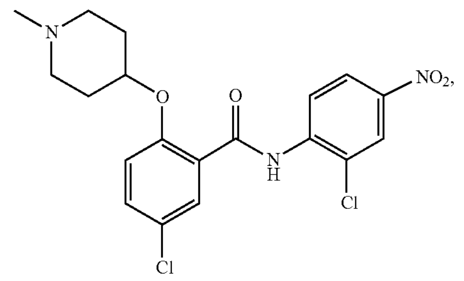

(Ig)

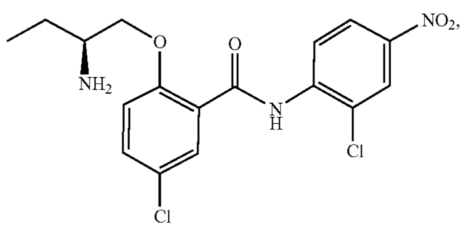

(Ih)

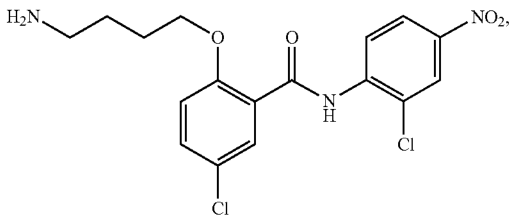

(Ii)

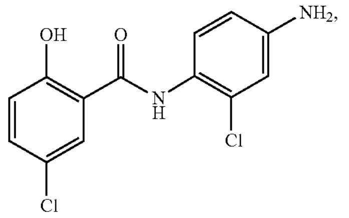

(Ij)

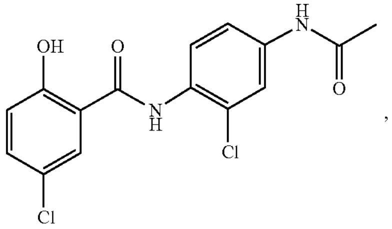

(Ik)

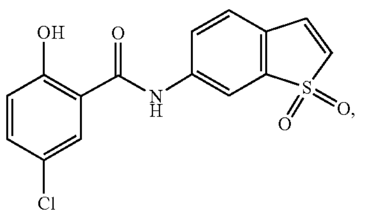

(Il)

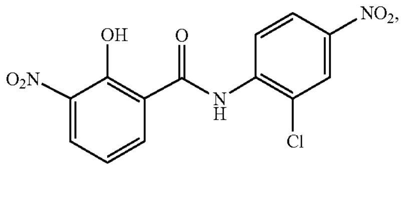

-continued (Im)

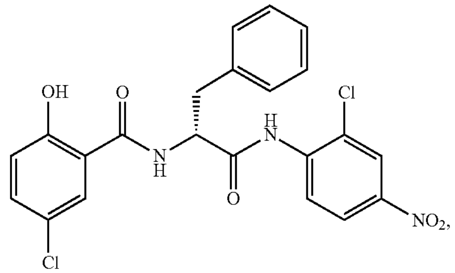

(In)

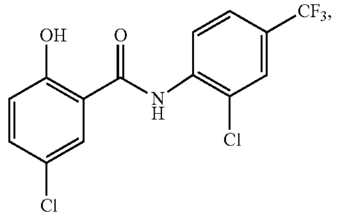

(Io)

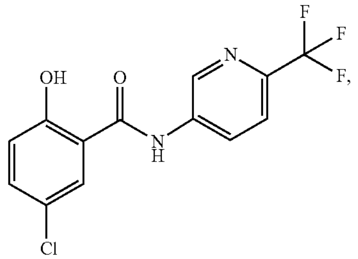

(Ip)

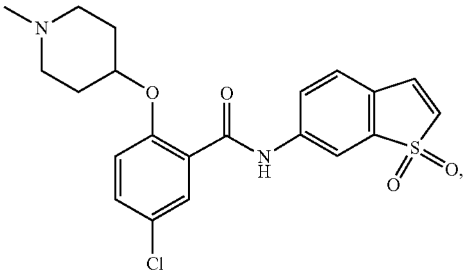

or a pharmaceutically acceptable salt thereof, wherein the virus comprises a flavivirus.

This aspect is carried out in accordance with the previously described aspects.

In another aspect, any of the foregoing compounds may be used in accordance with the present disclosure to prevent replication of a flavivirus, such as one of the types of flaviviruses identified in the above paragraphs. For example, such a flavivirus or a cell infected with such a flavivirus may be contacted with an amount of an anti-flavivirus compound of the present disclosure, or a pharmaceutically acceptable salt of the compound, optionally in combination with a pharmaceutically acceptable excipient, carrier, or additive, sufficient to prevent flaviviral replication, to prevent flaviviral replication. Use of any one or more of the foregoing compounds to prevent replication of one or more flaviviruses, including those specifically identified above, is explicitly contemplated and hereby included in the present disclosure.

In yet another aspect, any of the foregoing compounds may be used in accordance with the present disclosure to prevent protease activity of a flavivirus, such as one of the types of flaviviruses identified in the above paragraphs. For example, such a flavivirus or a cell infected with such a flavivirus may be contacted with an amount of an anti-flavivirus compound of the present disclosure, or a pharmaceutically acceptable salt of the compound, optionally in combination with a pharmaceutically acceptable excipient, carrier, or additive, sufficient to prevent protease activity of a flavivirus, such as NS2B/NS3 protease activity, to prevent protease activity of a flavivirus. Use of any one or more of the foregoing compounds to prevent protease activity of one or more flaviviruses, including those specifically identified above, is explicitly contemplated and hereby included in the present disclosure.

In the following description, reference is made to the accompanying drawings that form a part hereof, and in which is shown by way of illustration specific embodiments which may be practiced. These embodiments are described in detail to enable those skilled in the art to practice the disclosure, and it is to be understood that other embodiments may be utilized and that structural, logical and electrical changes may be made without departing from the scope of the present disclosure. The following description of example embodiments is, therefore, not to be taken in a limited sense.

The present disclosure may be further illustrated by reference to the following examples. The examples are intended to illustrate, but by no means are intended to limit, the scope of the present disclosure as set forth in the appended claims.

EXAMPLES

The following examples are intended to illustrate, but by no means are intended to limit, the scope of the present disclosure as set forth in the appended claims.

Example 1—Materials and Methods

Synthesis of niclosamide derivatives—The synthetic route of compound JMX0207 was described as below (Scheme 1), and the synthesis of other niclosamide derivatives was reported in previous publications. Xu et al., "Discovery of Niclosamide and its O-alkylamino-tethered Derivatives as Potent Antibacterial Agents Against Carbapenemase-producing and/or Colistin Resistant Enterobacteriaceae Isolates," *Bioorg. Med Chem. Lett.* 29:1399-1402 (2019); Chen et al., "Discovery of Potent Anticancer Agent HJC0416, An Orally Bioavailable Small Molecule Inhibitor of Signal Transducer and Activator of Transcription 3 (STAT3)," *Eur. J. Med Chem.* 82:195-203 (2014); Chen et al., "Discovery of O-Alkylamino Tethered Niclosamide Derivatives as Potent and Orally Bioavailable Anticancer Agents," *ACS Med Chem. Lett.* 4:180-185 (2013); and Chen et al., "Fragment-based Drug Design and Identification of HJC0123, a Novel Orally Bioavailable STAT3 Inhibitor for Cancer Therapy," *Eur. J. Med Chem.* 62:498-507 (2013), all of which are hereby incorporated by reference in their entirety.

The structures and purity of all synthesized compounds were confirmed by 1H and 13C NMR, HRMS and HPLC analysis, and all biologically evaluated compounds are >95% pure.

JMX0207 Synthesis.

Scheme 1. JMX0207 synthesis route.

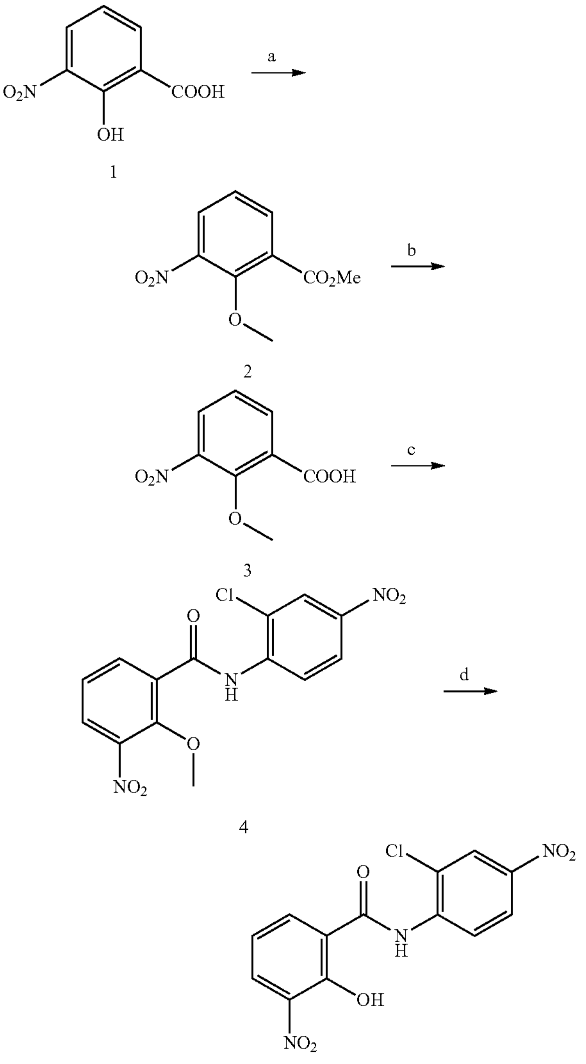

1

2

3

4

JMX0207

Reagents and conditions: (a) $CH_3I$, $K_2CO_3$, DMF, 50° C., 24 h, 95%. (b) NaOH, $H_2O$/MeOH, r.t., 1 h, 93%. (c) 2-chloro-4-nitroaniline, $POCl_3$, pyridine, DCM, 0° C. to r.t., 8 h, 67%. (d) $BBr_3$, DCM, 0° C. to r.t., 12 h, 96%.

Methyl 2-methoxy-3-nitrobenzoate (2). $CH_3I$ (3.9 g, 27.3 mmol) was added to a solution of 3-nitrosalicylic acid (1.0 g, 5.5 mmol) and $K_2CO_3$ (2.3 g, 16.4 mmol) in 20 mL of DMF. The mixture was stirred at 50° C. for 24 hrs and then diluted with 300 mL of AcOEt. The resulting mixture was washed with water (3x70 mL) and brine (50 mL), dried over $Na_2SO_4$, and concentrated in vacuo. The residue was purified by silica gel column (Hexane/EtOAc=2/1) to afford compound 2 (1.1 g, 95%) as a yellow oil. $^1H$ NMR (300 MHz, $CDCl_3$) δ 8.01-7.89 (m, 1H), 7.85-7.78 (m, 1H), 7.23-7.09 (m, 1H), 3.91 (s, 3H), 3.87 (s, 3H). $^{13}C$ NMR (75 MHz, $CDCl_3$) δ 164.6, 153.1, 145.4, 135.5, 128.3, 127.2, 123.7, 64.1, 52.6.

2-Methoxy-3-nitrobenzoic acid (3). NaOH (1.1 g, 27.3 mmol, in 6 mL of $H_2O$) was added to a solution of compound 2 (1.1 g, 5.5 mmol) in 10 mL of MeOH. The mixture was stirred at r.t. for 1 h, and then the pH value was adjusted to 5-6 with 1 M HCl (aq.). The mixture was extracted with EtOAc (2×120 mL) and washed with water (80 mL) and brine (60 mL), dried over $Na_2SO_4$, and concentrated to give acid 3 (1.0 g, 93%) as a light yellow solid for direct use in the next step.

N-(2-Chloro-4-nitrophenyl)-2-methoxy-3-nitrobenzamide (4). $POCl_3$ (3.9 g, 25.4 mmol) was added slowly at 0° C. to a solution of compound 3 (1.0 g, 5.1 mmol), 2-chloro-4-nitroaniline (876 mg, 5.1 mmol) and pyridine (8.0 g, 101.4 mmol) in 50 mL of DCM. After addition, the mixture was stirred at r.t. for 8 h and then poured into 200 mL of ice-water. Compound 4 (1.2 g, 67%) was isolated by filtration as a yellow solid. $^1H$ NMR (300 MHz, $CDCl_3$) δ 10.58 (s, 1H), 8.93 (d, J=9.3 Hz, 1H), 8.46 (dd, J=7.8, 1.8 Hz, 1H), 8.37 (d, J=2.7 Hz, 1H), 8.24 (dd, J=9.3, 2.4 Hz, 1H), 8.06 (dd, J=8.1, 1.8 Hz, 1H), 7.46 (t, J=8.1 Hz, 1H), 4.12 (s, 3H). $^{13}C$ NMR (75 MHz, $CDCl_3$) δ 161.9, 151.7, 144.4, 143.6, 140.7, 137.0, 129.9, 128.2, 125.3, 125.1, 123.8, 123.1, 121.1, 64.9.

N-(2-Chloro-4-nitrophenyl)-2-hydroxy-3-nitrobenzamide (JMX0207). $BBr_3$ (7.4 ml, 7.40 mmol, 1M in DCM) was added dropwise at 0° C. to a solution of compound 4 (1.3 g, 3.70 mmol) in 250 mL of DCM. The mixture was stirred at r.t. for 2 h. Then the mixture was poured into 200 mL of ice water. The yellow precipitate JMX0207 was isolated by filtration. The organic layer was separated and concentrated. Then 50 mL of MeOH was added and the mixture was stirred at r.t for 20 min. The yellow solid was isolated by filtration. The two parts of yellow solids were combined to afford 1.2 g (96%) of compound JMX0207 in total. HPLC purity 99.9% ($t_R$=18.75 min). $^1H$ NMR (300 MHz, DMSO-$d_6$) δ 12.10 (s, 1H), 8.65 (d, J=9.3 Hz, 1H), 8.42 (d, J=2.4 Hz, 1H), 8.34-8.24 (m, 2H), 8.13 (d, J=8.1 Hz, 1H), 7.03 (t, J=7.8 Hz, 1H). $^{13}C$ NMR (75 MHz, DMSO-$d_6$) δ 164.2, 154.1, 143.1, 141.3, 139.1, 136.3, 129.8, 124.8, 124.1, 123.6, 122.5, 122.4, 117.3. HRMS (ESI) calcd for $C_{13}H_9ClN_3O_6$ 338.0180 $(M+H)^+$, found 338.0172.

Cloning, Expression and Purification. All clones and proteins were generated as previously described. Li et al., "Existing Drugs as Broad-Spectrum and Potent Inhibitors for Zika Virus by Targeting NS2B-NS3 Interaction," *Cell Res.* 27:1046-1064 (2017) and Li et al., "Erythrosin B is a Potent and Broad-Spectrum Orthosteric Inhibitor of the Flavivirus NS2B-NS3 Protease," *Antiviral Res.* 150:217-225 (2018), both of which are hereby incorporated by reference in their entirety.

Split Luciferase Complementation (SLC) Assay. The SLC assay was performed as previously described. Li et al., "Existing Drugs as Broad-Spectrum and Potent Inhibitors for Zika Virus by Targeting NS2B-NS3 Interaction," *Cell Res.* 27:1046-1064 (2017); Li et al., "Erythrosin B is a Potent and Broad-Spectrum Orthosteric Inhibitor of the Flavivirus NS2B-NS3 Protease," *Antiviral Res.* 150:217-225 (2018); and Lang et al., "Analysis of Protein-Protein Interactions by Split Luciferase Complementation Assay," *Curr. Protoc. Toxicol.* 82:e (2019), all of which are hereby incorporated by reference in their entirety.

Protease Inhibition Assay. The protease inhibition assay was performed using the refolded DENV2 NS3 fusion protein (50 nM) and a fluorescence resonance energy transfer (FRET) peptide substrate (100 μM) (Abz-RRRRSAG-nTyr (NeoBiolab)), as described previously. Li et al., "Existing Drugs as Broad-Spectrum and Potent Inhibitors for Zika Virus by Targeting NS2B-NS3 Interaction," *Cell Res.* 27:1046-1064 (2017); Li et al., "Erythrosin B is a Potent and Broad-Spectrum Orthosteric Inhibitor of the Flavivirus NS2B-NS3 Protease," *Antiviral Res.* 150:217-225 (2018); Brecher et al., "A Conformational Switch High-Throughput Screening Assay and Allosteric Inhibition of the Flavivirus NS2B-NS3 Protease," *PLoS Pathog.* 13:e1006411 (2017); and Lang et al., "Analysis of Protein-Protein Interactions by Split Luciferase Complementation Assay," *Curr. Protoc. Toxicol.* 82:e (2019), all of which are hereby incorporated by reference in their entirety. Substrate cleavage was monitored at excitation/emission wavelengths of 360 nm/420 nm (Abz substrate) by a BioTek Flx800. The rate of increase in relative fluorescence unit (RFU) over time was calculated in the linear range and normalized as a percent of the DMSO control. The $IC_{50}/CC_{50}/EC_{50}$ was determined by fitting the dose-responsive curve with a non-linear regression function using the GraphPad Prism 8 (San Diego, Calif.). All experiments were performed in triplicates.

Cytotoxicity Assay. Cytotoxicity was measured by a WST-8 cell proliferation assay kit (Dojindo Molecular Technologies, Inc.) as previously described. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. All experiments were performed in triplicates.

Viral Titer Reduction Assay. A viral titer reduction assay was used to determine the compounds' effect on DENV2 and ZIKV strains, as described previously. Li et al., "Existing Drugs as Broad-Spectrum and Potent Inhibitors for Zika Virus by Targeting NS2B-NS3 Interaction," *Cell Res.* 27:1046-1064 (2017) and Li et al., "Erythrosin B is a Potent and Broad-Spectrum Orthosteric Inhibitor of the Flavivirus NS2B-NS3 Protease," *Antiviral Res.* 150:217-225 (2018), which are hereby incorporated by reference in their entirety. Human A549 lung carcinoma cells and human primary neural progenitor cells were used, as described previously. Li et al., "Erythrosin B is a Potent and Broad-Spectrum Orthosteric Inhibitor of the Flavivirus NS2B-NS3 Protease," *Antiviral Res.* 150:217-225 (2018); Brecher et al., "A Conformational Switch High-Throughput Screening Assay and Allosteric Inhibition of the Flavivirus NS2B-NS3 Protease," *PLoS Pathog.* 13:e1006411 (2017), which are hereby incorporated by reference in their entirety. All experiments were performed in triplicates.

Immunofluorescence Assay. The immunofluorescence assay was performed using ZIKV-infected cells treated with DMSO or JMX0207, as described previously. Li et al., "Existing Drugs as Broad-Spectrum and Potent Inhibitors for Zika Virus by Targeting NS2B-NS3 Interaction," *Cell Res.* 27:1046-1064 (2017); Li et al., "Erythrosin B is a Potent and Broad-Spectrum Orthosteric Inhibitor of the Flavivirus NS2B-NS3 Protease," *Antiviral Res.* 150:217-225 (2018), which are hereby incorporated in their entirety. A mouse monoclonal pan anti-E antibody 4G2 (ATCC) and a DyLight® 488 goat anti-mouse IgG (ImmunoReagents, Inc.) were used to monitor viral E protein expression, as described previously. Li et al., "Existing Drugs as Broad-Spectrum and Potent Inhibitors for Zika Virus by Targeting NS2B-NS3 Interaction," *Cell Res.* 27:1046-1064 (2017); Li et al., "Erythrosin B is a Potent and Broad-Spectrum Orthosteric Inhibitor of the Flavivirus NS2B-NS3 Protease," *Antiviral Res.* 150:217-225 (2018), which are hereby incorporated in their entirety.

Quantitative qRT-PCR. Quantitative qRT-PCR was performed as described previously. Li et al., "Existing Drugs as Broad-Spectrum and Potent Inhibitors for Zika Virus by Targeting NS2B-NS3 Interaction," *Cell Res.* 27:1046-1064 (2017); Li et al., "Erythrosin B is a Potent and Broad-Spectrum Orthosteric Inhibitor of the Flavivirus NS2B-NS3 Protease," *Antiviral Res.* 150:217-225 (2018), which are hereby incorporated in their entirety. ZIKV primers CCGCTGCCCAACACAAG (SEQ ID NO: 12) and CCACTAAYGTTCTTTTGCAGACAT (SEQ ID NO: 13) with ZIKV probe Cy5-AGCCTACCT/TAO/TGACAAGCAGTCAGACACTCAA-IAbRQSp (SEQ ID NO: 14) were used. The 2-ΔΔCT ("delta-delta Ct") method was used to quantify samples. All experiments were performed in triplicates.

Western Blot. Western blot was performed using anti-ZIKV NS3 (GTX133309, GeneTex, Inc.) and anti-GAPDH (CB1001, EMD Millipore) antibodies, as described previously. Li et al., "Existing Drugs as Broad-Spectrum and Potent Inhibitors for Zika Virus by Targeting NS2B-NS3 Interaction," *Cell Res.* 27:1046-1064 (2017) and Brecher et al., "A Conformational Switch High-Throughput Screening Assay and Allosteric Inhibition of the Flavivirus NS2B-NS3 Protease," *PLoS Pathog.* 13:e1006411 (2017), both of which are hereby incorporated by reference in their entirety. All experiments were performed in triplicates.

DENV2 Replicon Assay. BHK-21 cells stably expressing DENV2 replicon with a *Renilla* luciferase (Rluc) reporter gene (Boonyasuppayakorn et al., "Amodiaquine, an Antimalarial Drug, Inhibits Dengue Virus Type 2 Replication and Infectivity," *Antiviral Res.* 106:125-134 (2014), which is hereby incorporated by reference in its entirety) were seeded into white 96-well plate at a density of $2\times10^5$ cells per well. The cells were incubated at 37° C. in a humidified incubator with 5% $CO_2$ for hrs in a 100 μl medium containing Minimal Essential Medium (MEM) supplemented with 10% fetal bovine serum (FBS), 100 I.U./ml penicillin, 100 g/ml streptomycin, and 300 μg/ml G418. Upon 24 hrs incubation, culture medium was discarded. Fresh culture medium of 100 μl with a concentration series of compounds or DMSO control was added to the cells in triplicates. The culture was further incubated for 48 hours. The cells were then washed twice with 100 μl phosphate-buffered saline (PBS), followed by addition of 25 μl of a lysis buffer containing 1×PBS and 1% Triton X-100. The mixture was incubated at room temperature with gentle shaking (50 rpm) for 30 minutes. Assay buffer (125 μl) containing 1×PBS, 0.05% (3-((3-cholamidopropyl) dimethylammonio)-1-propanesulfonate) (CHAPS), and 0.1% BSA was then added to each well. In the meantime, a fresh 4× working substrate coelenterazine was prepared by diluting 1 μl of stock coelenterazine (2.4 mM) dissolved in ethanol into 10 ml assay buffer (10,000-fold dilution). Finally, 50 μl 4× substrate coelenterazine was added to each well with a final substrate concentration of 0.06 μM, using a Veritas luminometer. The luminescence was recorded immediately using the Veritas luminometer. The luminescence data was normalized to DMSO control. The $EC_{50}$ was determined by nonlinear regression fitting of normalized experimental data in GraphPad Prism 8.0 (San Diego, Calif.). All experiments were performed in triplicates.

Docking. The crystal structure of NS3pro of DENV2 (PDB Code: 2FOM) was downloaded from RCSB PDB bank. After excluding the cofactor NS2B peptide, the structure was preprocessed and optimized with Schrödinger Protein Preparation Wizard using default settings. The 3D structure of JMX0207 and niclosamide were created using Schrödinger Maestro and prepared with LigPrep to generate a low energy conformation suitable for docking. The Induced Fit Docking (IFD) protocol of Schrödinger Small-Molecule Drug Discovery Suite was employed in this docking study. The grid box for docking was centered on the 2B53 binding site. The box size was set to 20 Å on each side. Selected side chains of R24, K26, and M59 were temporarily trimmed (the equivalent of being mutated to alanine) during the initial IFD process and were restored later. The receptor-ligand complexes structures generated from IFD docking were imported into Schrödinger Maestro for visualization and analysis of binding site interactions.

Surface Plasmon Resonance. Surface plasmon resonance (SPR) was used to determine the affinity and kinetic analyses of the interactions between JMX0207 and the MBP-NS3 proteins at 25° C. using a ProteOn XPR36 SPR instrument (Bio-Rad). The MBP-NS3 wild-type or mutant proteins were immobilized onto a ProteOn™ GLH sensor chip (~9,000 RU) (Bio-Rad). A 2-fold dilution series of compounds were injected as the analytes. A blank surface blocked by ethanolamine was used as the control surface. The experiment was carried out at a flow rate of 100 μl/min using a PBSTD buffer containing 1×PBS, 0.005% surfactant P20, and 5% DMSO. Association ($k_a$) and dissociation ($k_d$) rates, as well as the dissociation constant ($K_D$), were obtained by global fitting of the SPR data from multiple concentrations to a simple 1:1 *Langmuir* binding model, using the ProteOn Manager software suite (Bio-Rad).

Culturing of human iPSCs. Human iPSC F11350.1 culture was maintained in feed-free conditions using mTeSR1 medium (StemCell Technologies #85851) with 5× supplement (StemCell Technologies #85852). Cells were maintained on six-well plates coated with human embryonic stem cell-qualified Matrigel at a 1:60 dilution (Corning Catalog #354277) and passaged with ReLeSR (StemCell Technologies #05872). Cortical 3D organoids were generated based on the protocol described by Yoon et al. Yoon et al., "Reliability of Human Cortical Organoid Generation," *Nat. Methods.* 16:75-78 (2019), which is hereby incorporated by reference in its entirety. Briefly, iPSCs were dissociated with accutase (ThermoFisher #A1110501) and then plated at a density of $3\times10^6$ cells per well in AggreWell 800 24-well plate (StemCell Technologies #34811) in Essential 8™ medium (ThermoFisher #A1517001) supplemented with 10 μM rock inhibitor (Tocris #Y27632). The plate was centrifuged at 100×g for 3 min and incubated at 37° C. overnight. The next day (culture day 0) the organoids were transferred to a low attachment 10 cm plate (Corning #3262) and maintained in 10 mL of neural induction medium (Essential 6™ medium, Life Technologies, #A1516401) supplemented with two SMAD pathway inhibitors, 10 μM SB431541 (R&D #1614/50) and 2.5 μM dorsomorphin (Tocris #3093), and Wnt pathway inhibitor 2.5 μM XAV-939 (Tocris #XAV-939). Media were exchanged daily. On day 6, the medium was changed to neural expansion medium (Neuralbasal A medium, ThermoFisher #10888) supplemented with 2% B27 (without Vit A; ThermoFisher #12587001), 1% antibiotic-antimycotic (ThermoFisher #15240062), 1% glutaMAX (ThermoFisher #35050061), 20 ng/mL FGF2 (R&D #233-FB-500) and 20 ng/mL EGF2 (PeproTech #AF-100-15). Media were exchanged daily.

Cryopreservation. Organoids were fixed in 4% paraformaldehyde (Santa Cruz) overnight at 4° C. They were then washed three times in PBS and transferred to 30% sucrose solution for 72 h. Organoids were then transferred into plastic cryomold (10×10×5 mm; Tissue Tek cat. no. 4565) with embedding medium (Tissue-Tek OCT compound, Sakura Finetek 4583) and stored at −80° C. For immunohistochemistry, 20 m thick sections were cut with a Leica cryostat (model CM3050S).

Immunohistochemistry. Cryosections were blocked in 3% bovine serum albumin (BSA), 10% normal goat serum (NGS), and 0.3% Triton X-100 diluted in PBS for 1 hour at room temperature. The sections were incubated overnight at 4° C. with primary antibodies diluted in blocking solution. Sections were washed three times with PBS and then incubated with appropriate secondary antibodies diluted in blocking solution for 1 hour. The following primary antibodies were used for immunohistochemistry: anti-Pax-6 (1:200; Biolegend #901301), anti-Sox2 (1:100; Santa Cruz #sc-365823), anti-FoxG1 (1:500; Takara #M227), Sox10 (1:100; Santa Cruz #sc369692), and anti-tubulin III (1:1000; Sigma #T8660).

Pharmacokinetics. Two- to three-month-old female B6 mice were used for the study. Four to five mice per group were given niclosamide at 40 mg/kg (in 1% DMSO and 0.5% carboxymethylcellulose) or JMX0207 in the same vehicle at the indicated dose by oral gavage. Sample preparation and liquid chromatography with tandem mass spectrometry (LC-MS/MS) detection of niclosamide and JMX0207 were essentially the same as described in a previous study and were performed using a Sciex 4000 Q-Trap mass spectrometer (AB SCIEX, Framingham, Mass.) with the Agilent 1200 high-performance liquid chromatography system (Agilent Technologies, Santa Clara, Calif.). Fan et al., "Contributions of Hepatic and Intestinal Metabolism to the Disposition of Niclosamide, a Repurposed Drug with Poor Bioavailability," *Drug Metab. Dispos.* 47:756-763 (2019), which is hereby incorporated by reference in its entirety. JMX0207 was monitored at m/z 336/171. Declustering potential, entrance potential, collision energy, and collision cell exit potential were optimized for detection and quantification of JMX0207 at −45, −10, −35, and −14V, respectively. Data from 4 or 5 mice at each time point were averaged and used to calculate pharmacokinetic parameters, using a pharmacokinetic solver (Microsoft, Redmond, Wash.) by assuming a noncompartmental model. Statistical significance of various data comparisons was determined with the use of GraphPad Prism (GraphPad Software, La Jolla, Calif.). Student's t-test was used. P values<0.05 were considered statistically significant.

In vivo protection efficacy. All animal studies involving infectious ZIKV were conducted at an Animal Biosafety Level 2 (ABSL-2) facility at the Wadsworth Center with Institutional Biosafety and Animal Welfare Committee approval. The in vivo antiviral activity of JMX0207 was evaluated in a viremia animal model.

A group of four-week-old A129 mice were infected by subcutaneous injection with $1.7\times10^5$ PFU of the PRVABC59 strain. Then, the infected mice were administered JMX0207 at 20 mg/kg of body weight (n=10) or with vehicle control (n=10) every day for 3 consecutive days post-infection (dpi). Mice were observed daily for signs of illness and mortality. Viremia on day 3 post-infection (pi) was determined by plaque forming assay, and statistical analysis was performed using the unpaired, two-tailed t-test (Prism).

Example 2—Synthesis and Screening of Niclosamide Derivatives

Niclosamide was originally used as an anthelmintic drug. It was also found to have anti-cancer and antibacterial activities. Burock et al., "Phase II Trial to Investigate the Safety and Efficacy of Orally Applied Niclosamide in Patients With Metachronous or Sychronous Metastases of a Colorectal Cancer Progressing After Therapy: The NIKOLO Trial," *BMC Cancer* 18:297 (2018); Barbosa et al., "Niclosamide Repositioning for Treating Cancer: Challenges and Nano-Based Drug Delivery Opportunities," *Eur. J. Pharm. Biopharm.* 141:58-69 (2019); Chen et al., "Niclosamide: Beyond an Antihelminthic Drug," *Cell Signal* 41:89-96 (2018); Fan et al., "Dual Activity of Niclosamide to Suppress Replication of Integrated HIV-1 and *Mycobacterium tuberculosis* (Beijing)," *Tuberculosis* (*Edinb*) 116S:S28-S33 (2019); and Xu et al., "Discovery of Niclosamide and its O-alkylamino-tethered Derivatives as Potent Antibacterial Agents Against Carbapenemase-producing and/or Colistin Resistant Enterobacteriaceae Isolates," *Bioorg. Med. Chem. Lett.* 29:1399-1402 (2019), all of which are hereby incorporated by reference in their entirety. A small library composed of 62 niclosamide derivatives was previously developed for other purposes. Fan et al., "Dual Activity of Niclosamide to Suppress Replication of Integrated HIV-1 and *Mycobacterium tuberculosis* (Beijing)," *Tuberculosis* (*Edinb*) 116S:S28-S33 (2019); Xu et al., "Discovery of Niclosamide and its O-alkylamino-tethered Derivatives as Potent Antibacterial Agents Against Carbapenemase-producing and/or Colistin Resistant Enterobacteriaceae Isolates," *Bioorg. Med. Chem. Lett.* 29:1399-1402 (2019); Chen et al., "Discovery of Potent Anticancer Agent HJC0416, An Orally Bioavailable Small Molecule Inhibitor of Signal Transducer and Activator of Transcription 3 (STAT3)," *Eur. J. Med. Chem.* 82:195-203 (2014); Chen et al., "Discovery of O-Alkylamino Tethered Niclosamide Derivatives as Potent and Orally Bioavailable Anticancer Agents," *ACS Med. Chem. Lett.* 4:180-185 (2013); Wang et al., "Suppression of the Growth and Invasion of Human Head and Neck Squamous Cell Carcinomas via Regulating STAT3 Signaling and the miR-21/beta-catenin Axis with HJC0152," *Mol. Cancer Ther.* 16:578-590 (2017); and Chen et al., "Fragment-based Drug Design and Identification of HJC0123, a Novel Orally Bioavailable STAT3 Inhibitor for Cancer Therapy," *Eur. J. Med. Chem.* 62:498-507 (2013), all of which are hereby incorporated by reference in their entirety. These niclosamide analogs have been resynthesized in-house following published procedures for antiviral evaluation. To identify niclosamide derivatives that have equal or better antiviral efficacy and improved pharmacokinetic properties, SLC-based NS2B-NS3 interaction assay was used to screen this library, with niclosamide as a control.

TABLE 1
$IC_{50}$,[a] $EC_{50}$, $CC_{50}$ (all in μM), and therapeutic index (TI) of niclosamide derivatives.
| Compound[b] | Structure | $IC_{50\text{-}SLC\text{-}}$ (DN2) | $IC_{50\text{-}pro}$ (DN2) | $EC_{50\text{-}DN2}$ (A549) | $EC_{50\text{-}ZK}$ (A549) | $CC_{50}$ (A549) | TI[c] (DN2) | TI (ZK) |
|---|---|---|---|---|---|---|---|---|
| Niclosamide | 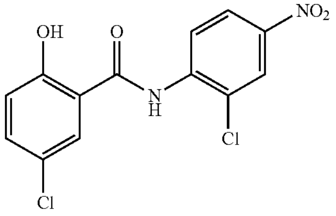 [SMILES: O=C(Nc1ccc([N+](=O)[O-])cc1Cl)c1cc(Cl)ccc1O] | 2.0 | 21.6 | 0.55 | 0.48 | 0.48 | 8.7 | 10.0 |
| HJC0114 | 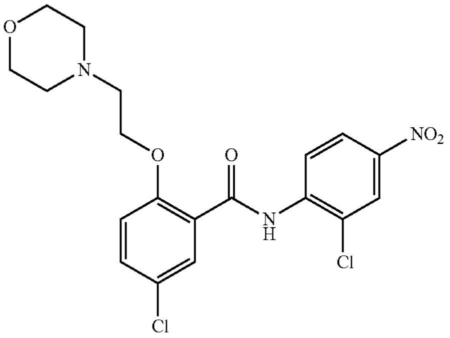 [SMILES: O=C(Nc1ccc([N+](=O)[O-])cc1Cl)c1cc(Cl)ccc1OCCN1CCOCC1] | 18.4 | 33.6 | >30 | >30 | >200 | | |
| HJC0125 | 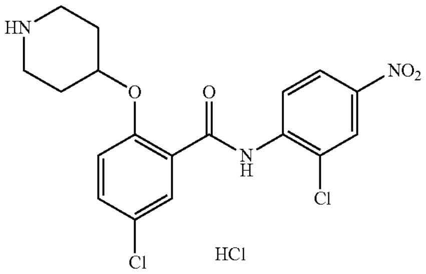 [SMILES: O=C(Nc1ccc([N+](=O)[O-])cc1Cl)c1cc(Cl)ccc1OC1CCNCC1 ; Cl] HCl | 16.3 | 44.5 | 0.21 | 0.15 | 50.2 | 239 | 335 |
| HJC0308 | 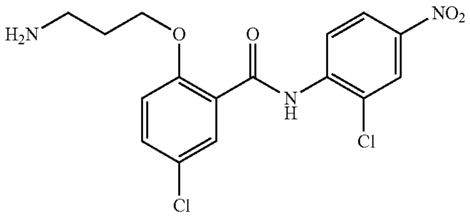 [SMILES: NCCCOc1ccc(Cl)cc1C(=O)Nc1ccc([N+](=O)[O-])cc1Cl] | 4.9 | 39.7 | 1.4 | 6.2 | 17.7 | 12.6 | 2.8 |
| HJC0365 | 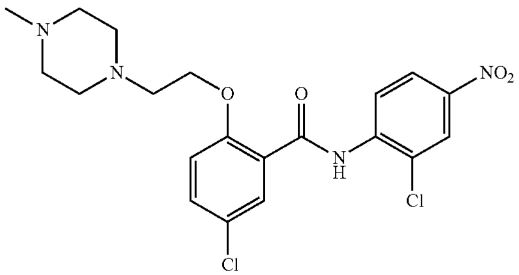 [SMILES: CN1CCN(CCOc2ccc(Cl)cc2C(=O)Nc2ccc([N+](=O)[O-])cc2Cl)CC1] | 13.2 | >60 | 6.4 | 6.0 | 177 | 27.6 | 29.5 |

TABLE 1-continued
$IC_{50}$,[a] $EC_{50}$, $CC_{50}$ (all in μM), and therapeutic index (TI) of niclosamide derivatives.
| Compound[b] | Structure | $IC_{50\text{-}SLC\text{-}}$ (DN2) | $IC_{50\text{-}pro}$ (DN2) | $EC_{50\text{-}DN2}$ (A549) | $EC_{50\text{-}ZK}$ (A549) | $CC_{50}$ (A549) | TI[c] (DN2) | TI (ZK) |
|---|---|---|---|---|---|---|---|---|
| HJC0381 | 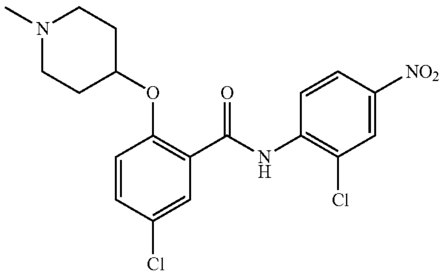 [SMILES: CN1CCC(Oc2ccc(Cl)cc2C(=O)Nc2ccc([N+](=O)[O-])cc2Cl)CC1] | 10.8 | 25.9 | 1.2 | 3.9 | 91.1 | 76 | 23.3 |
| HJC0390 | 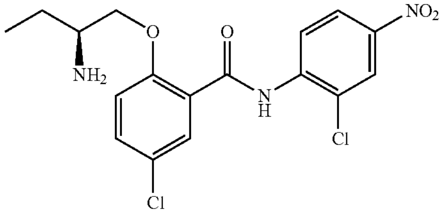 [SMILES: CC[C@H](N)COc1ccc(Cl)cc1C(=O)Nc1ccc([N+](=O)[O-])cc1Cl] | 6.0 | 46.5 | 0.43 | <0.1 | 30.1 | 70 | >300 |
| HJC0431 | 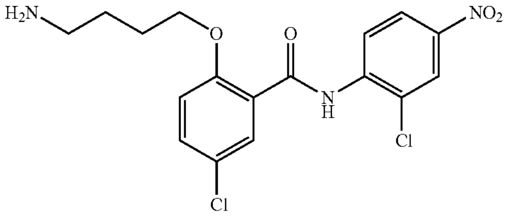 [SMILES: NCCCCOc1ccc(Cl)cc1C(=O)Nc1ccc([N+](=O)[O-])cc1Cl] | 3.1 | 34.0 | 2.2 | 0.36 | 28.4 | 13 | 79 |
| HJC0129 | 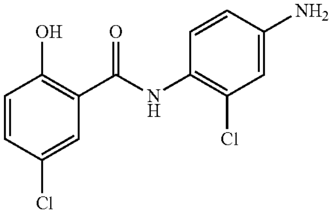 | 9.6 | 11.3 | >30 | >30 | 176 | | |
| HJC0140 | 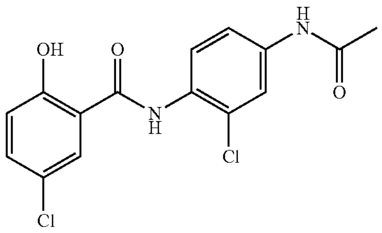 [SMILES: CC(=O)Nc1ccc(NC(=O)c2cc(Cl)ccc2O)c(Cl)c1] | 9.4 | 25.5 | >30 | >30 | >200 | | |
| HJC0149 | 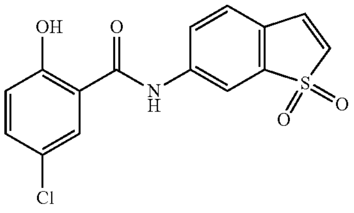 [SMILES: O=C(Nc1ccc2c(c1)S(=O)(=O)C=C2)c1cc(Cl)ccc1O] | 18.6 | 20.3 | 0.9 | 1.1 | 241 | 268 | 219 |

TABLE 1-continued $IC_{50}$,[a] $EC_{50}$, $CC_{50}$ (all in μM), and therapeutic index (TI) of niclosamide derivatives.

| Compound[b] | Structure | $IC_{50\text{-}SLC}$ (DN2) | $IC_{50\text{-}pro}$ (DN2) | $EC_{50\text{-}DN2}$ (A549) | $EC_{50\text{-}ZK}$ (A549) | $CC_{50}$ (A549) | TI[c] (DN2) | TI (ZK) |
| --- | --- | --- | --- | --- | --- | --- | --- | --- |
| JMX0207 | 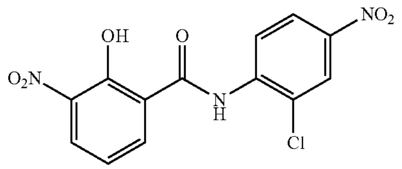 [SMILES: O=C(Nc1ccc([N+](=O)[O-])cc1Cl)c1cccc([N+](=O)[O-])c1O] | 1.3 | 8.2 | 0.31 | 0.30 | 31.9 | 103 | 106 |

[a]$IC_{50\text{-}SLC}$/$IC_{50\text{-}pro}$/$EC_{50}$/$CC_{50}$: Compound concentrations require to reduce 50% of the split luciferase complementation (SLC) signal, protease activity, virus production, and cell viability, respectively. [b]Original compound names from literature and this work. According to their structures, these compounds can be classified into three groups, colored as red, magenta, and blue, respectively. [c]TI, therapeutic index (TI) defined as CC50/EC50. All values are in micromolar (μM) except TI. DN2, Dengue virus serotype 2; ZK, Zika virus.

Eleven out of 62 niclosamide derivatives showed dose-responsive inhibition of the interaction between viral NS3 protease and its cofactor NS2B, with $IC_{50\text{-}SLC}$ values lower than 30 μM, the highest concentration tested ($IC_{50\text{-}SLC}$ $IC_{50\text{-}pro}$/$EC_{50}$/$CC_{50}$: compound concentrations required to reduce 50% of the split luciferase complementation signal, protease activity, virus production, and cell viability, respectively) (Table 1, FIGS. 1A-1B). The derivatives identified included seven compounds with O-alkylamino chains, one compound with 3-$NO_2$ instead of 5-Cl on the salicylic ring, and three compounds with modifications on the nitro group of the aniline moiety. Of these active derivatives, compounds HJC0308 with 3-aminopropoxy moiety, HJC0431 with 4-aminobutoxy moiety, and JMX0207 with 3-$NO_2$ group showed comparable or better inhibition of the NS2B-NS3 SLC with $IC_{50\text{-}SLC}$ values of 4.9 μM, 3.1 μM and 1.3 μM, respectively, compared to niclosamide.

Example 3—Inhibition of the NS2B-NS3 Protease Activity

Next, the inhibition efficacy of these positive derivatives were evaluated against the viral NS2B-NS3 protease function as previously described. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. Previously, two versions of the NS3 protease were generated, the NS3 protease domain refolded from inclusion bodies and a soluble version of the NS3 protease domain fused to maltose-binding protein (MBP). Li et al., "Existing Drugs as Broad-Spectrum and Potent Inhibitors for Zika Virus by Targeting NS2B-NS3 Interaction," *Cell Res.* 27:1046-1064 (2017) and Li et al., "Erythrosin B is a Potent and Broad-Spectrum Orthosteric Inhibitor of the Flavivirus NS2B-NS3 Protease," *Antiviral Res.* 150:217-225 (2018), both of which are hereby incorporated by reference in their entirety.

The data showed that the refolded and MBP-tagged NS3 proteins have indistinguishable protease activities when transactivated by co-factor NS2B. In this work, both versions were used to characterize the inhibitors and found that the $IC_{50}$ values determined from both versions were similar. Therefore, only values for the refolded NS3 were shown. As shown in Table 1, most active compounds in SLC assay except HJC0365 still showed inhibition against the viral NS2B-NS3 protease activity. However, it was found that there seemed to be no strict correlation between $IC_{50\text{-}SLC}$ and $IC_{50\text{-}pro}$ values. This is not surprising because niclosamide is a known luciferase inhibitor. Thorne et al., "Firefly Luciferase in Chemical Biology: A Compendium of Inhibitors, Mechanistic Evaluation of Chemotypes, and Suggested Use as a Reporter," *Chem. Biol.* 19:1060-1072 (2012), which is hereby incorporated by reference in its entirety. The SLC inhibition is an indirect readout of the NS2B-NS3 interactions. Direct inhibition of luciferase activity and/or direct inhibition of luciferase complementation in addition to inhibition of NS2B-NS3 interaction may account for the poor correlation between $IC_{50\text{-}SLC}$ and $IC_{50\text{-}pro}$ values. While $IC_{50\text{-}SLC}$ is a poor indicator of inhibition efficacy of the NS2B-NS3 interactions, it remains a valuable indicator to eliminate compounds if they failed to inhibit SLC.

Among these derivatives, compounds HJC0140 with 4'-acetamido group ($IC_{50\text{-}pro}$=25.5 μM), HJC0149 with benzo[b]thiophene 1,1-dioxide moiety ($IC_{50\text{-}pro}$=20.3 μM) and HJC0381 with (1-methylpiperidin-4-yl)oxy moiety ($IC_{50\text{-}pro}$=25.9 μM) maintained the same level of potency, while compounds HJC0129 with 4'-$NH_2$ group ($IC_{50\text{-}pro}$=11.3 μM) and JMX0207 with 3-$NO_2$ group ($IC_{50\text{-}pro}$=8.2 μM) showed nearly or more than 2-fold improvement in inhibition of the viral NS2B-NS3 protease activity, compared to niclosamide ($IC_{50\text{-}pro}$=21.6 μM) (Table 1, FIGS. 1A-1B). Taken together, the three compounds HJC0129 ($IC_{50\text{-}SLC}$=9.6 μM and $IC_{50\text{-}pro}$=11.3 μM), HJC0140 ($IC_{50\text{-}SLC}$=9.4 μM and $IC_{50\text{-}pro}$=25.5 μM), and JMX0207 ($IC_{50\text{-}SLC}$=1.3 μM and $IC_{50\text{-}pro}$=8.2 μM) showed potent inhibitory activity against the NS2B-NS3 interactions in both NS2B-NS3 SLC and NS2B-NS3 protease assays.

Example 4—Inhibition of DENV2 Viral Replication

Figures 2A, 2B:
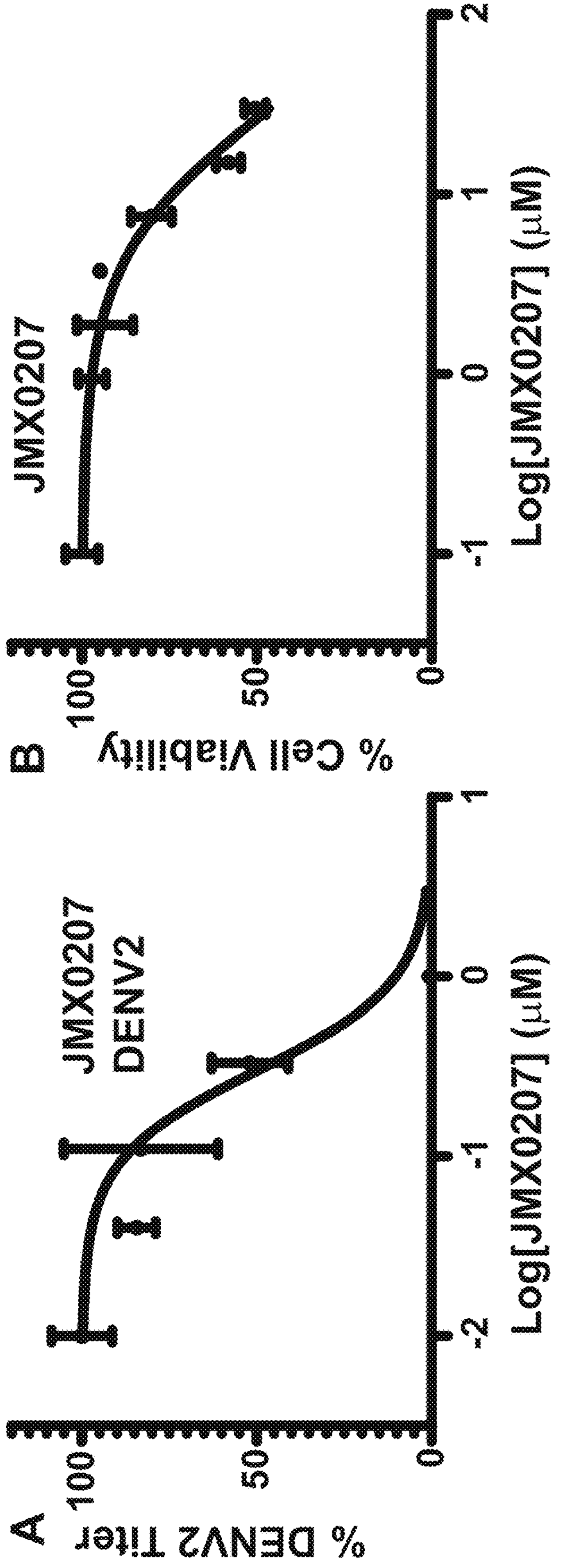
FIGS. 2A-2B show that JMX0207 inhibits DENV.

A viral plaque reduction assay was performed next to evaluate the antiviral efficacy of these derivatives. Human lung carcinoma A549 cells were infected with DENV2 in the presence of a concentration series of derivatives or a dimethyl sulfoxide (DMSO) control, and viral titers were measured at 48 hrs post-infection, as described previously. Li et al., "Existing Drugs as Broad-Spectrum and Potent Inhibitors for Zika Virus by Targeting NS2B-NS3 Interaction," *Cell Res.* 27:1046-1064 (2017); Li et al., "Erythrosin B is a Potent and Broad-Spectrum Orthosteric Inhibitor of the Flavivirus NS2B-NS3 Protease," *Antiviral Res.* 150:217-225 (2018); and Vernekar et al., "5'-Silylated 3'-1,2,3-triazolyl Thymidine Analogues as Inhibitors of West Nile Virus and Dengue Virus," *J. Med. Chem.* 58:4016-4028 (2015), all of which are hereby incorporated by reference in their entirety. The results indicated that eight out 11 active derivatives showed appreciable antiviral efficacy with $EC_{50\text{-}DN2}$ less than 30 μM (Table 1). The best derivative, JMX0207, showed slightly improved antiviral efficacy ($EC_{50\text{-}DN2}$ of 0.31 μM), compared to niclosamide ($EC_{50\text{-}DN2}$ of 0.55 μM) (FIG. 2A).

The observed antiviral activity could result from compound's cytotoxicity. To address this concern, next the compound cytotoxicity $CC_{50}$ was measured using a WST-8 cell proliferation assay, as described previously. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. As shown in Table 1 and FIG. 2B, the majority of these derivatives showed improved $CC_{50}$ and therapeutic index (defined as $CC_{50}/EC_{50}$), compared to niclosamide.

Figures 3A, 3B, 3C:
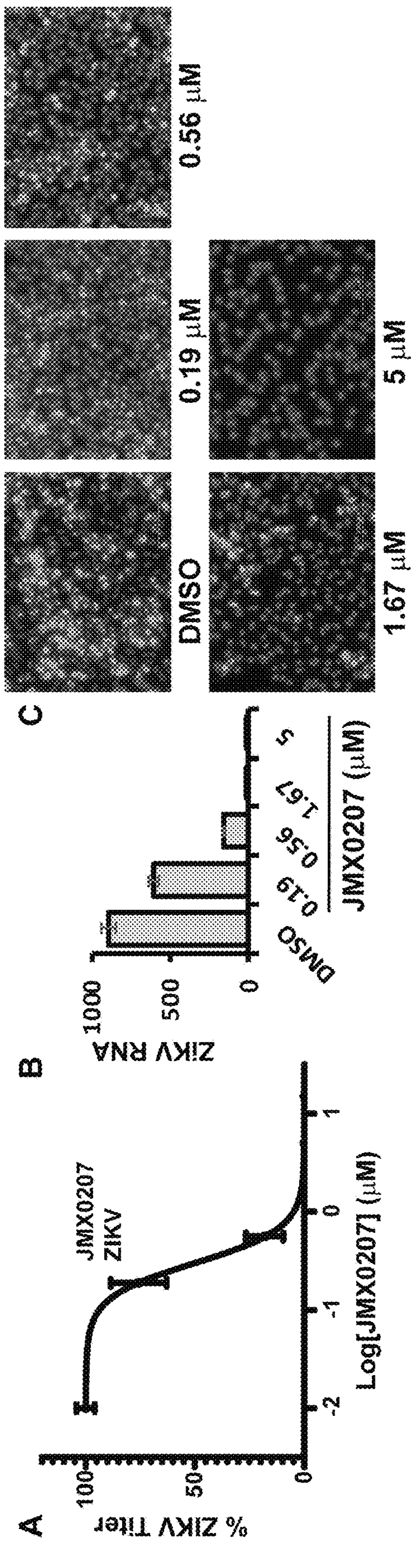
FIGS. 3A-3C show that JMX0207 inhibits ZIKV.

Example 5—JMX0207 Treatment Leads to Reductions in Viral RNA Yield and Protein Production Among the derivatives, JMX0207 showed improved efficacy in almost all categories (Table 1), compared to niclosamide. Therefore, JMX0207 was chosen to further characterize whether JMX0207 treatment led to inhibition of viral RNA synthesis and viral protein production, using qRT-PCR and immunofluorescence assay (IFA), respectively. The results indicated that JMX0207 significantly reduced the ZIKV RNA copy number in a dose-dependent manner (FIG. 3B). Using a pan flavivirus anti-E antibody 4G2, an IFA was conducted to demonstrate that JMX0207 greatly reduced ZIKV antigen production in A549 cells in a dose-dependent manner (FIG. 3C), presumably because of inhibition of viral replication.

Overall, these experimental results indicated that JMX0207 showed improved anti-protease, antiviral, and cytotoxicity properties, compared to niclosamide. JMX0207 treatment results in inhibition of viral infectivity, viral RNA replication, and viral protein production, and is a broad-spectrum antiviral for flaviviruses.

Example 6—JMX0207 Inhibits Viral Production in Cells Relevant to ZIKV Pathogenesis Next, human induced pluripotent stem cell (iPSC)-derived neural progenitor cell (HNPC) was used (Li et al., "Existing Drugs as Broad-Spectrum and Potent Inhibitors for Zika Virus by Targeting NS2B-NS3 Interaction," *Cell Res.* 27:1046-1064 (2017) and Chambers et al., "Highly Efficient Neural Conversion of human ES and iPS Cells by Dual Inhibition of SMAD Signaling," *Nat. Biotechnol.* 27:275-280 (2009), both of which are hereby incorporated by reference in their entirety) to investigate whether JMX0207 is an effective inhibitor in human primary cells demonstrated to be relevant to ZIKV pathogenesis. Tabata et al., "Zika Virus Targets Different Primary Human Placental Cells, Suggesting Two Routes for Vertical Transmission," *Cell Host Microbe.* 20:155-166 (2016); Tang et al., "Zika Virus Infects Human Cortical Neural Progenitors and Attenuates Their Growth," *Cell Stem Cell.* 18:587-590 (2016); Zhang et al., "Molecular Signatures Associated with ZIKV Exposure in Human Cortical Neural Progenitors," *Nucleic Acids Res.* 44:8610-8620 (2016); Qian et al., "Brain-Region-Specific Organoids Using Mini-bioreactors for Modeling ZIKV Exposure. *Cell.* 165:1238-1254 (2016); Garcez et al., "Zika Virus Impairs Growth in Human Neurospheres and Brain Organoids," *Science* 352:816-818 (2016), all of which are hereby incorporated by reference in their entirety. As shown (FIGS. 4A and 4B), JMX0207 effectively inhibited ZIKV protein expression and RNA synthesis in HNPC in dose-dependent manner. Overall, these experiments demonstrate that JMX0207 is an effective antiviral in neural progenitor cells relevant to ZIKV infection.

Example 7—JMX0207 Protects 3D Mini-brain Organoid From ZIKV Infection

Newborns from mothers with ZIKV infection during pregnancy have significantly increased risk of developing microcephaly, a birth defect where a baby has smaller than normal head circumference. Babies born with microcephaly may develop many brain-related or other neurological problems. Recently, neural stem cell-derived 3D cerebral organoids were used to dissect ZIKV pathogenesis and anti-viral development. Qian et al., "Brain-Region-Specific Organoids Using Mini-bioreactors for Modeling ZIKV Exposure. *Cell.* 165:1238-1254 (2016); Qian et al., "Using Brain Organoids to Understand Zika Virus-induced Microcephaly," *Development* 144:952-957 (2017); Xu et al., "Zika Virus Infection Induces RNAi-mediated Antiviral Immunity in Human Neural Progenitors and Brain Organoids," *Cell Res.* 29:265-273 (2019); and Li et al., "25-Hydroxycholesterol Protects Host against Zika Virus Infection and Its Associated Microcephaly in a Mouse Model," Immunity. 46:446-456 (2017), all of which are hereby incorporated by reference in their entirety. Compared to the cultured 2D monolayer cells, the 3D brain organoids can better represent the composition, diversity and organization of cell types found in the developing human brain.

Figures 4A, 4B, 4C, 4D, 4E, 4F:
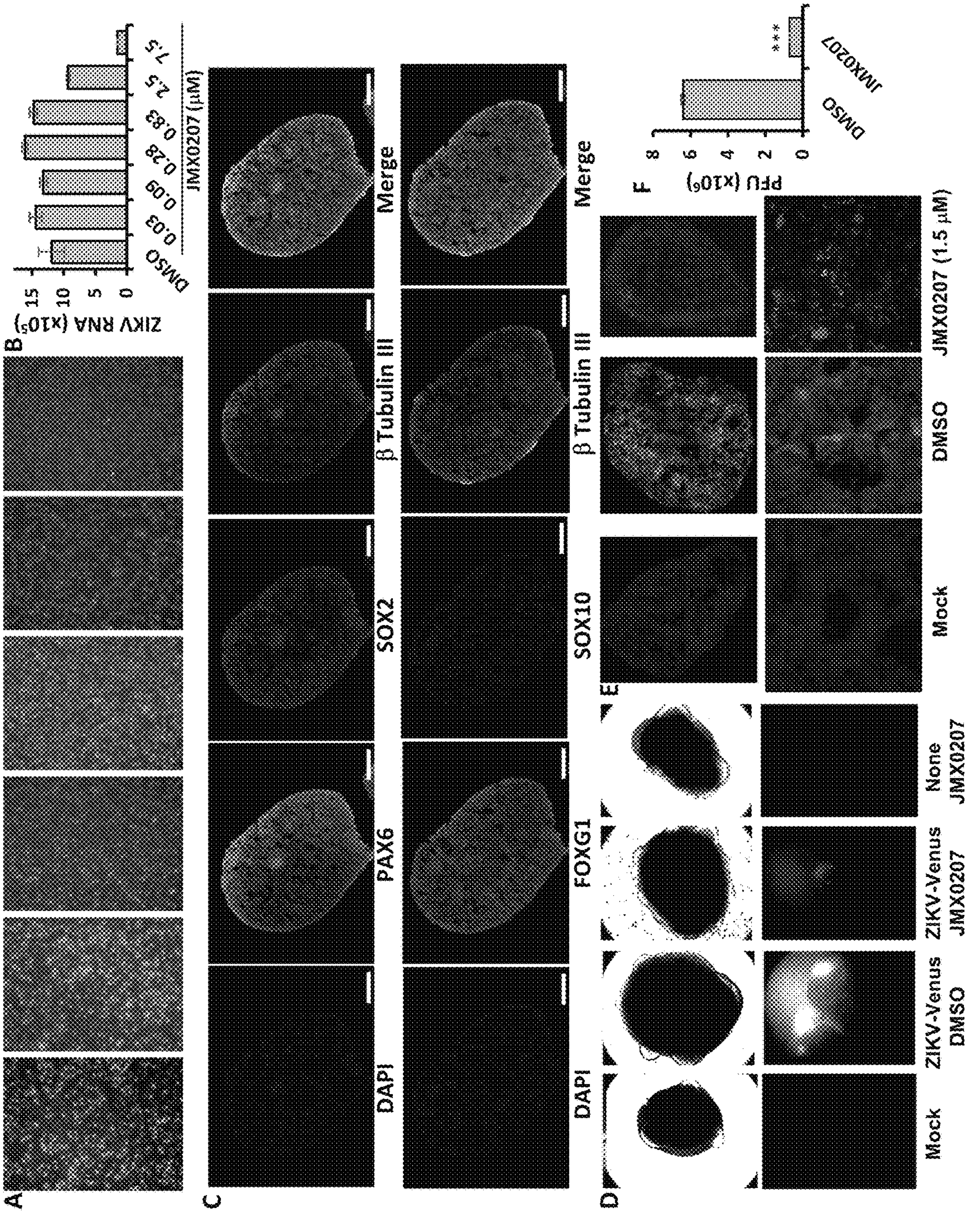
FIGS. 4A-4F show inhibition of ZIKV in cells relevant to ZIKV.

Therefore, the 3D mini-brain organoid model was used to further investigate whether JMX0207 can protect against ZIKV-associated neurological damage. Induced pluripotent stem cells (iPSC) derived from a healthy control (Male, Caucasian) were differentiated using an established protocol to generate region-specific organoids patterned to resemble the dorsal forebrain (FIG. 4C). Yoon et al., "Reliability of Human Cortical Organoid Generation," *Nat. Methods.* 16:75-78 (2019), which is hereby incorporated by reference in its entirety. Organoids were stained positive for forebrain identity markers PAX6 (dorsal forebrain progenitors; upper panel), FOXG1 (lower panel) and SOX2 (neural ectoderm marker, upper panel) at 20 days. The sections were stained positive for general neuronal marker TUJI (neuron-specific class III β-tubulin; upper and lower panels) and were negative for SOX10 (Neural crest, Red, lower panel).

To evaluate if JMX0207 protects organoids from ZIKV infections, a full-length infectious ZIKV clone expressing Venus fluorescent protein (ZIKV-Venus) was first generated. At day 20, the organoids displayed signature features of forebrain, including neural rosettes (FIGS. 4C-4E), and were pre-treated with JMX0207 (1.5 μM) or DMSO control. At day 20, the organoids were infected with either Mock or ZIKV strain PRVABC59 or ZIKV-Venus, at an estimated multiplicity of infection (MOI) of 1 in the presence of 1.5 μM JMX0207 or DMSO control. ZIKV infection was quantified by a plaque forming unit (PFU) assay at 5 dpi and by fluorescence imaging at 7 dpi, respectively. The results showed that JMX0207 at 1.5 μM concentration did not have any toxic effect on the 3D organoids, which remained intact and unchanged in morphology (FIG. 4D). Compared to DMSO control, JMX0207 treatment completely abolished ZIKV infection in the 3D organoid (FIG. 4D).

The 3D mini-brain organoids were sliced for immunostaining to investigate the antiviral effects of JMX0207 (FIG. 4E). As shown, untreated organoids (DMSO) were infected with ZIKV throughout all layers (FIG. 4E). In contrast, JMX0207 treatment nearly completely protected the organoids from ZIKV infection (FIG. 4E). Moreover, ZIKV production was also significantly inhibited by JMX0207 treatment (FIG. 4F). Collectively, the results indicated that JMX0207 is an effective inhibitor to protect developing human cortical tissue from ZIKV infection.

Example 8—JMX0207 Shows Improved Pharmacokinetic Properties

Figures 5A, 5B, 5C:
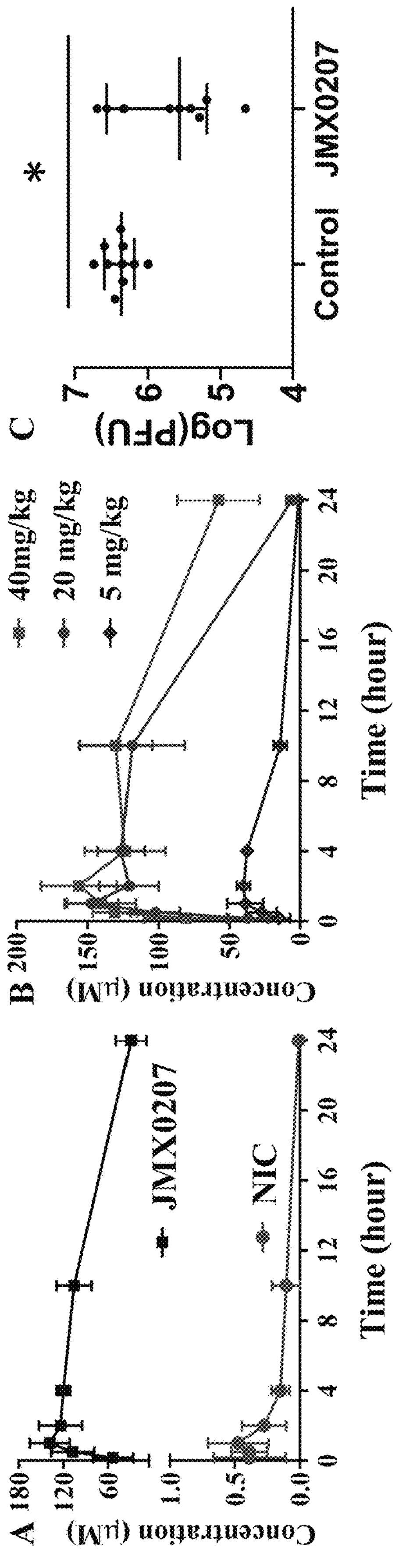
FIGS. 5A-5C show in vivo antiviral activity of JMX0207 against ZIKV.

It was next evaluated whether JMX0207 has favorable pharmacokinetic properties using a mouse model. As shown in Table 2 and FIG. 5A, JMX0207 displayed much better pharmacokinetic properties than the lead compound niclosamide. In contrast to niclosamide, which had a short $T_{1/2}$ and low $C_{max}$ (0.6 μM), when given to B6 mice orally at 40 mg/kg JMX0207 had an excellent pharmacokinetic profile with $C_{max}$ of 145 μM (Table 2), which was much higher than the $EC_{50}$ (0.3 μM) required to inhibit ZIKV. The longer $T_{1/2}$ (~11 h) was also more favorable to ensure less frequent drug administration to infected animals. Further pharmacokinetic study with different doses of JMX0207 indicated that the plasma drug concentration remained at the same level after the dose was reduced to 20 mg/kg (FIG. 5B). More importantly, mice with repeated oral dosing at 40 mg/kg/day for 7 days did not display any sign of toxicity (N=6). These results indicate good bioavailability and low toxicity for the derivative JMX0207.

TABLE 2

Pharmacokinetic properties of niclosamide and JMX0207

| | $T_{max}$ ± S.D.[a] (h) | $C_{max}$ ± S.D. (μM) | $T_{1/2}$ ± S.D. (h) | $AUC_{0\to\infty}$ ± S.D. |
|---|---|---|---|---|
| Niclosamide | 0.7 ± 0.4 | 0.6 ± 0.1 | 4.6 ± 1.0 | 3.5 ± 0.8 |
| JMX0207 | 1.2 ± 0.5 | 145 ± 18 | 11 ± 6.8 | 2719 ± 1018 |

[a]S.D., standard deviation

Example 9—JMX0207 Reduces Viremia in a ZIKV Mouse Model

Finally, the in vivo antiviral efficacy was evaluated using a viremia mouse model, as described previously. Zhang et al., "Characterization of the Contemporary Zika Virus in Immunocompetent Mice," *Hum. Vaccines Immunother.* 12:3107-3109 (2016) and Larocca et al., "Vaccine Protection Against Zika Virus From Brazil," *Nature* 536:474-478 (2016), both of which are hereby incorporated by reference in their entirety. The data showed that JMX0207 treatment at 20 mg/kg/day resulted in a significant reduction in ZIKV-induced viremia in the A129 mice inoculated with $1.7\times10^5$ PFU PRVABC59 ZIKV/mouse compared to the vehicle control (FIG. 5C). Overall, the results indicated that JMX0207 not only inhibited viral replication in vitro but also significantly reduced viremia in an in vivo animal model.

Example 10—JMX0207 is Effective Post-Infection

Figures 6A, 6B, 6C:
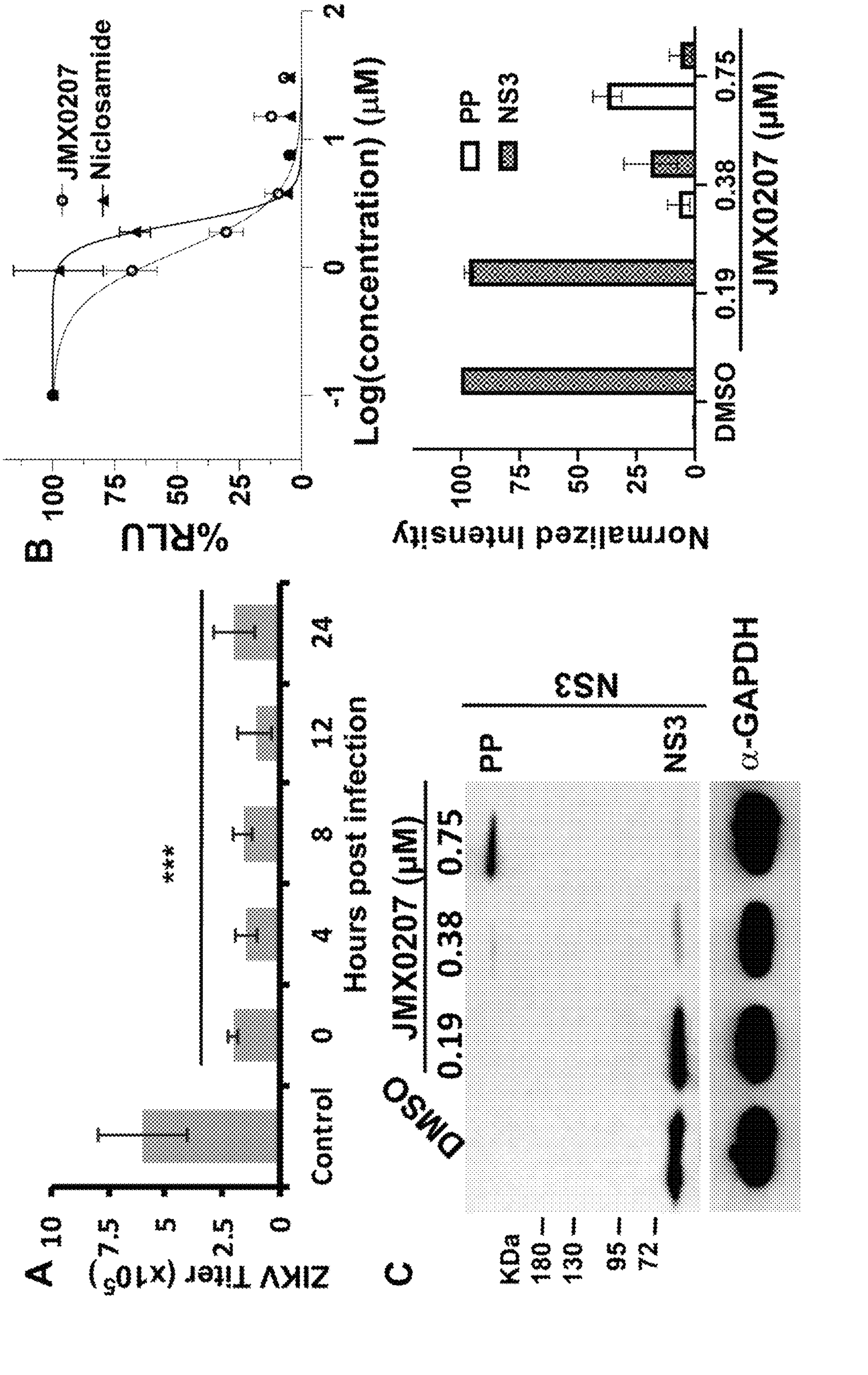
FIGS. 6A-6C show mechanism of action studies.

Antiviral inhibitors are generally divided into two categories, entry and post-entry (replication), respectively. To determine the mode of action, a time of addition experiment was first performed by adding JMX0207 at different time points post-infection (FIG. 6A). The results showed that JMX0207 was equally effective in reducing ZIKV titer even at 24 hrs post-infection. The results indicated that JMX0207 inhibited viral replication instead of viral entry, which agrees with the hypothesis that JMX0207, as a protease inhibitor, attenuates viral production in the post-entry replication stage.

Example 11—JMX0207 Inhibits Viral Replication Using a DENV2 Replicon Cell Line To further investigate the mechanism of action, a DENV2 replicon cell line was next used (Boonyasuppayakorn et al., "Amodiaquine, an Antimalarial Drug, Inhibits Dengue Virus Type 2 Replication and Infectivity," *Antiviral Res.* 106:125-134 (2014), which is hereby incorporated by reference in its entirety) to investigate if JMX0207 inhibited flavivirus replication without an entry step. The results indicated that both niclosamide and JMX0207 showed dose-responsive inhibition of DENV2 replication using the DENV2 replicon cell line (FIG. 6B). JMX0207 has slightly improved antiviral efficacy ($EC_{50\text{-}DN2}$ of 1.1 μM) compared to niclosamide ($EC_{50\text{-}DN2}$ of 2.0 μM) (FIG. 6B). Overall, the results indicate that JMX0207 is an effective antiviral to inhibit viral replication instead of entry.

Example 12—JMX0207 Treatment Inhibits Viral Polyprotein Precursor (PP) Processing Western blot (WB) analysis was carried out using an antibody recognizing ZIKV NS3 protein (FIG. 6C). The results showed that JMX0207 treatment led to dose-dependent reduction of viral NS3 protein production, presumably due to inhibition of viral production by JMX0207. In addition to reduced NS3 protein production, dose-dependent increase of a protein with high molecular weight (MW) was observed (FIG. 6C). It was known from the previous studies that the high MW protein is the unprocessed viral polyprotein precursor (PP) which can be recognized by the anti-NS3 antibody. Li et al., "Existing Drugs as Broad-Spectrum and Potent Inhibitors for Zika Virus by Targeting NS2B-NS3 Interaction," *Cell Res.* 27:1046-1064 (2017) and Brecher et al., "A Conformational Switch High-Throughput Screening Assay and Allosteric Inhibition of the Flavivirus NS2B-NS3 Protease," *PLoS Pathog.* 13:e1006411 (2017), both of which are hereby incorporated by reference in their entirety. The results are consistent with the mechanism by which JMX0207 inhibits viral protease function, leading to inhibition of viral PP processing, accumulation of non-functional viral PP, and finally virus reduction.

Example 13—JMX0207 Directly Binds to the NS2B-NS3 Interface

As a niclosamide derivative, JMX0207 is expected to directly bind to the viral NS3 protease, as did niclosamide. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. To demonstrate binding, a protein thermal shift assay (PTSA) was first carried out. The data indicated that the binding of JMX0207 stabilized the viral NS3 protease, leading to a 0.75° C. increase in $T_m$ of the viral protein. The data suggests that JMX0207 directly binds the viral NS3 protease.

To investigate the molecular interaction between JMX0207 and viral NS3 protease, JMX0207 was docked to the NS3 protease structure of DENV2 (PDB ID: 2FOM) using Induced Fit Docking (IFD) protocol, as described previously. Li et al., "Existing Drugs as Broad-Spectrum and Potent Inhibitors for Zika Virus by Targeting NS2B-NS3 Interaction," *Cell Res.* 27:1046-1064 (2017) and Li et al., "Erythrosin B is a Potent and Broad-Spectrum Orthosteric Inhibitor of the Flavivirus NS2B-NS3 Protease," *Antiviral Res.* 150:217-225 (2018), both of which are hereby incorporated by reference in their entirety. The docked pose (FIG. 7A) depicted JMX0207 can be well docked into the same 2B53 pocket identified from previous study. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. One $NO_2$ group of JMX0207 interacts with Y23 and F46 through R cations, while another $NO_2$ group forms H-bonds with Y33 and K61 and a salt bridge with K26. The phenyl ring on one side of JMX0207 interacts with L58 through hydrophobic interaction, and the other phenyl ring engages with Y33 with π-π L interaction. The phenol forms an H-bond with H60. The O atom on carbonyl group of JMX02027 forms an additional H-bond with K26 to further stabilize the binding. The IFD docking pose of JMX0207 and the IFD docking pose of niclosamide were superimposed. The overlay analysis demonstrates that JMX0207 binds at the 2B53 pockets on NS3 protease of ZIKV in a similar manner to that of niclosamide (FIGS. 7B, 7C), while an additional nitro group of JMX0207 also forms critical binding interactions with the protease.

Figures 7A, 7B, 7C, 7D:
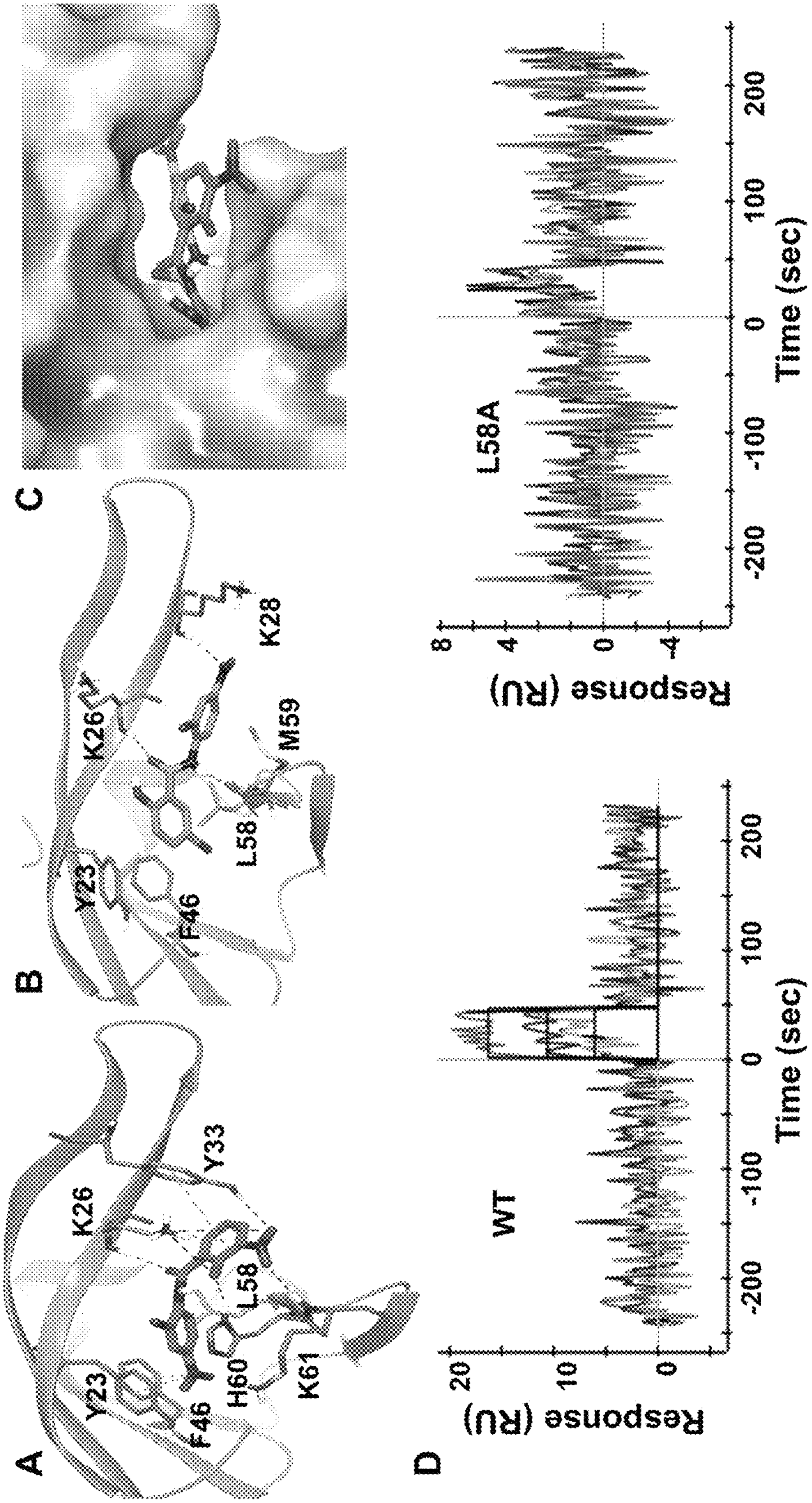
FIGS. 7A-7D show docking and mutagenesis.

To further investigate JMX0207 binding to viral NS3 protein, surface plasmon resonance (SPR) was used to measure the binding affinity of JMX0207 to the viral NS3 protease. Because several MBP-NS3 mutants were previously generated (Li et al., "Erythrosin B is a Potent and Broad-Spectrum Orthosteric Inhibitor of the Flavivirus NS2B-NS3 Protease," *Antiviral Res.* 150:217-225 (2018), which is hereby incorporated by reference in its entirety), MBP-NS3 fusion protein was used in the SPR analyses for better comparison. As shown in FIG. 7D, JMX0207 bound the viral NS3 protease with a binding affinity of 1.1 μM. Collectively, the data demonstrated that JMX0207 directly binds to the viral NS3 protease, with an affinity better than that for niclosamide (6.4 μM). Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. In a previous study, five NS3 mutants were generated, some of which had significant impact on binding of small molecule inhibitors to the NS2B-NS3 interface and on viral protease activity. Li et al., "Erythrosin B is a Potent and Broad-Spectrum Orthosteric Inhibitor of the Flavivirus NS2B-NS3 Protease," *Antiviral Res.* 150:217-225 (2018), which is hereby incorporated by reference in its entirety. The binding affinity of JMX0207 to these mutants was measured as well. The data showed that L58A abolished the binding of JMX0207 (Table 3, FIG. 7D). Two other mutations, I25A and H60A reduced the binding affinity 2 to 3 folds, whereas mutations Y23A and F46A do not have any effect.

TABLE 3

Binding affinity of JMX0207 to MBP-NS3 wild-type (WT) or mutant

| | WT | Y23A | I25A | F46A | L58A | H60A |
|---|---|---|---|---|---|---|
| $K_D$ (μM) | 1.1 | 1.2 | 2.3 | 1.2 | ND[a] | 2.9 |

ND[a], no detectable binding.

Dengue and Zika viruses cause significant human disease, for which there are no specific vaccines or therapies. Therefore, development of effective antivirals is urgent. Previously, an existing FDA-approved drug, niclosamide, was identified as a potent antiviral against DENV and ZIKV. However, the poor pharmacokinetic properties of niclosamide prevent its clinical use to treat DENV and ZIKV infections.

In this study, a small in-house compound library of niclosamide derivatives were screened and JMX0207 was identified as a candidate inhibitor with improved properties. JMX0207 inhibited the viral NS2B-NS3 protease activity of DENV2 with better efficacy in vitro than niclosamide. In cell culture, JMX0207 significantly inhibited the growth of representative flaviviruses, including DENV2 and ZIKV, with $EC_{50}$ in nanomolar range. By using IFA, WB, and qRT-PCR analyses, it was shown that JMX0207 also significantly inhibited viral RNA synthesis and protein production. More importantly, compared to niclosamide, JMX0207 has reduced cytotoxicity profile towards human cells, indicating a larger therapeutic window towards these flaviviruses. In addition, it was shown that JMX0207 could rescue ZIKV-relevant neural progenitor cells from viral infection in a dose-dependent manner. Moreover, JMX0207 could almost completely protect 3D cortical organoids originated from neural stem cells from ZIKV infection. The findings establish the efficiency of JMX0207 to eliminate infection of ZIKV from human neural progenitor cells, and provide a path forward to minimize the risk of fetal acquired microcephaly resulting from ZIKV infection of pregnant women. Lessler et al., "Assessing the Global Threat From Zika Virus," *Science.* 353:aaf8160 (2016), which is hereby incorporated by reference in its entirety. Furthermore, it was shown that JMX0207 displayed significantly improved pharmacokinetic properties, compared to the parent compound niclosamide. The improved pharmacokinetics allowed for carrying out in vivo antiviral efficacy studies using an animal model for ZIKV infection. The data showed that JMX0207 treatment markedly reduced viral viremia in the A129 ZIKV mouse model infected with clinical strain ZIKV PRVABC59. Mechanistically, it was shown that JMX0207 directly binds to the viral NS3 protease with improved binding affinity, compared to its lead drug niclosamide. It was also shown that JMX0207 treatment led to dose-dependent inhibition of viral polyprotein precursor processing, a direct consequence of inhibition of viral protease activity.

Example 14—Discussion of Examples 2-13

It is concluded that the niclosamide derivative JMX0207 is a valuable candidate for further study, due to its demonstrated ability to inhibit several activities required for ZIKV propagation. When paired with its reduced cytotoxicity profile and superior pharmacokinetic properties, these positive attributes indicate that JMX0207 might effectively be used to combat viral progression following initial infection with ZIKV. Successful development of this compound would be a valuable tool in the prevention of negative ZIKV-related outcomes, including Guillain-Barre syndrome, neuropathy and myelitis, as well as pregnancy-related outcomes including miscarriage, preterm birth, and congenital Zika syndrome.

Example 15—Structure-Activity Relationship (SAR) Studies

Figure 9:
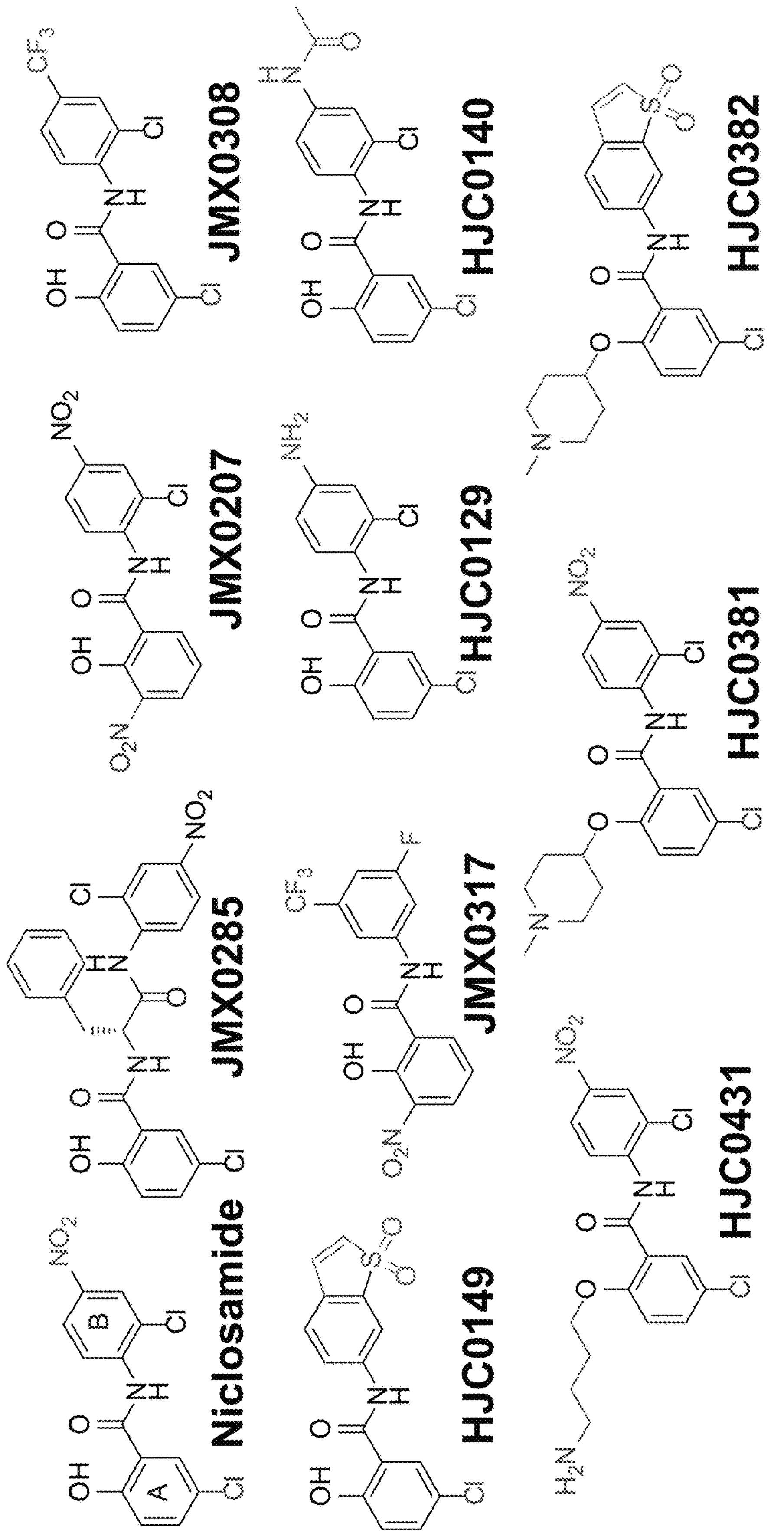
FIG. 9 shows Chemical structures of NM and its ten analogs from preliminary structure-activity relationship (SAR) studies.

Previously, it was shown that niclosamide (NM), nitazoxanide (NTZ) and their derivatives are potent protease inhibitors via a non-competitive mechanism by abolishing interactions between the viral protease NS3 and its cofactor NS2B. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. Viral reduction assay shows that NM, NTZ and their derivatives are relatively potent and broad-spectrum inhibitors with $EC_{50}$s in low micromolar range for several representative flaviviruses, including Dengue virus (DENV), Zika virus (ZIKV), West Nile virus (WNV), yellow fever virus (YFV) and Japanese encephalitis virus (JEV). It was also shown that the drugs can suppress virus growth in placental and neural progenitor cells relevant to ZIKV pathogenesis. Li et al., "Existing Drugs as Broad-Spectrum and Potent Inhibitors for Zika Virus by Targeting NS2B-NS3 Interaction," *Cell Res.* 27:1046-1064 (2017), which is hereby incorporated by reference in its entirety. In preliminary structure-activity relationship (SAR) studies by synthesizing and testing NM derivatives, several active analogs (structures shown in FIG. 9) are identified. First, the amide linker between A and B-ring of niclosamide was explored. Compound (JMX0285) with a phenylalanine moiety linker displayed potent ZIKV (ZK) and DENV2 (DN2) inhibitory activities, with $EC_{50}$ values of 0.3 μM and 0.48 μM, respectively (Table 4). Next, the effect of the substitution on A, B-ring was investigated. Compounds with m-$NO_2$ on A-ring (JMX0207), p-$CF_3$ on B-ring (JMX0308), 1,1-dioxidobenzo[b]thiophen-6-yl as B-ring (HJC0149), and with m-$NO_2$ on A-ring and m-$CF_3$, m-F on B-ring (JMX0317) showed potent ZIKV inhibition, with $EC_{50}$ values of 0.3 μM, 0.12 μM, 1.1 μM and 0.12 μM, respectively. Moreover, use of p-CF3 instead of $NO_2$ on B-ring (JMX0308) significantly improved ZIKV and DENV2 inhibitory activities ($EC_{50}$=0.09/0.12 μM), indicating that the unfavorable nitro group can be replaced with other more druglike moieties. Importantly, the introduction of amino group on A-ring (HJC0381, HJC0382 and HJC0431) significantly improves the aqueous solubility, meanwhile displaying potent inhibitory activities against protease and virus. Interestingly, use of 4-amino (HJC0129) or 4-acetamido (HJC0140) on B-ring resulted in a complete loss of antiviral activities while they retained inhibition against protease (Table 4). These preliminary SAR results demonstrate that the linker, A-ring and B-ring of NM are tolerable for chemical modifications and drug properties improvement. Further optimization of NM and the identified new lead compounds will be pursued. In addition, plasma binding and cell permeability was conducted as described in Waters et al., "Validation of a Rapid Equilibrium Dialysis Approach for the Measurement of Plasma Protein Binding," *J. Pharm. Sci.* 97:4586-4595 (2008) and Behnam et al., "Discovery of Nanomolar Dengue and West Nile Virus Protease Inhibitors Containing a 4-Benzyloxyphenylglycine Residue," *J. Med. Chem.* 58:9354-9370 (2015), both of which are hereby incorporated by reference in their entirety (Table 4). JMX0207 shows improvement in plasma binding (86% vs 99%), cell permeability (>1E-6 cm/s), and binding affinity ($K_D$) to NS3, compared to its parent niclosamide (NM) (Table 4).

TABLE 4

Preliminary SAR results in protease ($IC_{50}$) or in A549 cells ($EC_{50}$, $CC_{50}$) in μM

| (all in μM) | LogP | $IC_{50\text{-}pro(DN2)}$ | $EC_{50\text{-}DN2}$ | $EC_{50\text{-}ZK}$ | $CC_{50}$ | $K_D$ | Plasm | Perme. |
|---|---|---|---|---|---|---|---|---|
| NM | 3.38 | 12.3 | 0.55 | 0.48 | 4.8 | 6.4 | 99% | 2.5E−7 |
| JMX0207 | 2.72 | 8.1 | 0.36 | 0.3 | 33.9 | 1.1 | 86% | 1.3E−6 |
| JMX0285 | 3.84 | 5.7 | 0.48 | 0.3 | 16.5 | μM | | 2.5E−7 |
| JMX0308 | 4.49 | 2.7 | 0.09 | 0.12 | 2.01 | | | 2.7E−7 |
| JMX0317 | 3.26 | 8.4 | 0.2 | 0.12 | 20.4 | | | 2.9E−6 |
| HJC0129 | 2.76 | 11.3 | >30 | >30 | 176 | | | |
| HJC0140 | 2.47 | 25.5 | >30 | >30 | >200 | | | In cm/s |
| HJC0149 | 2.41 | 20.3 | 0.9 | 1.1 | 241 | | | |
| HJC0381 | 2.38 | 25.9 | 1.2 | 3.9 | 91.1 | | | |
| HJC0382 | 2.62 | 26 | 0.8 | 2.0 | 8.4 | | | |
| HJC0431 | 3.9 | 34.0 | 2.2 | 0.36 | 28.4 | | | |
| NTZ | 2.14 | 15.9 | 0.3 | 1.5 | 77 | | | |

$IC_{50\text{-}pro}$/$EC_{50\text{-}DN2}$/$EC_{50\text{-}ZK}$/$CC_{50}$: Compound concentration required to reduce 50% of protease, infectivity of DENV-2 (DN2) and ZIKV (ZK), and cell viability, respectively.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of inhibiting viral replication comprising: contacting one or more cells that have been infected with a virus with an effective amount of a compound of formula (I) or a pharmaceutically acceptable salt thereof (I)

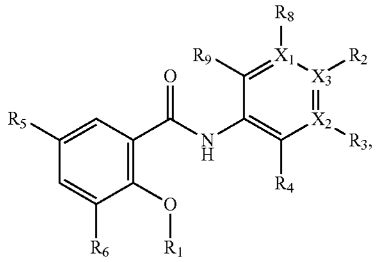

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_8$ is hydrogen, halogen, or trihalomethane;

$R_9$ is halogen or hydrogen;

$X_1$, $X_2$, and $X_3$ are independently selected from C and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_8$ is hydrogen, and $R_9$ is hydrogen; and wherein the virus comprises a flavivirus.

2. The method of claim 1, wherein, in the compound of formula (I), $R_3$ is fluorine or hydrogen.

3. The method of claim 1, wherein, in the compound of formula (I), $R_4$ is chlorine or hydrogen.

4. The method of claim 1, wherein, in the compound of formula (I), $R_5$ is chlorine or hydrogen.

5. The method of claim 1, wherein in the compound of formula (I), when $R_2$ or $R_6$ is nitrogen oxide, $R_2$ or $R_6$ is independently selected from the group consisting of $NO_2$, NO, $N_2O$, and $N_2O_5$.

6. The method of claim 1, wherein the compound of formula (I) is selected from the compound of formulae (Ia)-(Il) and (In)-(Ip):

(Ia)

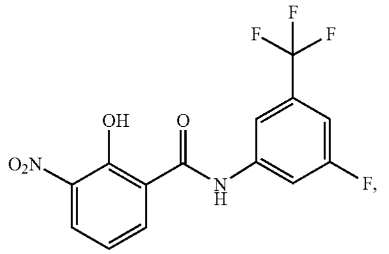

-continued (Ib)

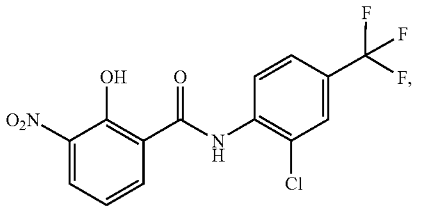

(Ic)

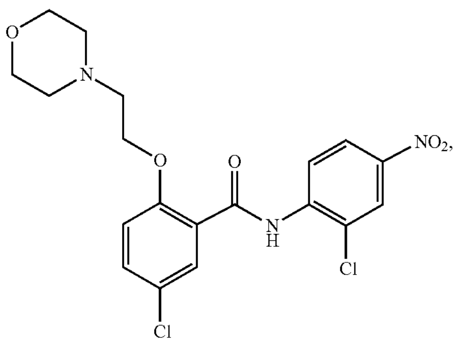

(Id)

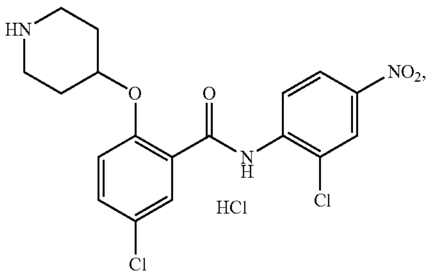

(Ie)

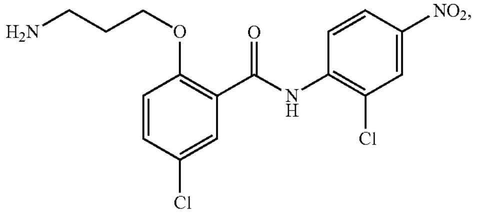

(If)

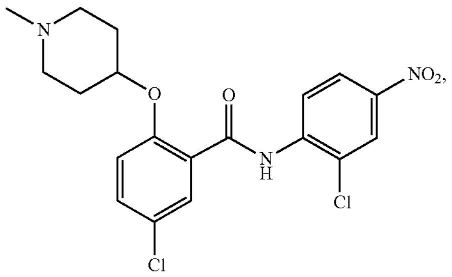

(Ig)

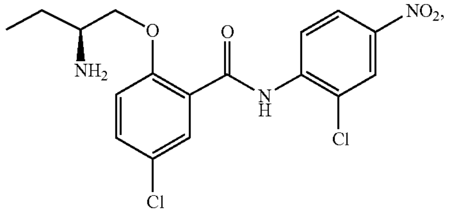

(Ih)

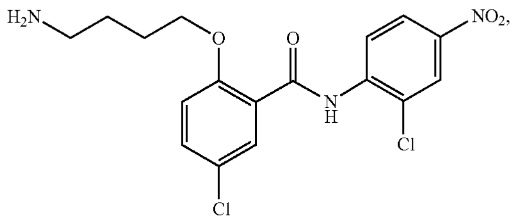

(Ii)

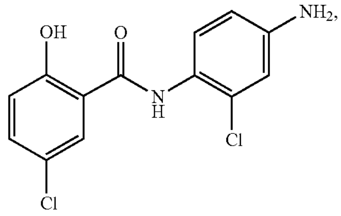

(Ij)

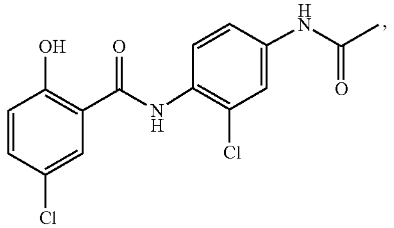

(Ik)

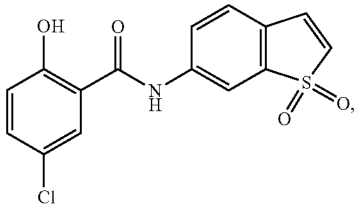

(Il)

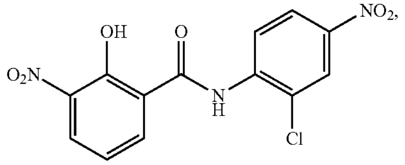

(In)

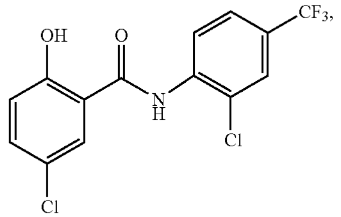

(Io)

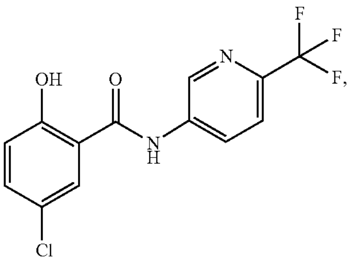

(Ip)

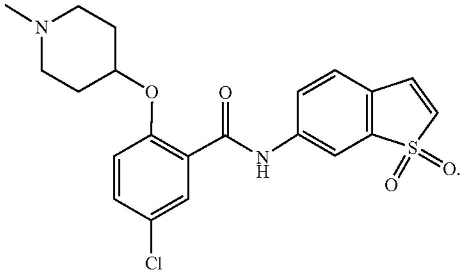

7. The method of claim 1, wherein the contacting one or more cells that have been infected with a flavivirus comprises administering the compound to a subject.

8. The method of claim 7, wherein the flavivirus is selected from the group consisting of Zika virus, Dengue virus serotype 1, Dengue virus serotype 2, Dengue virus serotype 3, Dengue virus serotype 4, yellow fever virus, West Nile virus, and Japanese encephalitis virus.

9. The method of claim 8, wherein the flavivirus is Zika virus.

10. A method of treating and/or preventing a flavivirus infection and/or a condition resulting from a flavivirus infection, said method comprising:

administering an effective amount of a compound of formula (I) or a pharmaceutically acceptable salt thereof (I)

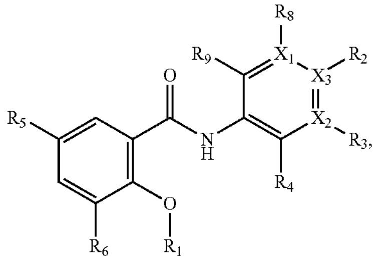

wherein $R_1$ is independently selected from the group consisting of amine, amide, $C_1$-$C_{23}$ alkyl, aryl, heteroaryl, carbocycle, heterocycle, halogen, trifluoromethyl, and hydrogen;

$R_2$ is independently selected from the group consisting of trihalomethane, hydrogen, nitrogen oxide, amine, amide, and alkyl;

$R_3$ is independently selected from the group consisting of halogen, hydrogen, nitrogen oxide, and sulfur;

$R_4$ is halogen or hydrogen;

$R_5$ is halogen or hydrogen; and $R_6$ is nitrogen oxide or hydrogen;

$R_8$ is hydrogen, halogen, or trihalomethane;

$R_9$ is halogen or hydrogen;

$X_1$, $X_2$, and $X_3$ are independently selected from C and N;

wherein $R_2$ and $R_3$ may optionally form a heterocycle comprising one or more sulfur oxide; and wherein $R_1$ is not hydrogen when $R_2$ is $NO_2$, $R_3$ is hydrogen, $R_4$ is chlorine, $R_5$ is chlorine, $R_6$ is hydrogen, $R_8$ is hydrogen, and $R_9$ is hydrogen, under conditions effective to treat and/or prevent a flavivirus infection and/or a condition resulting from a flavivirus infection.

11. The method of claim 10, wherein, in the compound of formula (I), $R_3$ is fluorine or hydrogen.

12. The method of claim 10, wherein, in the compound of formula (I), $R_4$ is chlorine or hydrogen.

13. The method of claim 10, wherein, in the compound of formula (I), $R_5$ is chlorine or hydrogen.

14. The method of claim 10, wherein in the compound of formula (I), $R_2$ or $R_6$ is nitrogen oxide, $R_2$ or $R_6$ is independently selected from the group consisting of $NO_2$, NO, $N_2O$, and $N_2O_5$.

15. The method of claim 10, wherein the compound of formula (I) is selected from the compound of formulae (Ia)-(Il) and (In)-(Ip):

(Ia)

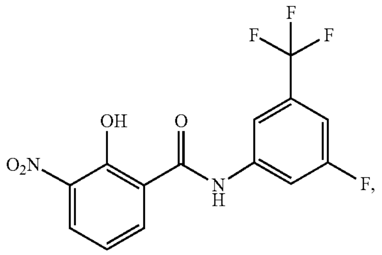

(Ib)

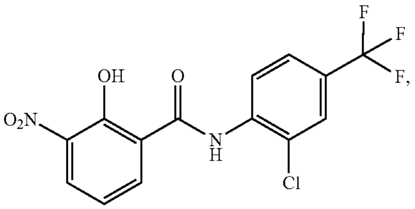

(Ic)

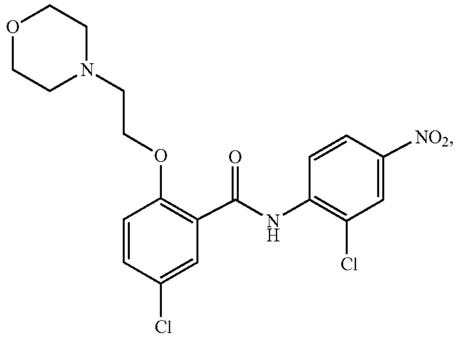

(Id)

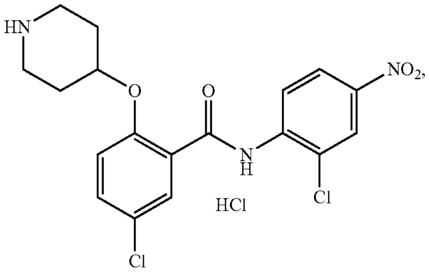

-continued (Ie)

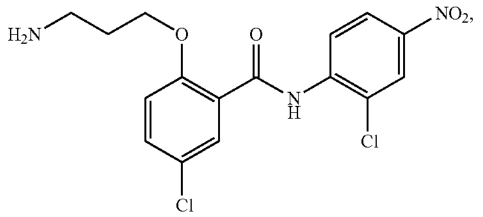

(If)

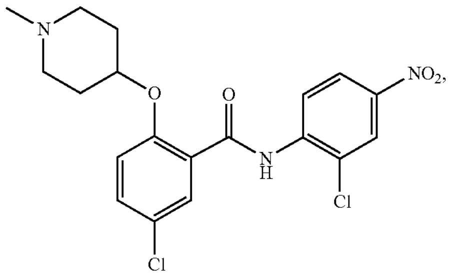

(Ig)

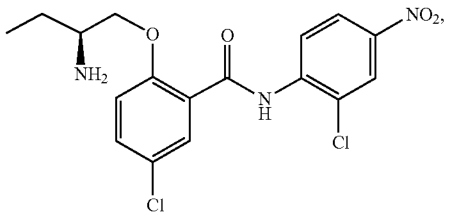

(Ih)

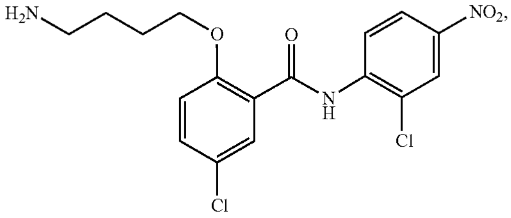

(Ii)

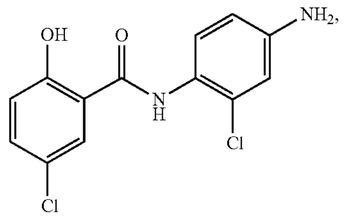

(Ij)

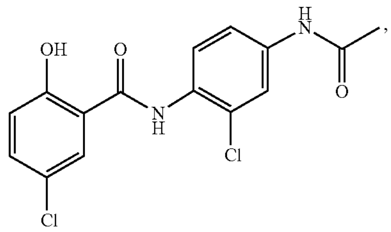

(Ik)

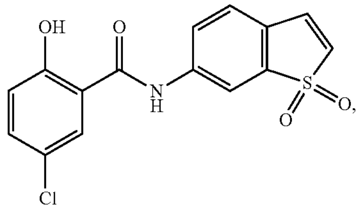

-continued (Il)

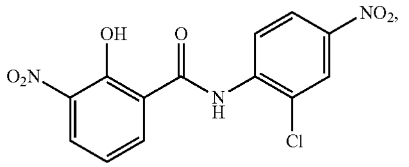

(In)

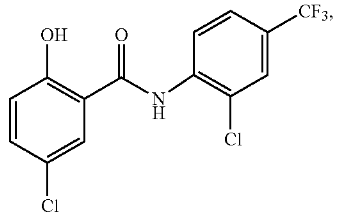

(Io)

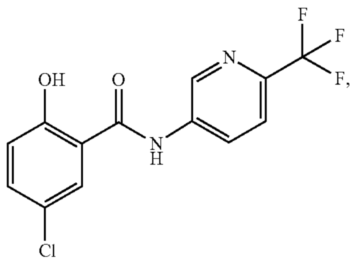

(Ip)

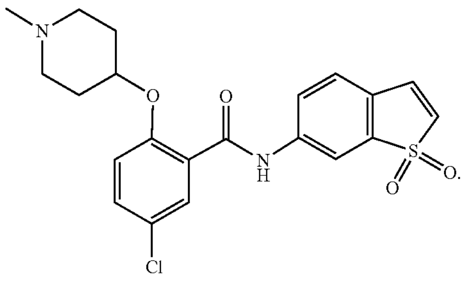

16. The method of claim 10 further comprising:

selecting a subject that has an infection caused by a flavivirus or is at risk of developing an infection caused by a flavivirus.

17. The method of claim 10, wherein the flavivirus is selected from the group consisting of Zika virus, Dengue virus serotype 1, Dengue virus serotype 2, Dengue virus serotype 3, Dengue virus serotype 4, yellow fever virus, West Nile virus, and Japanese encephalitis virus.

18. The method of claim 17, wherein the flavivirus is Zika virus.

19. The method of claim 10, wherein said method further comprises:

administering the compound of formula (I) to a selected subject orally, by inhalation, by intranasal instillation, topically, transdermally, intradermally, parenterally, subcutaneously, intravenous injection, intra-arterial injection, intramuscular injection, intrapleurally, intraperitoneally, intrathecally, or by application to a mucous membrane.

20. The method of claim 10 further comprising:

repeating said administering formula (I).

21. The method of claim 10 further comprising:

administering one or more additional agents.

22. The method of claim 10, wherein the subject is an infant, a juvenile, or an adult.

23. The method of claim 10, wherein the flavivirus infection is prevented.

24. The method of claim 10, wherein the flavivirus infection is treated.

25. A method of inhibiting viral replication comprising:

contacting one or more cells that have been infected with a virus with an effective amount of a compound selected from formulae (Ia)-(Il) and (In)-(Ip):

(Ia)

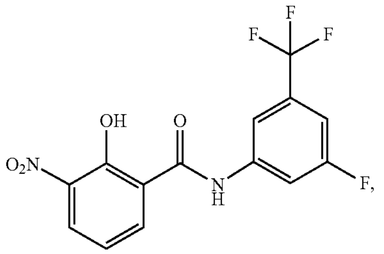

(Ib)

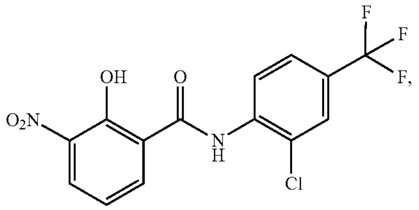

(Ic)

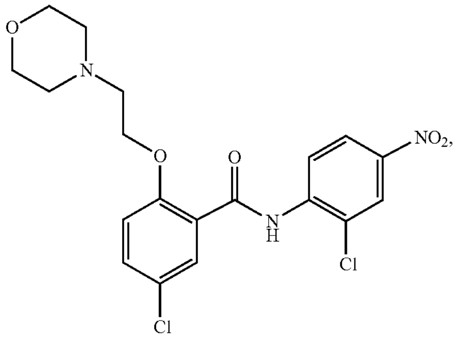

(Id)

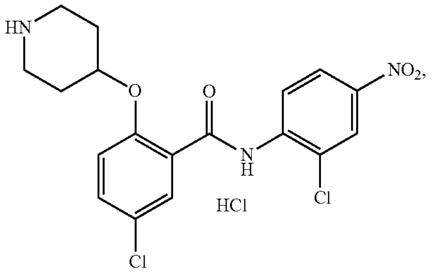

(Ie)

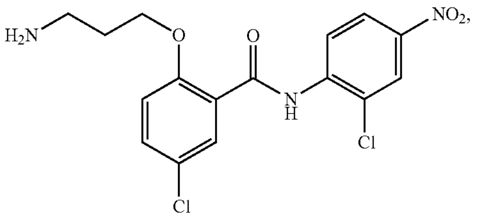

-continued (If)

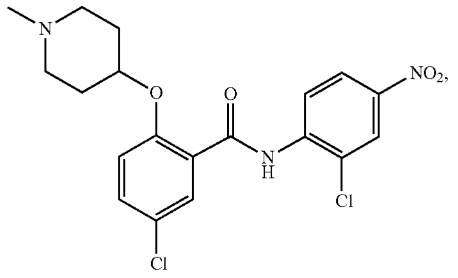

(Ig)

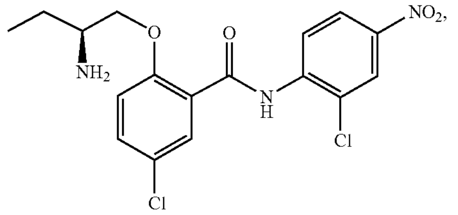

(Ih)

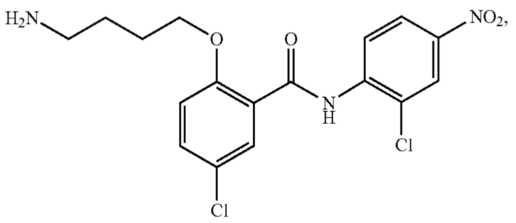

(Ii)

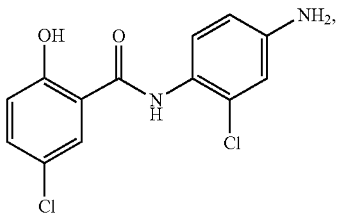

(Ij)

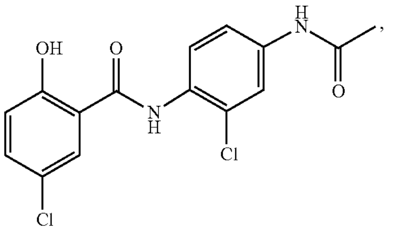

(Ik)

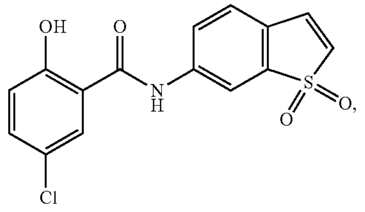

-continued (Il)

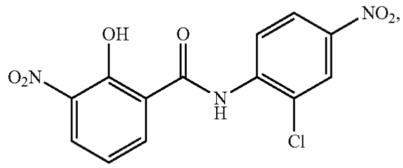

(In)

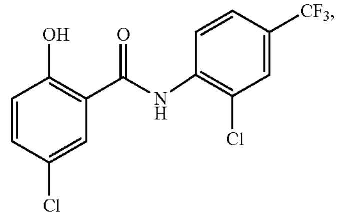

(Io)

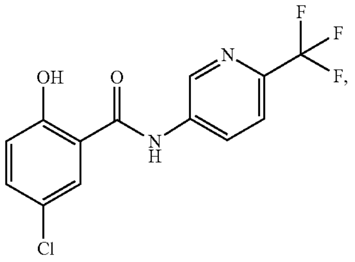

(Ip)

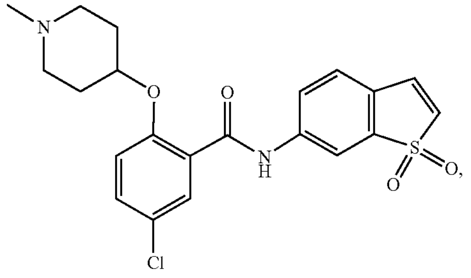

or a pharmaceutically acceptable salt thereof, wherein the virus comprises a flavivirus.

26. The method of claim 25, wherein the contacting one or more cells that have been infected with a flavivirus comprises administering the compound to a subject.

27. The method of claim 25, wherein the flavivirus is selected from the group consisting of Zika virus, Dengue virus serotype 1, Dengue virus serotype 2, Dengue virus serotype 3, Dengue virus serotype 4, yellow fever virus, West Nile virus, and Japanese encephalitis virus.

28. The method of claim 27, wherein the flavivirus is Zika virus.

* * * * *